United States Patent
Rodell et al.

(10) Patent No.: US 10,507,235 B2
(45) Date of Patent: *Dec. 17, 2019

(54) YEAST-BASED IMMUNOTHERAPY FOR CHORDOMA

(71) Applicants: GLOBEIMMUNE, INC., Louisville, CO (US); THE UNITED STATES OF AMERICA, AS REPRESENTED BY THE SECRETARY, DEPARTMENT OF HEALTH AND HUMAN SERVICES, Bethesda, MD (US)

(72) Inventors: Timothy C. Rodell, Aspen, CO (US); David Apelian, Boonton Township, NJ (US); Claudia Palena, Potomac, MD (US); Jeffrey Schlom, Potomac, MD (US)

(73) Assignees: GlobeImmune, Inc., Louisville, CO (US); The USA, as represented by the Secretary, Dept. of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/778,118

(22) PCT Filed: Mar. 19, 2014

(86) PCT No.: PCT/US2014/031183
§ 371 (c)(1),
(2) Date: Sep. 18, 2015

(87) PCT Pub. No.: WO2014/186047
PCT Pub. Date: Nov. 20, 2014

(65) Prior Publication Data
US 2016/0271238 A1    Sep. 22, 2016

Related U.S. Application Data

(60) Provisional application No. 61/803,332, filed on Mar. 19, 2013.

(51) Int. Cl.
*A61K 39/00* (2006.01)
(52) U.S. Cl.
CPC .... *A61K 39/0011* (2013.01); *A61K 2039/521* (2013.01); *A61K 2039/545* (2013.01); *Y02A 50/489* (2018.01)
(58) Field of Classification Search
None
See application file for complete search history.

(56) References Cited

U.S. PATENT DOCUMENTS

| | | |
|---|---|---|
| 4,775,622 A | 10/1988 | Hitzeman et al. |
| 5,234,830 A | 8/1993 | Oshima et al. |
| 5,310,654 A | 5/1994 | Isberg et al. |
| 5,413,914 A | 5/1995 | Franzusoff |
| 5,830,463 A | 11/1998 | Duke et al. |
| 5,858,378 A | 1/1999 | Bostwick |
| 5,919,651 A | 7/1999 | Hitzeman et al. |
| 6,410,026 B1 | 6/2002 | Srivastava |
| 7,083,787 B2 | 8/2006 | Duke et al. |
| 7,175,839 B1 | 2/2007 | Hiserodt |
| 7,439,042 B2 | 10/2008 | Duke et al. |
| 7,465,454 B2 | 12/2008 | Franzusoff et al. |
| 9,198,941 B2 | 12/2015 | Palena et al. |
| 2002/0044948 A1 | 4/2002 | Samir et al. |
| 2003/0035810 A1 | 2/2003 | Caplan |
| 2006/0009404 A1 | 1/2006 | Williams |
| 2007/0172503 A1 | 7/2007 | Selitrennikoff et al. |
| 2007/0224208 A1 | 9/2007 | Guo et al. |
| 2008/0003239 A1 | 1/2008 | Duke et al. |
| 2010/0034840 A1 | 2/2010 | Apelian et al. |
| 2010/0111912 A1 | 5/2010 | Apelian et al. |
| 2010/0189749 A1 | 7/2010 | Franzusoff et al. |
| 2011/0229524 A1 | 9/2011 | Fritsche et al. |
| 2011/0256098 A1 | 10/2011 | Apelian et al. |
| 2012/0321664 A1 | 12/2012 | Bellgrau et al. |
| 2016/0106824 A1 | 4/2016 | Palena et al. |

(Continued)

FOREIGN PATENT DOCUMENTS

| | | |
|---|---|---|
| EP | 0414404 | 2/1991 |
| FR | 2486400 | 1/1982 |

(Continued)

OTHER PUBLICATIONS

Jambhekar et al. Revisiting Chordoma With Brachyury, a "New Age" Marker: Analysis of a Validation Study on 51 Cases. Archives of Pathology & Laboratory Medicine: 134(8): 1181-1187, Aug. 2010.*
Jambhekar et al. (Arch. Pathol. Lab. Med. 134: 1181-1187, Aug. 2010).*
Official Action (with English translation) for Japanese Patent Application No. 2016-504343 dated Dec. 5, 2017, 5 pages.
Official Action for Australian Patent Application No. 2014265873 dated Jan. 15, 2018, 3 pages.
Official Action for European Patent Application No. 14797995.9 dated Mar. 8, 2018, 5 pages.
Official Action (with English translation) for Japanese Patent Application No. 2016-504343 dated Jun. 5, 2018, 5 pages.
Official Action (with English translation) for Taiwanese Patent Application No. 103110360 dated Aug. 28, 2017, 8 pages.

(Continued)

*Primary Examiner* — Alana Harris Dent
(74) *Attorney, Agent, or Firm* — Sheridan Ross P.C.

(57) ABSTRACT

One embodiment of the invention relates to a method to treat chordoma in an individual who has chordoma. The method includes the step of administering to an individual who has chordoma, an immunotherapeutic composition comprising: (a) a yeast vehicle; and (b) a cancer antigen comprising at least one Brachyury antigen. Another embodiment of the invention relates to the use of an immunotherapeutic composition comprising a yeast vehicle and a cancer antigen comprising at least one Brachyury antigen to chordoma in an individual who has chordoma. Yet another embodiment of the invention relates to the use an immunotherapeutic composition comprising a yeast vehicle.

34 Claims, 1 Drawing Sheet

Specification includes a Sequence Listing.

(56) References Cited

U.S. PATENT DOCUMENTS

| | | | |
|---|---|---|---|
| 2017/0246276 A1 | 8/2017 | Palena et al. | |
| 2018/0214525 A1 | 8/2018 | King et al. | |

FOREIGN PATENT DOCUMENTS

| | | | |
|---|---|---|---|
| WO | WO 2007/008780 | | 1/2007 |
| WO | WO 2007/092792 | | 8/2007 |
| WO | WO 2007/133835 | | 11/2007 |
| WO | WO 2008/106551 | | 9/2008 |
| WO | WO 2010/065626 | | 6/2010 |
| WO | WO 2010/121180 | | 10/2010 |
| WO | WO 2011/115914 | | 9/2011 |
| WO | WO 2012/019127 | | 2/2012 |
| WO | WO 2012/083302 | | 6/2012 |
| WO | WO 2012/109404 | | 8/2012 |
| WO | WO 2012/125998 | A1 * | 9/2012 |
| WO | WO 2012/174220 | | 12/2012 |
| WO | WO 2013/025972 | | 2/2013 |

OTHER PUBLICATIONS

Nelson et al., "An integrated functional genomics approach identifies the regulatory network directed by brachyury (T) in chordoma," Journal of Pathology, 2012, vol. 228, Iss. 3, pp. 274-285.
Official Action (English translation) for Chinese Patent Application No. 201480028312.1 dated Apr. 23, 2018, 7 pages.
Official Action (with English translation) for Russian Patent Application No. 2015144511/15 dated Apr. 4, 2018, 14 pages.
Staab et al., "Spot-Scanning-Based Proton Therapy for Extracranial Chordoma," International Journal of Radiation Oncology * Biology * Physics, 2011, vol. 81, Iss. 4, pp. e489-e496.
Official Action (English translation) for Chinese Patent Application No. 201480028312.1 dated May 27, 2017, 6 pages.
Official Action for European Patent Application No. 14797995.9 dated Jul. 14, 2017, 5 pages.
Reis E Sousa et al. "Conditioning of Dendritic Cells by Pathogen-Derived Stimuli," Immunobiology, 2001, vol. 204, Iss. 5, pp. 595-597.
Official Action (with English translation) for Israeli Patent Application No. 241384 dated Aug. 8, 2018, 7 pages.
Hayama et al., "Extremely simple, rapid and highly efficient transformation method for the yeast Saccharomyces cerevisiae using glutathione and early log phase cells," Journal of Bioscience and Bioengineering, 2002, vol. 94, Iss. 2, pp. 166-171. (Abstract only).
Notice of Acceptance for Australian Patent Application No. 2014265873 dated Jan. 7, 2019, 3 pages.
Official Action for European Patent Application No. 14797995.9 dated Jan. 24, 2019, 5 pages.
Official Action (with English translation) for Israeli Patent Application No. 241384 dated Feb. 24, 2019, 7 pages.
Notice of Allowance (with English translation) for Japanese Patent Application No. 2016-504343 dated Mar. 5, 2019, 2 pages.
Official Action (with English translation) for Russian Patent Application No. 2015144511 dated Sep. 3, 2018, 16 pages.
Decision to Grant (with English translation) for Russian Patent Application No. 2015144511 dated Dec. 10, 2018, 16 pages.
Official Action (with English translation) for Taiwanese Patent Application No. 103110360 dated Aug. 30, 2018, 9 pages.
Bachman et al., "Recall proliferation potential of memory CD8+ T cells and antiviral protection," Journal of Immunology, 2005, vol. 175, pp. 4677-4685.
Bizzini et al. "Use of live Saccharomyces cerevisiae cells as a biological response modifier in experimental infections," FEMS Microbiology Immunology, 1990, vol. 64, pp. 155-168.
Brake et al. "alpha-Factor-directed synthesis and secretion of mature foreign proteins in Saccharomyces cerevisiae," Proceedings of the National Academy of Sciences USA, Aug. 1984, vol. 81, pp. 4642-4646.
Chugh et al. "Chordoma: The Nonsarcoma Primary Bone Tumor," The Oncologist, Nov. 2007, vol. 12, No. 11, pp. 1344-1350.
Di Maio et al. "Current comprehensive management of cranial base chordomas: 10-year meta-analysis of observational studies," Journal of Neurosurgery, Dec. 2011, vol. 115, No. 6, pp. 1094-1105.
Efferson et al., "Stimulation of human T cells by an influenza A vector expressing a CTL epitope from the HER-2/neu protooncogene results in higher numbers of antigen-specific TCRhi cells than stimulation with peptide. Divergent roles of IL-2 and IL-15," Anticancer research, 2005, vol. 25, pp. 715-724.
Eto et al., "Immunization with recombinant Escherichia coli expressing retinal S-antigen-induced experimental autoimmune uveitis (EAU) in Lewis rats", Cellular Immunology, vol. 147, No. 1 Mar. 1993, pp. 203-214.
Ferraresi et al. "Chordoma: clinical characteristics, management and prognosis of a case series of 25 patients," BMC Cancer, Jan. 2010, vol. 10, 10 pages.
Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.
Franzusoff, A. et al. "Yeasts Encoding Tumour Antigens in Cancer Immunotherapy," Expert Opinion on Biological Therapy, Apr. 2005, vol. 5, No. 4, pp. 565-575.
Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.
Hamilton et al. Immunological targeting of tumor cells undergoing an epithelial-mesenchymal transition via a recombinant brachyury-yeast vaccine, Oncotarget, Oct. 2013, vol. 4, No. 10, pp. 1777-1790.
Holz et al., "A micro-scale process for high-throughput expression of cDNAs in the yeast Saccharomyces cerevisiae," Protein Expression and Purification, 2002, vol. 25, Iss. 3, pp. 372-378.
Kilic et al. "Brachyury expression predicts poor prognosis at early stages of colorectal cancer." European Journal of Cancer, May 2011, vol. 47, No. 7, pp. 1080-1085.
Klepfer et al. "Characterization of rabies glycoprotein expressed in yeast," Archives of Virology, 1993, vol. 128, pp. 269-286.
Launay et al. "Efficacy of epidermal growth factor receptor targeting in advanced chordoma: case report and literature review," BMC Cancer, Oct. 2011, vol. 11, 4 pages.
Lu, et al., "Mutation-Selective Tumor Remission with Ras-Targeted, Whole Yeast-Based Immunotherapy," Cancer Research, 2004, vol. 64, pp. 5084-5088.
Moore et al., "Novel yeast-based vaccine against HIV-SF2 gp160 promotes a cytotoxic 43-62 cell response." FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USA; Jun. 2-6, 1996.
Mosolits et al., "Therapeutic vaccination in patients with gastrointestinal malignancies. A review of immunological and clinical results," Annals of Oncology, 2005, vol. 16, Iss. 6, pp. 847-862.
Palena et al. "The Human T-Box Mesodermal Transcription Factor Brachyury Is a Candidate Target for T-Cell-Mediated Cancer Immunotherapy," Clinical Cancer Research, Apr. 15, 2007, vol. 13, No. 8, pp. 2471-2478.
Pamir et al. "Tumor-biology and current treatment of skull-base chordomas," Advances and Technical Standards in Neurosurgery, Edited by J.D. Pickard, 2008, vol. 33, pp. 36-129.
Sadanaga et al., "Dendritic Cell Vaccination with MAGE Peptide Is a Novel Therapeutic Approach for Gastrointestinal Carcinomas," Clinical Cancer Research, 2001, vol. 7, Iss. 8, pp. 2277-2284.
Schreuder et al. "Yeast expressing hepatitis B virus surface antigen determinants on its surface: implications for a possible oral vaccine," Vaccine, Apr. 1996, vol. 14, No. 5, pp. 383-388.
Sinai et al. "Enhancement of Resistance to Infectious Diseases by Oral Administration of Brewer's Yeast," Infection and Immunity, May 1974, vol. 9, No. 5, pp. 781-787.
Stacchiotti et al. "Systemic Therapy Options for Unresectable and Metastatic Chordomas," Current Oncology Reports, Aug. 2011, vol. 13, No. 4, pp. 323-330.

(56) References Cited

OTHER PUBLICATIONS

Stubbs, et al., "Whole Recombinant Yeast Vaccine Activates Dendritic Cells and Elicits Protective Cell-Mediated Immunity," National Medicine, May 2001, vol. 7, No. 5, pp. 1-5.
Valenzuela et al. "Antigen engineering in yeast: Synthesis and assembly of hybrid hepatitis B surface antigen-Herpes simplex 1 gD particles", Bio/Technology, Apr. 1985, vol. 3, 323-326.
Walcott et al. "Chordoma: current concepts, management, and future directions," The Lancet Oncology, Feb. 2012, vol. 13, pp. e69-e76.
Wheeler, "Preventive vaccines for cervical cancer," Salud p'ublica de M'exico, 1997, vol. 39, pp. 283-287.
Yang et al. "Corroboration of a familial chordoma locus on chromosome 7q and evidence of genetic heterogeneity using single nucleotide polymorphisms (SNPs)," International Journal of Cancer, Sep. 2005, vol. 116, No. 3, pp. 487-491.
Yoshiyuki et al., "Extremely simple, rapid and highly efficient transformation method for the yeast *Saccharomyces cerevisiae* using glutathione and early log phase cells," Journal of Bioscience and Bioengineering, 2002, vol. 94, Iss. 2, pp. 166-171. (Abstract only).
International Search Report and Written Opinion for International (PCT) Patent Application No. PCT/US2014/031183, dated Aug. 28, 2014 13 pages.
International Preliminary Report on Patentability for International (PCT) Patent Application No. PCT/US2014/031183 dated Oct. 1, 2015, 9 pages.
Hamilton et al., "High levels of expression of the transcription factor Brachyury induce resistance of human carcinoma cells to immune-mediated attack," Journal for ImmunoTherapy of Cancer, 2013, vol. 1, Suppl. 1, p. P152.
Heery et al., "Phase I Trial of a Yeast-Based Therapeutic Cancer Vaccine (GI-6301) Targeting the Transcription Factor Brachyury," Cancer Immunology Research, 2015, vol. 3, Iss. 11, pp. 1248-1256.
Hsu et al., "Generation of chordoma cell line JHC7 and the identification of Brachyury as a novel molecular target: Laboratory investigation," Journal of Neurosurgery, 2011, vol. 115, No. 4, pp. 760-769.
Palena et al., "Brachyury, a driver of tumor invasiveness and resistance to multiple therapies, is a novel immunotherapy target," Journal for ImmunoTherapy of Cancer, 2013, vol. 1, Suppl. 1, p. P230.
Palena et al., "Chapter Two—Immune Targeting of Tumor Epithelial-Mesenchymal Transition via Brachyury-Based Vaccines," Advances in Cancer Research, 2015, vol. 128, pp. 69-93.
Romeo et al., "Brachyury and chordoma: the chondroid-chordoid dilemma resolved?," The Journal of Pathology, 2006, vol. 209, Iss. 2, pp. 143-146.
Schwab et al., "Chordoma and chondrosarcoma gene profile: implications for immunotherapy," Cancer Immunology, Immunotherapy, 2009, vol. 58, Iss. 3, pp. 339-349.
Stirnimann et al., "Structural Basis of TBX5—DNA Recognition: The T-Box Domain in Its DNA-Bound and -Unbound Form," Journal of Molecular Biology, 2010, vol. 400, Iss. 1, pp. 71-81.
Tsang et al., "The generation and analysis of a novel combination of recombinant adenovirus vaccines targeting three tumor antigens as an immunotherapeutic," Journal for ImmunoTherapy of Cancer, 2015, vol. 3, Suppl. 2, p. P452.
Tucker et al., "Identification and characterization of a cytotoxic T-lymphocyte agonist epitope of brachyury, a transcription factor involved in epithelial to mesenchymal transition and metastasis," Cancer Immunology, Immunotherapy, 2014, vol. 63, Iss. 12, pp. 1307-1317.
Extended European Search Report for European Patent Application No. 14797995.9 dated Sep. 16, 2016, 9 pages.

\* cited by examiner

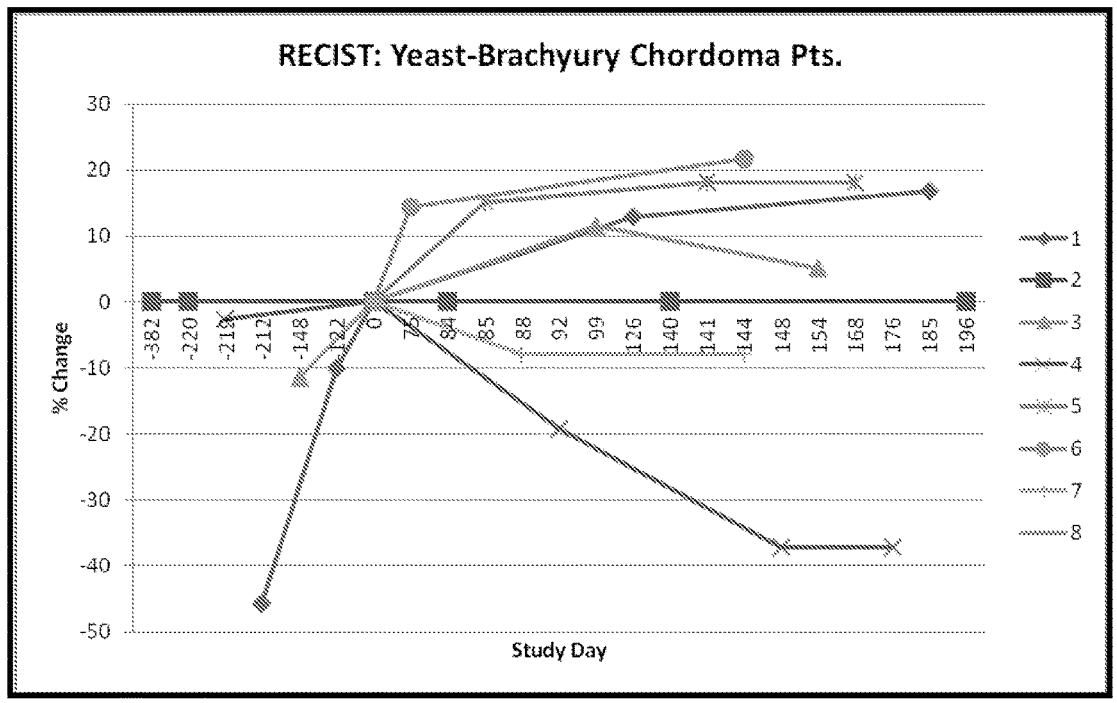

SEQUENCE LISTING

<160> NUMBER OF SEQ ID NOS: 20

<210> SEQ ID NO 1
<211> LENGTH: 2518
<212> TYPE: DNA
<213> ORGANISM: Homo sapiens
<220> FEATURE:
<221> NAME/KEY: CDS
<222> LOCATION: (494)..(1801)

<400> SEQUENCE: 1

```
tttgcttttg cttatttccg tccatttccc tctctgcgcg cggaccttcc ttttccagat      60
ggtgagagcc gcggggacac ccgacgccgg ggcaggctga tccacgatcc tgggtgtgcg     120
taacgccgcc tggggctccg tgggcgaggg acgtgtgggg acaggtgcac cggaaactgc     180
cagactggag agttgaggca tcggaggcgc gagaacagca ctactactgc ggcgagacga     240
gcgcggcgca tcccaaagcc cggccaaatg cgctcgtccc tgggagggga gggaggcgcg     300
cctggagcgg ggacagtctt ggtccgcgcc ctcctcccgg gtctgtgccg ggacccggga     360
cccgggagcc gtcgcaggtc tcggtccaag gggccccttt tctcggaagg gcggcggcca     420
agagcaggga aggtggatct caggtagcga gtctgggctt cggggacggc ggggagggga     480
gccggacggg agg atg agc tcc cct ggc acc gag agc gcg gga aag agc        529
            Met Ser Ser Pro Gly Thr Glu Ser Ala Gly Lys Ser
              1               5                  10 ctg cag tac cga gtg gac cac ctg ctg agc gcc gtg gag aat gag ctg       577
Leu Gln Tyr Arg Val Asp His Leu Leu Ser Ala Val Glu Asn Glu Leu
         15                  20                  25 cag gcg ggc agc gag aag ggc gac ccc aca gag cgc gaa ctg cgc gtg       625
Gln Ala Gly Ser Glu Lys Gly Asp Pro Thr Glu Arg Glu Leu Arg Val
 30                  35                  40 ggc ctg gag gag agc gag ctg tgg ctg cgc ttc aag gag ctc acc aat       673
Gly Leu Glu Glu Ser Glu Leu Trp Leu Arg Phe Lys Glu Leu Thr Asn
 45                  50                  55                  60 gag atg atc gtg acc aag aac ggc agg agg atg ttt ccg gtg ctg aag       721
Glu Met Ile Val Thr Lys Asn Gly Arg Arg Met Phe Pro Val Leu Lys
                 65                  70                  75 gtg aac gtg tct ggc ctg gac ccc aac gcc atg tac tcc ttc ctg ctg       769
Val Asn Val Ser Gly Leu Asp Pro Asn Ala Met Tyr Ser Phe Leu Leu
             80                  85                  90 gac ttc gtg gcg gcg gac aac cac cgc tgg aag tac gtg aac ggg gaa       817
Asp Phe Val Ala Ala Asp Asn His Arg Trp Lys Tyr Val Asn Gly Glu
         95                 100                 105 tgg gtg ccg ggg ggc aag ccg gag ccg cag gcg ccc agc tgc gtc tac       865
Trp Val Pro Gly Gly Lys Pro Glu Pro Gln Ala Pro Ser Cys Val Tyr
     110                 115                 120 atc cac ccc gac tcg ccc aac ttc ggg gcc cac tgg atg aag gct ccc       913
Ile His Pro Asp Ser Pro Asn Phe Gly Ala His Trp Met Lys Ala Pro
125                 130                 135                 140 gtc tcc ttc agc aaa gtc aag ctc acc aac aag ctc aac gga ggg ggc       961
Val Ser Phe Ser Lys Val Lys Leu Thr Asn Lys Leu Asn Gly Gly Gly
                145                 150                 155 cag atc atg ctg aac tcc ttg cat aag tat gag cct cga atc cac ata      1009
Gln Ile Met Leu Asn Ser Leu His Lys Tyr Glu Pro Arg Ile His Ile
            160                 165                 170 gtg aga gtt ggg ggt cca cag cgc atg atc acc agc cac tgc ttc cct      1057
Val Arg Val Gly Gly Pro Gln Arg Met Ile Thr Ser His Cys Phe Pro
        175                 180                 185 gag acc cag ttc ata gcg gtg act gct tat cag aac gag gag atc aca      1105
Glu Thr Gln Phe Ile Ala Val Thr Ala Tyr Gln Asn Glu Glu Ile Thr
```

```
              190                 195                 200
gct ctt aaa att aag tac aat cca ttt gca aaa gct ttc ctt gat gca      1153
Ala Leu Lys Ile Lys Tyr Asn Pro Phe Ala Lys Ala Phe Leu Asp Ala
205                 210                 215                 220 aag gaa aga agt gat cac aaa gag atg atg gag gaa ccc gga gac agc      1201
Lys Glu Arg Ser Asp His Lys Glu Met Met Glu Glu Pro Gly Asp Ser
                225                 230                 235 cag caa cct ggg tac tcc caa tgg ggg tgg ctt ctt cct gga acc agc      1249
Gln Gln Pro Gly Tyr Ser Gln Trp Gly Trp Leu Leu Pro Gly Thr Ser
            240                 245                 250 acc ctg tgt cca cct gca aat cct cat cct cag ttt gga ggt gcc ctc      1297
Thr Leu Cys Pro Pro Ala Asn Pro His Pro Gln Phe Gly Gly Ala Leu
        255                 260                 265 tcc ctc ccc tcc acg cac agc tgt gac agg tac cca acc ctg agg agc      1345
Ser Leu Pro Ser Thr His Ser Cys Asp Arg Tyr Pro Thr Leu Arg Ser
    270                 275                 280 cac cgg tcc tca ccc tac ccc agc ccc tat gct cat cgg aac aat tct      1393
His Arg Ser Ser Pro Tyr Pro Ser Pro Tyr Ala His Arg Asn Asn Ser
285                 290                 295                 300 cca acc tat tct gac aac tca cct gca tgt tta tcc atg ctg caa tcc      1441
Pro Thr Tyr Ser Asp Asn Ser Pro Ala Cys Leu Ser Met Leu Gln Ser
                305                 310                 315 cat gac aat tgg tcc agc ctt gga atg cct gcc cat ccc agc atg ctc      1489
His Asp Asn Trp Ser Ser Leu Gly Met Pro Ala His Pro Ser Met Leu
            320                 325                 330 ccc gtg agc cac aat gcc agc cca cct acc agc tcc agt cag tac ccc      1537
Pro Val Ser His Asn Ala Ser Pro Pro Thr Ser Ser Ser Gln Tyr Pro
        335                 340                 345 agc ctg tgg tct gtg agc aac ggc gcc gtc acc ccg ggc tcc cag gca      1585
Ser Leu Trp Ser Val Ser Asn Gly Ala Val Thr Pro Gly Ser Gln Ala
    350                 355                 360 gca gcc gtg tcc aac ggg ctg ggg gcc cag ttc ttc cgg ggc tcc ccc      1633
Ala Ala Val Ser Asn Gly Leu Gly Ala Gln Phe Phe Arg Gly Ser Pro
365                 370                 375                 380 gcg cac tac aca ccc ctc acc cat ccg gtc tcg gcg ccc tct tcc tcg      1681
Ala His Tyr Thr Pro Leu Thr His Pro Val Ser Ala Pro Ser Ser Ser
                385                 390                 395 gga tcc cca ctg tac gaa ggg gcg gcc gcg gcc aca gac atc gtg gac      1729
Gly Ser Pro Leu Tyr Glu Gly Ala Ala Ala Ala Thr Asp Ile Val Asp
            400                 405                 410 agc cag tac gac gcc gca gcc caa ggc cgc ctc ata gcc tca tgg aca      1777
Ser Gln Tyr Asp Ala Ala Ala Gln Gly Arg Leu Ile Ala Ser Trp Thr
        415                 420                 425 cct gtg tcg cca cct tcc atg tga agcagcaagg cccaggtccc gaaagatgca     1831
Pro Val Ser Pro Pro Ser Met
430                 435 gtgactttt  gtcgtggcag  ccagtggtga  ctggattgac  ctactaggta  cccagtggca   1891
gtctcaggtt  aagaaggaaa  tgcagcctca  gtaacttcct  tttcaaagca  gtggaggagc   1951
acacggcacc  tttccccaga  gccccagcat  cccttgctca  cacctgcagt  agcggtgctg   2011
tcccaggtgg  cttacagatg  aacccaactg  tggagatgat  gcagttggcc  caacctcact   2071
gacggtgaaa  aaatgtttgc  cagggtccag  aaactttttt  tggtttattt  ctcatacagt   2131
gtattggcaa  ctttggcaca  ccagaatttg  taaactccac  cagtcctact  ttagtgagat   2191
aaaaagcaca  ctcttaatct  tcttccttgt  tgctttcaag  tagttagagt  tgagctgtta   2251
aggacagaat  aaaatcatag  ttgaggacag  caggttttag  ttgaattgaa  atttgactg    2311 ctctgccccc  tagaatgtgt  gtattttaag  catatgtagc  taatctcttg  tgttgttaaa   2371
```

```
ctataactgt tcatattttt tcttttgaca aagtagccaa agacaatcag cagaaagcat    2431
tttctgcaaa ataaacgcaa tatgcaaaat gtgattcgtc cagttattag tgaagcccct    2491 cctttttgtga gtatttactg tttattg                                       2518
```

<210> SEQ ID NO 2
<211> LENGTH: 435
<212> TYPE: PRT
<213> ORGANISM: Homo sapiens

<400> SEQUENCE: 2

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335

Asn Ala Ser Pro Pro Thr Ser Ser Ser Gln Tyr Pro Ser Leu Trp Ser
```

```
                        340                 345                 350
Val Ser Asn Gly Ala Val Thr Pro Gly Ser Gln Ala Ala Val Ser
                355                 360                 365

Asn Gly Leu Gly Ala Gln Phe Phe Arg Gly Ser Pro Ala His Tyr Thr
        370                 375                 380

Pro Leu Thr His Pro Val Ser Ala Pro Ser Ser Gly Ser Pro Leu
385                 390                 395                 400

Tyr Glu Gly Ala Ala Ala Thr Asp Ile Val Asp Ser Gln Tyr Asp
                405                 410                 415

Ala Ala Ala Gln Gly Arg Leu Ile Ala Ser Trp Thr Pro Val Ser Pro
                420                 425                 430

Pro Ser Met
        435

<210> SEQ ID NO 3
<211> LENGTH: 2046
<212> TYPE: DNA
<213> ORGANISM: Mus musculus
<220> FEATURE:
<221> NAME/KEY: CDS
<222> LOCATION: (109)..(1419)

<400> SEQUENCE: 3
ggctccgcag agtgacccctt tttcttggaa aagcggtggc gagagaagtg aaggtggctg         60 tgggtaggg agtcaagact cctggaaggt ggagagggtg gcgggagg atg agc tcg         117
                                                    Met Ser Ser
                                                     1 ccg ggc aca gag agc gca ggg aag agc ctg cag tac cga gtg gac cac        165
Pro Gly Thr Glu Ser Ala Gly Lys Ser Leu Gln Tyr Arg Val Asp His
    5                   10                  15 ctg ctc agc gcc gtg gag agc gag ctg cag gcg ggc agc gag aag gga        213
Leu Leu Ser Ala Val Glu Ser Glu Leu Gln Ala Gly Ser Glu Lys Gly
 20                  25                  30                  35 gac ccc acc gaa cgc gaa ctg cga gtg ggc ctg gag gag agc gag ctg        261
Asp Pro Thr Glu Arg Glu Leu Arg Val Gly Leu Glu Glu Ser Glu Leu
                40                  45                  50 tgg ctg cgc ttc aag gag cta act aac gag atg att gtg acc aag aac        309
Trp Leu Arg Phe Lys Glu Leu Thr Asn Glu Met Ile Val Thr Lys Asn
             55                  60                  65 ggc agg agg atg ttc ccg gtg ctg aag gta aat gtg tca ggc ctg gac        357
Gly Arg Arg Met Phe Pro Val Leu Lys Val Asn Val Ser Gly Leu Asp
         70                  75                  80 ccc aat gcc atg tac tct ttc ttg ctg gac ttc gtg acg gct gac aac        405
Pro Asn Ala Met Tyr Ser Phe Leu Leu Asp Phe Val Thr Ala Asp Asn
 85                  90                  95 cac cgc tgg aaa tat gtg aac ggg gag tgg gta cct ggg ggc aaa cca        453
His Arg Trp Lys Tyr Val Asn Gly Glu Trp Val Pro Gly Gly Lys Pro
100                 105                 110                 115 gag cct cag gcg ccc agc tgc gtc tac atc cac cca gac tcg ccc aat        501
Glu Pro Gln Ala Pro Ser Cys Val Tyr Ile His Pro Asp Ser Pro Asn
                120                 125                 130 ttt ggg gcc cac tgg atg aag gcg cct gtg tct ttc agc aaa gtc aaa        549
Phe Gly Ala His Trp Met Lys Ala Pro Val Ser Phe Ser Lys Val Lys
            135                 140                 145 ctc acc aac aag ctc aat gga ggg gga cag atc atg tta aac tcc ttg        597
Leu Thr Asn Lys Leu Asn Gly Gly Gly Gln Ile Met Leu Asn Ser Leu
        150                 155                 160 cat aag tat gaa cct cgg att cac atc gtg aga gtt ggg ggc ccg caa        645
His Lys Tyr Glu Pro Arg Ile His Ile Val Arg Val Gly Gly Pro Gln
```

```
              165                 170                 175
cgc atg atc acc agc cac tgc ttt ccc gag acc cag ttc ata gct gtg    693
Arg Met Ile Thr Ser His Cys Phe Pro Glu Thr Gln Phe Ile Ala Val
180                 185                 190                 195 act gcc tac cag aat gag gag att aca gcc ctt aaa att aaa tac aac    741
Thr Ala Tyr Gln Asn Glu Glu Ile Thr Ala Leu Lys Ile Lys Tyr Asn
                200                 205                 210 cca ttt gct aaa gcc ttc ctt gat gcc aaa gaa aga aac gac cac aaa    789
Pro Phe Ala Lys Ala Phe Leu Asp Ala Lys Glu Arg Asn Asp His Lys
            215                 220                 225 gat gta atg gag gaa ccg ggg gac tgc cag cag ccg ggg tat tcc caa    837
Asp Val Met Glu Glu Pro Gly Asp Cys Gln Gln Pro Gly Tyr Ser Gln
        230                 235                 240 tgg ggg tgg ctt gtt cct ggt gct ggc acc ctc tgc ccg cct gcc agc    885
Trp Gly Trp Leu Val Pro Gly Ala Gly Thr Leu Cys Pro Pro Ala Ser
    245                 250                 255 tcc cac cct cag ttt gga ggc tcg ctc tct ctc ccc tcc aca cac ggc    933
Ser His Pro Gln Phe Gly Gly Ser Leu Ser Leu Pro Ser Thr His Gly
260                 265                 270                 275 tgt gag agg tac cca gct cta agg aac cac cgg tca tcg ccc tac ccc    981
Cys Glu Arg Tyr Pro Ala Leu Arg Asn His Arg Ser Ser Pro Tyr Pro
                280                 285                 290 agc ccc tat gct cat cgg aac agc tct cca acc tat gcg gac aat tca   1029
Ser Pro Tyr Ala His Arg Asn Ser Ser Pro Thr Tyr Ala Asp Asn Ser
            295                 300                 305 tct gct tgt ctg tcc atg ctg cag tcc cat gat aac tgg tct agc ctc   1077
Ser Ala Cys Leu Ser Met Leu Gln Ser His Asp Asn Trp Ser Ser Leu
        310                 315                 320 gga gtg cct ggc cac acc agc atg ctg cct gtg agt cat aac gcc agc   1125
Gly Val Pro Gly His Thr Ser Met Leu Pro Val Ser His Asn Ala Ser
    325                 330                 335 cca cct act ggc tct agc cag tat ccc agt ctc tgg tct gtg agc aat   1173
Pro Pro Thr Gly Ser Ser Gln Tyr Pro Ser Leu Trp Ser Val Ser Asn
340                 345                 350                 355 ggt acc atc acc cca ggc tcc cag aca gct ggg gtg tcc aac ggg ctg   1221
Gly Thr Ile Thr Pro Gly Ser Gln Thr Ala Gly Val Ser Asn Gly Leu
                360                 365                 370 gga gct cag ttc ttt cga ggc tcc cct gca cat tac aca cca ctg acg   1269
Gly Ala Gln Phe Phe Arg Gly Ser Pro Ala His Tyr Thr Pro Leu Thr
            375                 380                 385 cac acg gtc tca gct gcc acg tcc tcg tct tct ggt tct ccg atg tat   1317
His Thr Val Ser Ala Ala Thr Ser Ser Ser Ser Gly Ser Pro Met Tyr
        390                 395                 400 gaa ggg gct gct aca gtc aca gac att tct gac agc cag tat gac acg   1365
Glu Gly Ala Ala Thr Val Thr Asp Ile Ser Asp Ser Gln Tyr Asp Thr
    405                 410                 415 gcc caa agc ctc ctc ata gcc tcg tgg aca cct gtg tca ccc cca tct   1413
Ala Gln Ser Leu Leu Ile Ala Ser Trp Thr Pro Val Ser Pro Pro Ser
420                 425                 430                 435 atg tga attgaacttt cctccatgtg ctgagacttg taacaaccgg tgtcaactgg    1469
Met atcttctagg ctcaaagtgg caggctcttg ggacaaggga aaaataaata aataaaagct   1529
agatactaac aactccattt tcaaataaga gcaataatac atgtcctata atcatgttct   1589
acagcctctt gtttgatacc tacagtagtg atatgtgtcc tacattatga agccaaggac   1649
agagagacgg ctgtggtcca gttttttgtg actggcagtt aatcagagtc ctttgctagg   1709
tagggtccta tatcttgtgt ttctctacaa catatatgtg actttgaaat cctggaattc   1769
```

```
gtccacccce tgtcctactt tagtgagaca caaggtacac ctctaatgtc ctcccttgtt   1829
gccttagagt agttaacttt gaggacagaa aaaagcatag ccagaagatt gtaactgaac   1889
cgtcaactgt tctgcccttg aacatgcct  actttaagca cacgtagctt tttgtgttgg   1949
gaagtcaact gtatggatac ttttctgttg acaaagtagc caaagacaat ctgcagaaag   2009
tgttttctgc acaataaagg caatatatag cacctgg                           2046
```

<210> SEQ ID NO 4
<211> LENGTH: 436
<212> TYPE: PRT
<213> ORGANISM: Mus musculus

<400> SEQUENCE: 4

```
Met Ser Ser Pro Gly Thr Glu Ser Ala Gly Lys Ser Leu Gln Tyr Arg
1               5                   10                  15

Val Asp His Leu Leu Ser Ala Val Glu Ser Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Thr
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Asn
    210                 215                 220

Asp His Lys Asp Val Met Glu Glu Pro Gly Asp Cys Gln Gln Pro Gly
225                 230                 235                 240

Tyr Ser Gln Trp Gly Trp Leu Val Pro Gly Ala Gly Thr Leu Cys Pro
                245                 250                 255

Pro Ala Ser Ser His Pro Gln Phe Gly Gly Ser Leu Ser Leu Pro Ser
            260                 265                 270

Thr His Gly Cys Glu Arg Tyr Pro Ala Leu Arg Asn His Arg Ser Ser
        275                 280                 285

Pro Tyr Pro Ser Pro Tyr Ala His Arg Asn Ser Ser Pro Thr Tyr Ala
    290                 295                 300

Asp Asn Ser Ser Ala Cys Leu Ser Met Leu Gln Ser His Asp Asn Trp
305                 310                 315                 320

Ser Ser Leu Gly Val Pro Gly His Thr Ser Met Leu Pro Val Ser His
```

```
                    325                 330                 335
Asn Ala Ser Pro Pro Thr Gly Ser Ser Gln Tyr Pro Ser Leu Trp Ser
            340                 345                 350

Val Ser Asn Gly Thr Ile Thr Pro Gly Ser Gln Thr Ala Gly Val Ser
            355                 360                 365

Asn Gly Leu Gly Ala Gln Phe Phe Arg Gly Ser Pro Ala His Tyr Thr
            370                 375                 380

Pro Leu Thr His Thr Val Ser Ala Ala Thr Ser Ser Ser Ser Gly Ser
385                 390                 395                 400

Pro Met Tyr Glu Gly Ala Ala Thr Val Thr Asp Ile Ser Asp Ser Gln
                405                 410                 415

Tyr Asp Thr Ala Gln Ser Leu Leu Ile Ala Ser Trp Thr Pro Val Ser
            420                 425                 430

Pro Pro Ser Met
            435

<210> SEQ ID NO 5
<211> LENGTH: 1305
<212> TYPE: DNA
<213> ORGANISM: Homo sapiens
<220> FEATURE:
<221> NAME/KEY: CDS
<222> LOCATION: (1)..(1305)

<400> SEQUENCE: 5
```

| | | | | | | | | | | | | | | | | |
|---|---|---|---|---|---|---|---|---|---|---|---|---|---|---|---|---|
| atg | agc | tcc | cct | ggc | acc | gag | agc | gcg | gga | aag | agc | ctg | cag | tac | cga | 48 |
| Met | Ser | Ser | Pro | Gly | Thr | Glu | Ser | Ala | Gly | Lys | Ser | Leu | Gln | Tyr | Arg | |
| 1 | | | | 5 | | | | | 10 | | | | | 15 | | |
| gtg | gac | cac | ctg | ctg | agc | gcc | gtg | gag | aat | gag | ctg | cag | gcg | ggc | agc | 96 |
| Val | Asp | His | Leu | Leu | Ser | Ala | Val | Glu | Asn | Glu | Leu | Gln | Ala | Gly | Ser | |
| | | | | 20 | | | | | 25 | | | | | 30 | | |
| gag | aag | ggc | gac | ccc | aca | gag | cgc | gaa | ctg | cgc | gtg | ggc | ctg | gag | gag | 144 |
| Glu | Lys | Gly | Asp | Pro | Thr | Glu | Arg | Glu | Leu | Arg | Val | Gly | Leu | Glu | Glu | |
| | | 35 | | | | | 40 | | | | | 45 | | | | |
| agc | gag | ctg | tgg | ctg | cgc | ttc | aag | gag | ctc | acc | aat | gag | atg | atc | gtg | 192 |
| Ser | Glu | Leu | Trp | Leu | Arg | Phe | Lys | Glu | Leu | Thr | Asn | Glu | Met | Ile | Val | |
| | 50 | | | | | 55 | | | | | 60 | | | | | |
| acc | aag | aac | ggc | agg | agg | atg | ttt | ccg | gtg | ctg | aag | gtg | aac | gtg | tct | 240 |
| Thr | Lys | Asn | Gly | Arg | Arg | Met | Phe | Pro | Val | Leu | Lys | Val | Asn | Val | Ser | |
| 65 | | | | | 70 | | | | | 75 | | | | | 80 | |
| ggc | ctg | gac | ccc | aac | gcc | atg | tac | tcc | ttc | ctg | ctg | gac | ttc | gtg | gcg | 288 |
| Gly | Leu | Asp | Pro | Asn | Ala | Met | Tyr | Ser | Phe | Leu | Leu | Asp | Phe | Val | Ala | |
| | | | | 85 | | | | | 90 | | | | | 95 | | |
| gcg | gac | aac | cac | cgc | tgg | aag | tac | gtg | aac | ggg | gaa | tgg | gtg | ccg | ggg | 336 |
| Ala | Asp | Asn | His | Arg | Trp | Lys | Tyr | Val | Asn | Gly | Glu | Trp | Val | Pro | Gly | |
| | | | 100 | | | | | 105 | | | | | 110 | | | |
| ggc | aag | ccg | gag | ccg | cag | gcg | ccc | agc | tgc | gtc | tac | atc | cac | ccc | gac | 384 |
| Gly | Lys | Pro | Glu | Pro | Gln | Ala | Pro | Ser | Cys | Val | Tyr | Ile | His | Pro | Asp | |
| | | 115 | | | | | 120 | | | | | 125 | | | | |
| tcg | ccc | aac | ttc | ggg | gcc | cac | tgg | atg | aag | gct | ccc | gtc | tcc | ttc | agc | 432 |
| Ser | Pro | Asn | Phe | Gly | Ala | His | Trp | Met | Lys | Ala | Pro | Val | Ser | Phe | Ser | |
| | 130 | | | | | 135 | | | | | 140 | | | | | |
| aaa | gtc | aag | ctc | acc | aac | aag | ctc | aac | gga | ggg | ggc | cag | atc | atg | ctg | 480 |
| Lys | Val | Lys | Leu | Thr | Asn | Lys | Leu | Asn | Gly | Gly | Gly | Gln | Ile | Met | Leu | |
| 145 | | | | | 150 | | | | | 155 | | | | | 160 | |
| aac | tcc | ttg | cat | aag | tat | gag | cct | cga | atc | cac | ata | gtg | aga | gtt | ggg | 528 |
| Asn | Ser | Leu | His | Lys | Tyr | Glu | Pro | Arg | Ile | His | Ile | Val | Arg | Val | Gly | |
| | | | | 165 | | | | | 170 | | | | | 175 | | |
| gat | cca | cag | cgc | atg | atc | acc | agc | cac | tgc | ttc | cct | gag | acc | cag | ttc | 576 |

```
                Asp Pro Gln Arg Met Ile Thr Ser His Cys Phe Pro Glu Thr Gln Phe
                            180                 185                 190 ata gcg gtg act gct tat cag aac gag gag atc aca gct ctt aaa att         624
Ile Ala Val Thr Ala Tyr Gln Asn Glu Glu Ile Thr Ala Leu Lys Ile
            195                 200                 205 aag tac aat cca ttt gca aaa gct ttc ctt gat gca aag gaa aga agt         672
Lys Tyr Asn Pro Phe Ala Lys Ala Phe Leu Asp Ala Lys Glu Arg Ser
        210                 215                 220 gat cac aaa gag atg atg gag gaa ccc gga gac agc cag caa cct ggg         720
Asp His Lys Glu Met Met Glu Glu Pro Gly Asp Ser Gln Gln Pro Gly
225                 230                 235                 240 tac tcc caa tgg ggg tgg ctt ctt cct gga acc agc acc ctg tgt cca         768
Tyr Ser Gln Trp Gly Trp Leu Leu Pro Gly Thr Ser Thr Leu Cys Pro
                245                 250                 255 cct gca aat cct cat cct cag ttt gga ggt gcc ctc tcc ctc ccc tcc         816
Pro Ala Asn Pro His Pro Gln Phe Gly Gly Ala Leu Ser Leu Pro Ser
            260                 265                 270 acg cac agc tgt gac agg tac cca acc ctg agg agc cac cgg tcc tca         864
Thr His Ser Cys Asp Arg Tyr Pro Thr Leu Arg Ser His Arg Ser Ser
        275                 280                 285 ccc tac ccc agc ccc tat gct cat cgg aac aat tct cca acc tat tct         912
Pro Tyr Pro Ser Pro Tyr Ala His Arg Asn Asn Ser Pro Thr Tyr Ser
290                 295                 300 gac aac tca cct gca tgt tta tcc atg ctg caa tcc cat gac aat tgg         960
Asp Asn Ser Pro Ala Cys Leu Ser Met Leu Gln Ser His Asp Asn Trp
305                 310                 315                 320 tcc agc ctt gga atg cct gcc cat ccc agc atg ctc ccc gtg agc cac        1008
Ser Ser Leu Gly Met Pro Ala His Pro Ser Met Leu Pro Val Ser His
                325                 330                 335 aat gcc agc cca cct acc agc tcc agt cag tac ccc agc ctg tgg tct        1056
Asn Ala Ser Pro Pro Thr Ser Ser Ser Gln Tyr Pro Ser Leu Trp Ser
            340                 345                 350 gtg agc aac ggc gcc gtc acc ccg ggc tcc cag gca gca gcc gtg acc        1104
Val Ser Asn Gly Ala Val Thr Pro Gly Ser Gln Ala Ala Ala Val Thr
        355                 360                 365 aac ggg ctg ggg gcc cag ttc ttc cgg ggc tcc ccc gcg cac tac aca        1152
Asn Gly Leu Gly Ala Gln Phe Phe Arg Gly Ser Pro Ala His Tyr Thr
370                 375                 380 ccc ctc acc cat ccg gtc tcg gca ccc tct tcc tcg gga tcc cca ctg        1200
Pro Leu Thr His Pro Val Ser Ala Pro Ser Ser Ser Gly Ser Pro Leu
385                 390                 395                 400 tac gaa ggg gcg gcc gcg gcc aca aac atc gtg gac agc cag tac gac        1248
Tyr Glu Gly Ala Ala Ala Ala Thr Asn Ile Val Asp Ser Gln Tyr Asp
                405                 410                 415 gcc gca gcc caa ggc cgc ctc ata gcc tca tgg aca cct gtg tcg cca        1296
Ala Ala Ala Gln Gly Arg Leu Ile Ala Ser Trp Thr Pro Val Ser Pro
            420                 425                 430 cct tcc atg                                                            1305
Pro Ser Met
        435

<210> SEQ ID NO 6
<211> LENGTH: 435
<212> TYPE: PRT
<213> ORGANISM: Homo sapiens

<400> SEQUENCE: 6

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
```

-continued

```
                20                  25                  30
Glu Lys Gly Asp Pro Thr Glu Arg Glu Leu Arg Val Gly Leu Glu Glu
            35                  40                  45

Ser Glu Leu Trp Leu Arg Phe Lys Glu Leu Thr Asn Glu Met Ile Val
 50                  55                  60

Thr Lys Asn Gly Arg Arg Met Phe Pro Val Leu Lys Val Asn Val Ser
 65                  70                  75                  80

Gly Leu Asp Pro Asn Ala Met Tyr Ser Phe Leu Leu Asp Phe Val Ala
            85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
            115                 120                 125

Ser Pro Asn Phe Gly Ala His Trp Met Lys Ala Pro Val Ser Phe Ser
            130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
            165                 170                 175

Asp Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
            195                 200                 205

Lys Tyr Asn Pro Phe Ala Lys Ala Phe Leu Asp Ala Lys Glu Arg Ser
            210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Leu Cys Pro
            245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
            275                 280                 285

Pro Tyr Pro Ser Pro Tyr Ala His Arg Asn Asn Ser Pro Thr Tyr Ser
            290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
            325                 330                 335

Asn Ala Ser Pro Pro Thr Ser Ser Gln Tyr Pro Ser Leu Trp Ser
            340                 345                 350

Val Ser Asn Gly Ala Val Thr Pro Gly Ser Gln Ala Ala Val Thr
            355                 360                 365

Asn Gly Leu Gly Ala Gln Phe Phe Arg Gly Ser Pro Ala His Tyr Thr
            370                 375                 380

Pro Leu Thr His Pro Val Ser Ala Pro Ser Ser Ser Gly Ser Pro Leu
385                 390                 395                 400

Tyr Glu Gly Ala Ala Ala Thr Asn Ile Val Asp Ser Gln Tyr Asp
            405                 410                 415

Ala Ala Ala Gln Gly Arg Leu Ile Ala Ser Trp Thr Pro Val Ser Pro
            420                 425                 430

Pro Ser Met
        435
```

```
<210> SEQ ID NO 7
<211> LENGTH: 1357
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (10)..(1347)

<400> SEQUENCE: 7 gaattccgc atg gcc gat gaa gct ccg agc tcc cct ggc acc gag agc gcg      51
         Met Ala Asp Glu Ala Pro Ser Ser Pro Gly Thr Glu Ser Ala
         1               5                   10 gga aag agc ctg cag tac cga gtg gac cac ctg ctg agc gcc gtg gag        99
Gly Lys Ser Leu Gln Tyr Arg Val Asp His Leu Leu Ser Ala Val Glu
15                  20                  25                  30 aat gag ctg cag gcg ggc agc gag aag ggc gac ccc aca gag cgc gaa       147
Asn Glu Leu Gln Ala Gly Ser Glu Lys Gly Asp Pro Thr Glu Arg Glu
                35                  40                  45 ctg cgc gtg ggc ctg gag gag agc gag ctg tgg ctg cgc ttc aag gag       195
Leu Arg Val Gly Leu Glu Glu Ser Glu Leu Trp Leu Arg Phe Lys Glu
            50                  55                  60 ctc acc aat gag atg atc gtg acc aag aac ggc agg agg atg ttt ccg       243
Leu Thr Asn Glu Met Ile Val Thr Lys Asn Gly Arg Arg Met Phe Pro
65                  70                  75 gtg ctg aag gtg aac gtg tct ggc ctg gac ccc aac gcc atg tac tcc       291
Val Leu Lys Val Asn Val Ser Gly Leu Asp Pro Asn Ala Met Tyr Ser
            80                  85                  90 ttc ctg ctg gac ttc gtg gcg gcg gac aac cac cgc tgg aag tac gtg       339
Phe Leu Leu Asp Phe Val Ala Ala Asp Asn His Arg Trp Lys Tyr Val
95                  100                 105                 110 aac ggg gaa tgg gtg ccg ggg ggc aag ccg gag ccg cag gcg ccc agc       387
Asn Gly Glu Trp Val Pro Gly Gly Lys Pro Glu Pro Gln Ala Pro Ser
                115                 120                 125 tgc gtc tac atc cac ccc gac tcg ccc aac ttc ggg gcc cac tgg atg       435
Cys Val Tyr Ile His Pro Asp Ser Pro Asn Phe Gly Ala His Trp Met
            130                 135                 140 aag gct ccc gtc tcc ttc agc aaa gtc aag ctc acc aac aag ctc aac       483
Lys Ala Pro Val Ser Phe Ser Lys Val Lys Leu Thr Asn Lys Leu Asn
145                 150                 155 gga ggg ggc cag atc atg ctg aac tcc ttg cat aag tat gag cct cga       531
Gly Gly Gly Gln Ile Met Leu Asn Ser Leu His Lys Tyr Glu Pro Arg
            160                 165                 170 atc cac ata gtg aga gtt ggg gat cca cag cgc atg atc acc agc cac       579
Ile His Ile Val Arg Val Gly Asp Pro Gln Arg Met Ile Thr Ser His
175                 180                 185                 190 tgc ttc cct gag acc cag ttc ata gcg gtg act gct tat cag aac gag       627
Cys Phe Pro Glu Thr Gln Phe Ile Ala Val Thr Ala Tyr Gln Asn Glu
                195                 200                 205 gag atc aca gct ctt aaa att aag tac aat cca ttt gca aaa gct ttc       675
Glu Ile Thr Ala Leu Lys Ile Lys Tyr Asn Pro Phe Ala Lys Ala Phe
            210                 215                 220 ctt gat gca aag gaa aga agt gat cac aaa gag atg atg gag gaa ccc       723
Leu Asp Ala Lys Glu Arg Ser Asp His Lys Glu Met Met Glu Glu Pro
225                 230                 235 gga gac agc cag caa cct ggg tac tcc caa tgg ggg tgg ctt ctt cct       771
Gly Asp Ser Gln Gln Pro Gly Tyr Ser Gln Trp Gly Trp Leu Leu Pro
            240                 245                 250 gga acc agc acc ctg tgt cca cct gca aat cct cat cct cag ttt gga       819
Gly Thr Ser Thr Leu Cys Pro Pro Ala Asn Pro His Pro Gln Phe Gly
```

```
                                                        -continued

Gly Thr Ser Thr Leu Cys Pro Pro Ala Asn Pro His Pro Gln Phe Gly
255                 260                 265                 270 ggt gcc ctc tcc ctc ccc tcc acg cac agc tgt gac agg tac cca acc      867
Gly Ala Leu Ser Leu Pro Ser Thr His Ser Cys Asp Arg Tyr Pro Thr
                275                 280                 285 ctg agg agc cac cgg tcc tca ccc tac ccc agc cct tat gct cat cgg      915
Leu Arg Ser His Arg Ser Ser Pro Tyr Pro Ser Pro Tyr Ala His Arg
            290                 295                 300 aac aat tct cca acc tat tct gac aac tca cct gca tgt tta tcc atg      963
Asn Asn Ser Pro Thr Tyr Ser Asp Asn Ser Pro Ala Cys Leu Ser Met
        305                 310                 315 ctg caa tcc cat gac aat tgg tcc agc ctt gga atg cct gcc cat ccc     1011
Leu Gln Ser His Asp Asn Trp Ser Ser Leu Gly Met Pro Ala His Pro
    320                 325                 330 agc atg ctc ccc gtg agc cac aat gcc agc cca cct acc agc tcc agt     1059
Ser Met Leu Pro Val Ser His Asn Ala Ser Pro Pro Thr Ser Ser Ser
335                 340                 345                 350 cag tac ccc agc ctg tgg tct gtg agc aac ggc gcc gtc acc ccg ggc     1107
Gln Tyr Pro Ser Leu Trp Ser Val Ser Asn Gly Ala Val Thr Pro Gly
                355                 360                 365 tcc cag gca gca gcc gtg acc aac ggg ctg ggg gcc cag ttc ttc cgg     1155
Ser Gln Ala Ala Ala Val Thr Asn Gly Leu Gly Ala Gln Phe Phe Arg
                370                 375                 380 ggc tcc ccc gcg cac tac aca ccc ctc acc cat ccg gtc tcg gca ccc     1203
Gly Ser Pro Ala His Tyr Thr Pro Leu Thr His Pro Val Ser Ala Pro
            385                 390                 395 tct tcc tcg gga tcc cca ctg tac gaa ggg gcg gcc gcg gcc aca aac     1251
Ser Ser Ser Gly Ser Pro Leu Tyr Glu Gly Ala Ala Ala Ala Thr Asn
        400                 405                 410 atc gtg gac agc cag tac gac gcc gca gcc caa ggc cgc ctc ata gcc     1299
Ile Val Asp Ser Gln Tyr Asp Ala Ala Ala Gln Gly Arg Leu Ile Ala
    415                 420                 425                 430 tca tgg aca cct gtg tcg cca cct tcc atg cat cac cat cac cat cac     1347
Ser Trp Thr Pro Val Ser Pro Pro Ser Met His His His His His His
                435                 440                 445 tgagactagt                                                          1357

<210> SEQ ID NO 8
<211> LENGTH: 446
<212> TYPE: PRT
<213> ORGANISM: Artificial
<220> FEATURE:
<223> OTHER INFORMATION: Synthetic Construct

<400> SEQUENCE: 8

Met Ala Asp Glu Ala Pro Ser Ser Pro Gly Thr Glu Ser Ala Gly Lys
1               5                   10                  15

Ser Leu Gln Tyr Arg Val Asp His Leu Leu Ser Ala Val Glu Asn Glu
                20                  25                  30

Leu Gln Ala Gly Ser Glu Lys Gly Asp Pro Thr Glu Arg Glu Leu Arg
            35                  40                  45

Val Gly Leu Glu Glu Ser Glu Leu Trp Leu Arg Phe Lys Glu Leu Thr
        50                  55                  60

Asn Glu Met Ile Val Thr Lys Asn Gly Arg Arg Met Phe Pro Val Leu
65                  70                  75                  80

Lys Val Asn Val Ser Gly Leu Asp Pro Asn Ala Met Tyr Ser Phe Leu
                85                  90                  95

Leu Asp Phe Val Ala Ala Asp Asn His Arg Trp Lys Tyr Val Asn Gly
            100                 105                 110
```

Glu Trp Val Pro Gly Gly Lys Pro Glu Pro Gln Ala Pro Ser Cys Val
            115                 120                 125

Tyr Ile His Pro Asp Ser Pro Asn Phe Gly Ala His Trp Met Lys Ala
        130                 135                 140

Pro Val Ser Phe Ser Lys Val Lys Leu Thr Asn Lys Leu Asn Gly Gly
145                 150                 155                 160

Gly Gln Ile Met Leu Asn Ser Leu His Lys Tyr Glu Pro Arg Ile His
                165                 170                 175

Ile Val Arg Val Gly Asp Pro Gln Arg Met Ile Thr Ser His Cys Phe
            180                 185                 190

Pro Glu Thr Gln Phe Ile Ala Val Thr Ala Tyr Gln Asn Glu Glu Ile
        195                 200                 205

Thr Ala Leu Lys Ile Lys Tyr Asn Pro Phe Ala Lys Ala Phe Leu Asp
    210                 215                 220

Ala Lys Glu Arg Ser Asp His Lys Glu Met Met Glu Glu Pro Gly Asp
225                 230                 235                 240

Ser Gln Gln Pro Gly Tyr Ser Gln Trp Gly Trp Leu Leu Pro Gly Thr
                245                 250                 255

Ser Thr Leu Cys Pro Pro Ala Asn Pro His Pro Gln Phe Gly Gly Ala
            260                 265                 270

Leu Ser Leu Pro Ser Thr His Ser Cys Asp Arg Tyr Pro Thr Leu Arg
        275                 280                 285

Ser His Arg Ser Ser Pro Tyr Pro Ser Pro Tyr Ala His Arg Asn Asn
    290                 295                 300

Ser Pro Thr Tyr Ser Asp Asn Ser Pro Ala Cys Leu Ser Met Leu Gln
305                 310                 315                 320

Ser His Asp Asn Trp Ser Ser Leu Gly Met Pro Ala His Pro Ser Met
                325                 330                 335

Leu Pro Val Ser His Asn Ala Ser Pro Pro Thr Ser Ser Ser Gln Tyr
            340                 345                 350

Pro Ser Leu Trp Ser Val Ser Asn Gly Ala Val Thr Pro Gly Ser Gln
        355                 360                 365

Ala Ala Ala Val Thr Asn Gly Leu Gly Ala Gln Phe Phe Arg Gly Ser
    370                 375                 380

Pro Ala His Tyr Thr Pro Leu Thr His Pro Val Ser Ala Pro Ser Ser
385                 390                 395                 400

Ser Gly Ser Pro Leu Tyr Glu Gly Ala Ala Ala Thr Asn Ile Val
                405                 410                 415

Asp Ser Gln Tyr Asp Ala Ala Ala Gln Gly Arg Leu Ile Ala Ser Trp
            420                 425                 430

Thr Pro Val Ser Pro Pro Ser Met His His His His His
        435                 440                 445

<210> SEQ ID NO 9
<211> LENGTH: 1360
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (10)..(1353)

<400> SEQUENCE: 9 gaattccgc atg gcc gat gaa gct ccg agc tcg ccg ggc aca gag agc gca    51
          Met Ala Asp Glu Ala Pro Ser Ser Pro Gly Thr Glu Ser Ala

|  |  |  |  |  |  |  |  |  |  |  |  |  |  |  |  |
|---|---|---|---|---|---|---|---|---|---|---|---|---|---|---|---|
| | 1 | | | | 5 | | | | | 10 | | | | | |

```
ggg aag agc ctg cag tac cga gtg gac cac ctg ctc agc gcc gtg gag         99
Gly Lys Ser Leu Gln Tyr Arg Val Asp His Leu Leu Ser Ala Val Glu
 15              20                  25                  30 agc gag ctg cag gcg ggc agc gag aag gga gac ccc acc gaa cgc gaa        147
Ser Glu Leu Gln Ala Gly Ser Glu Lys Gly Asp Pro Thr Glu Arg Glu
                 35                  40                  45 ctg cga gtg ggc ctg gag gag agc gag ctg tgg ctg cgc ttc aag gag        195
Leu Arg Val Gly Leu Glu Glu Ser Glu Leu Trp Leu Arg Phe Lys Glu
             50                  55                  60 cta act aac gag atg att gtg acc aag aac ggc agg agg atg ttc ccg        243
Leu Thr Asn Glu Met Ile Val Thr Lys Asn Gly Arg Arg Met Phe Pro
         65                  70                  75 gtg ctg aag gta aat gtg tca ggc ctg gac ccc aat gcc atg tac tct        291
Val Leu Lys Val Asn Val Ser Gly Leu Asp Pro Asn Ala Met Tyr Ser
     80                  85                  90 ttc ttg ctg gac ttc gtg acg gct gac aac cac cgc tgg aaa tat gtg        339
Phe Leu Leu Asp Phe Val Thr Ala Asp Asn His Arg Trp Lys Tyr Val
 95                 100                 105                 110 aac ggg gag tgg gta cct ggg ggc aaa cca gag cct cag gcg ccc agc        387
Asn Gly Glu Trp Val Pro Gly Gly Lys Pro Glu Pro Gln Ala Pro Ser
                115                 120                 125 tgc gtc tac atc cac cca gac tcg ccc aat ttt ggg gcc cac tgg atg        435
Cys Val Tyr Ile His Pro Asp Ser Pro Asn Phe Gly Ala His Trp Met
            130                 135                 140 aag gcg cct gtg tct ttc agc aaa gtc aaa ctc acc aac aag ctc aat        483
Lys Ala Pro Val Ser Phe Ser Lys Val Lys Leu Thr Asn Lys Leu Asn
        145                 150                 155 gga ggg gga cag atc atg tta aac tcc ttg cat aag tat gaa cct cgg        531
Gly Gly Gly Gln Ile Met Leu Asn Ser Leu His Lys Tyr Glu Pro Arg
    160                 165                 170 att cac atc gtg aga gtt ggg ggc ccg caa cgc atg atc acc agc cac        579
Ile His Ile Val Arg Val Gly Gly Pro Gln Arg Met Ile Thr Ser His
175                 180                 185                 190 tgc ttt ccc gag acc cag ttc ata gct gtg act gcc tac cag aat gag        627
Cys Phe Pro Glu Thr Gln Phe Ile Ala Val Thr Ala Tyr Gln Asn Glu
                195                 200                 205 gag att aca gcc ctt aaa att aaa tac aac cca ttt gct aaa gcc ttc        675
Glu Ile Thr Ala Leu Lys Ile Lys Tyr Asn Pro Phe Ala Lys Ala Phe
            210                 215                 220 ctt gat gcc aaa gaa aga aac gac cac aaa gat gta atg gag gaa ccg        723
Leu Asp Ala Lys Glu Arg Asn Asp His Lys Asp Val Met Glu Glu Pro
        225                 230                 235 ggg gac tgc cag cag ccg ggg tat tcc caa tgg ggg tgg ctt gtt cct        771
Gly Asp Cys Gln Gln Pro Gly Tyr Ser Gln Trp Gly Trp Leu Val Pro
    240                 245                 250 ggt gct ggc acc ctc tgc ccg cct gcc agc tcc cac cct cag ttt gga        819
Gly Ala Gly Thr Leu Cys Pro Pro Ala Ser Ser His Pro Gln Phe Gly
255                 260                 265                 270 ggc tcg ctc tct ctc ccc tcc aca cac ggc tgt gag agg tac cca gct        867
Gly Ser Leu Ser Leu Pro Ser Thr His Gly Cys Glu Arg Tyr Pro Ala
                275                 280                 285 cta agg aac cac cgg tca tcg ccc tac ccc agc ccc tat gct cat cgg        915
Leu Arg Asn His Arg Ser Ser Pro Tyr Pro Ser Pro Tyr Ala His Arg
            290                 295                 300 aac agc tct cca acc tac gcg gac aat tca tct gct tgt ctg tcc atg        963
Asn Ser Ser Pro Thr Tyr Ala Asp Asn Ser Ser Ala Cys Leu Ser Met
        305                 310                 315 ctg cag tcc cat gat aac tgg tct agc ctc gga gtg cct ggc cac acc       1011
```

```
                    Leu Gln Ser His Asp Asn Trp Ser Ser Leu Gly Val Pro Gly His Thr
                        320                 325                 330 agc atg ctg cct gtg agt cat aac gcc agc cca cct act ggc tct agc         1059
Ser Met Leu Pro Val Ser His Asn Ala Ser Pro Pro Thr Gly Ser Ser
335                 340                 345                 350 cag tat ccc agt ctc tgg tct gtg agc aat ggt acc atc acc cca ggc         1107
Gln Tyr Pro Ser Leu Trp Ser Val Ser Asn Gly Thr Ile Thr Pro Gly
                355                 360                 365 tcc cag aca gct ggg gtg tcc aac ggg ctg gga gct cag ttc ttt cga         1155
Ser Gln Thr Ala Gly Val Ser Asn Gly Leu Gly Ala Gln Phe Phe Arg
            370                 375                 380 ggc tcc cct gca cat tac aca cca ctg aca cac acg gtc tca gct gcc         1203
Gly Ser Pro Ala His Tyr Thr Pro Leu Thr His Thr Val Ser Ala Ala
385                 390                 395 acg tcc tcg tct tct ggt tct ccg atg tat gaa ggg gct gct aca gtc         1251
Thr Ser Ser Ser Ser Gly Ser Pro Met Tyr Glu Gly Ala Ala Thr Val
            400                 405                 410 aca gac att tct gac agc cag tat gac acg gcc caa agc ctc ctc ata         1299
Thr Asp Ile Ser Asp Ser Gln Tyr Asp Thr Ala Gln Ser Leu Leu Ile
415                 420                 425                 430 gcc tcg tgg aca cct gtg tca ccc cca tct atg cat cac cat cac cat         1347
Ala Ser Trp Thr Pro Val Ser Pro Pro Ser Met His His His His His
                435                 440                 445 cac tga gactagt                                                         1360
His <210> SEQ ID NO 10
<211> LENGTH: 447
<212> TYPE: PRT
<213> ORGANISM: Artificial
<220> FEATURE:
<223> OTHER INFORMATION: Synthetic Construct

<400> SEQUENCE: 10

Met Ala Asp Glu Ala Pro Ser Ser Pro Gly Thr Glu Ser Ala Gly Lys
1               5                   10                  15

Ser Leu Gln Tyr Arg Val Asp His Leu Leu Ser Ala Val Glu Ser Glu
            20                  25                  30

Leu Gln Ala Gly Ser Glu Lys Gly Asp Pro Thr Glu Arg Glu Leu Arg
        35                  40                  45

Val Gly Leu Glu Glu Ser Glu Leu Trp Leu Arg Phe Lys Glu Leu Thr
    50                  55                  60

Asn Glu Met Ile Val Thr Lys Asn Gly Arg Arg Met Phe Pro Val Leu
65                  70                  75                  80

Lys Val Asn Val Ser Gly Leu Asp Pro Asn Ala Met Tyr Ser Phe Leu
                85                  90                  95

Leu Asp Phe Val Thr Ala Asp Asn His Arg Trp Lys Tyr Val Asn Gly
            100                 105                 110

Glu Trp Val Pro Gly Gly Lys Pro Glu Pro Gln Ala Pro Ser Cys Val
        115                 120                 125

Tyr Ile His Pro Asp Ser Pro Asn Phe Gly Ala His Trp Met Lys Ala
    130                 135                 140

Pro Val Ser Phe Ser Lys Val Lys Leu Thr Asn Lys Leu Asn Gly Gly
145                 150                 155                 160

Gly Gln Ile Met Leu Asn Ser Leu His Lys Tyr Glu Pro Arg Ile His
                165                 170                 175

Ile Val Arg Val Gly Gly Pro Gln Arg Met Ile Thr Ser His Cys Phe
            180                 185                 190
```

Pro Glu Thr Gln Phe Ile Ala Val Thr Ala Tyr Gln Asn Glu Glu Ile
        195                 200                 205

Thr Ala Leu Lys Ile Lys Tyr Asn Pro Phe Ala Lys Ala Phe Leu Asp
    210                 215                 220

Ala Lys Glu Arg Asn Asp His Lys Asp Val Met Glu Glu Pro Gly Asp
225                 230                 235                 240

Cys Gln Gln Pro Gly Tyr Ser Gln Trp Gly Trp Leu Val Pro Gly Ala
                245                 250                 255

Gly Thr Leu Cys Pro Pro Ala Ser Ser His Pro Gln Phe Gly Gly Ser
                260                 265                 270

Leu Ser Leu Pro Ser Thr His Gly Cys Glu Arg Tyr Pro Ala Leu Arg
            275                 280                 285

Asn His Arg Ser Ser Pro Tyr Pro Ser Pro Tyr Ala His Arg Asn Ser
        290                 295                 300

Ser Pro Thr Tyr Ala Asp Asn Ser Ser Ala Cys Leu Ser Met Leu Gln
305                 310                 315                 320

Ser His Asp Asn Trp Ser Ser Leu Gly Val Pro Gly His Thr Ser Met
                325                 330                 335

Leu Pro Val Ser His Asn Ala Ser Pro Pro Thr Gly Ser Ser Gln Tyr
                340                 345                 350

Pro Ser Leu Trp Ser Val Ser Asn Gly Thr Ile Thr Pro Gly Ser Gln
            355                 360                 365

Thr Ala Gly Val Ser Asn Gly Leu Gly Ala Gln Phe Phe Arg Gly Ser
        370                 375                 380

Pro Ala His Tyr Thr Pro Leu Thr His Thr Val Ser Ala Ala Thr Ser
385                 390                 395                 400

Ser Ser Ser Gly Ser Pro Met Tyr Glu Gly Ala Ala Thr Val Thr Asp
                405                 410                 415

Ile Ser Asp Ser Gln Tyr Asp Thr Ala Gln Ser Leu Leu Ile Ala Ser
            420                 425                 430

Trp Thr Pro Val Ser Pro Pro Ser Met His His His His His His
        435                 440                 445

<210> SEQ ID NO 11
<211> LENGTH: 6
<212> TYPE: PRT
<213> ORGANISM: Artificial
<220> FEATURE:
<223> OTHER INFORMATION: Synthetic Peptide

<400> SEQUENCE: 11

Met Ala Asp Glu Ala Pro
1               5

<210> SEQ ID NO 12
<211> LENGTH: 9
<212> TYPE: PRT
<213> ORGANISM: Homo sapiens

<400> SEQUENCE: 12

Trp Leu Leu Pro Gly Thr Ser Thr Leu
1               5

<210> SEQ ID NO 13
<211> LENGTH: 9
<212> TYPE: PRT
<213> ORGANISM: Homo sapiens

```
<400> SEQUENCE: 13

Trp Leu Leu Pro Gly Thr Ser Thr Val
1               5

<210> SEQ ID NO 14
<211> LENGTH: 9
<212> TYPE: PRT
<213> ORGANISM: Homo sapiens

<400> SEQUENCE: 14

Ser Gln Tyr Pro Ser Leu Trp Ser Val
1               5

<210> SEQ ID NO 15
<211> LENGTH: 9
<212> TYPE: PRT
<213> ORGANISM: Homo sapiens

<400> SEQUENCE: 15

Arg Leu Ile Ala Ser Trp Thr Pro Val
1               5

<210> SEQ ID NO 16
<211> LENGTH: 10
<212> TYPE: PRT
<213> ORGANISM: Homo sapiens

<400> SEQUENCE: 16

Ala Met Tyr Ser Phe Leu Leu Asp Phe Val
1               5                   10

<210> SEQ ID NO 17
<211> LENGTH: 1305
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(1305)

<400> SEQUENCE: 17 atg agc tcc cct ggc acc gag agc gcg gga aag agc ctg cag tac cga      48
Met Ser Ser Pro Gly Thr Glu Ser Ala Gly Lys Ser Leu Gln Tyr Arg
1               5                   10                  15 gtg gac cac ctg ctg agc gcc gtg gag aat gag ctg cag gcg ggc agc      96
Val Asp His Leu Leu Ser Ala Val Glu Asn Glu Leu Gln Ala Gly Ser
            20                  25                  30 gag aag ggc gac ccc aca gag cgc gaa ctg cgc gtg ggc ctg gag gag     144
Glu Lys Gly Asp Pro Thr Glu Arg Glu Leu Arg Val Gly Leu Glu Glu
        35                  40                  45 agc gag ctg tgg ctg cgc ttc aag gag ctc acc aat gag atg atc gtg     192
Ser Glu Leu Trp Leu Arg Phe Lys Glu Leu Thr Asn Glu Met Ile Val
    50                  55                  60 acc aag aac ggc agg agg atg ttt ccg gtg ctg aag gtg aac gtg tct     240
Thr Lys Asn Gly Arg Arg Met Phe Pro Val Leu Lys Val Asn Val Ser
65                  70                  75                  80 ggc ctg gac ccc aac gcc atg tac tcc ttc ctg ctg gac ttc gtg gcg     288
Gly Leu Asp Pro Asn Ala Met Tyr Ser Phe Leu Leu Asp Phe Val Ala
                85                  90                  95 gcg gac aac cac cgc tgg aag tac gtg aac ggg gaa tgg gtg ccg ggg     336
Ala Asp Asn His Arg Trp Lys Tyr Val Asn Gly Glu Trp Val Pro Gly
            100                 105                 110
```

```
ggc aag ccg gag ccg cag gcg ccc agc tgc gtc tac atc cac ccc gac      384
Gly Lys Pro Glu Pro Gln Ala Pro Ser Cys Val Tyr Ile His Pro Asp
        115                 120                 125 tcg ccc aac ttc ggg gcc cac tgg atg aag gct ccc gtc tcc ttc agc      432
Ser Pro Asn Phe Gly Ala His Trp Met Lys Ala Pro Val Ser Phe Ser
130                 135                 140 aaa gtc aag ctc acc aac aag ctc aac gga ggg ggc cag atc atg ctg      480
Lys Val Lys Leu Thr Asn Lys Leu Asn Gly Gly Gly Gln Ile Met Leu
145                 150                 155                 160 aac tcc ttg cat aag tat gag cct cga atc cac ata gtg aga gtt ggg      528
Asn Ser Leu His Lys Tyr Glu Pro Arg Ile His Ile Val Arg Val Gly
                165                 170                 175 gat cca cag cgc atg atc acc agc cac tgc ttc cct gag acc cag ttc      576
Asp Pro Gln Arg Met Ile Thr Ser His Cys Phe Pro Glu Thr Gln Phe
            180                 185                 190 ata gcg gtg act gct tat cag aac gag gag atc aca gct ctt aaa att      624
Ile Ala Val Thr Ala Tyr Gln Asn Glu Glu Ile Thr Ala Leu Lys Ile
        195                 200                 205 aag tac aat cca ttt gca aaa gct ttc ctt gat gca aag gaa aga agt      672
Lys Tyr Asn Pro Phe Ala Lys Ala Phe Leu Asp Ala Lys Glu Arg Ser
210                 215                 220 gat cac aaa gag atg atg gag gaa ccc gga gac agc cag caa cct ggg      720
Asp His Lys Glu Met Met Glu Glu Pro Gly Asp Ser Gln Gln Pro Gly
225                 230                 235                 240 tac tcc caa tgg ggg tgg ctt ctt cct gga acc agc acc gtg tgt cca      768
Tyr Ser Gln Trp Gly Trp Leu Leu Pro Gly Thr Ser Thr Val Cys Pro
                245                 250                 255 cct gca aat cct cat cct cag ttt gga ggt gcc ctc tcc ctc ccc tcc      816
Pro Ala Asn Pro His Pro Gln Phe Gly Gly Ala Leu Ser Leu Pro Ser
            260                 265                 270 acg cac agc tgt gac agg tac cca acc ctg agg agc cac cgg tcc tca      864
Thr His Ser Cys Asp Arg Tyr Pro Thr Leu Arg Ser His Arg Ser Ser
        275                 280                 285 ccc tac ccc agc ccc tat gct cat cgg aac aat tct cca acc tat tct      912
Pro Tyr Pro Ser Pro Tyr Ala His Arg Asn Asn Ser Pro Thr Tyr Ser
290                 295                 300 gac aac tca cct gca tgt tta tcc atg ctg caa tcc cat gac aat tgg      960
Asp Asn Ser Pro Ala Cys Leu Ser Met Leu Gln Ser His Asp Asn Trp
305                 310                 315                 320 tcc agc ctt gga atg cct gcc cat ccc agc atg ctc ccc gtg agc cac     1008
Ser Ser Leu Gly Met Pro Ala His Pro Ser Met Leu Pro Val Ser His
                325                 330                 335 aat gcc agc cca cct acc agc tcc agt cag tac ccc agc ctg tgg tct     1056
Asn Ala Ser Pro Pro Thr Ser Ser Ser Gln Tyr Pro Ser Leu Trp Ser
            340                 345                 350 gtg agc aac ggc gcc gtc acc ccg ggc tcc cag gca gca gcc gtg acc     1104
Val Ser Asn Gly Ala Val Thr Pro Gly Ser Gln Ala Ala Ala Val Thr
        355                 360                 365 aac ggg ctg ggg gcc cag ttc ttc cgg ggc tcc ccc gcg cac tac aca     1152
Asn Gly Leu Gly Ala Gln Phe Phe Arg Gly Ser Pro Ala His Tyr Thr
370                 375                 380 ccc ctc acc cat ccg gtc tcg gca ccc tct tcc tcg gga tcc cca ctg     1200
Pro Leu Thr His Pro Val Ser Ala Pro Ser Ser Ser Gly Ser Pro Leu
385                 390                 395                 400 tac gaa ggg gcg gcc gcg gcc aca aac atc gtg gac agc cag tac gac     1248
Tyr Glu Gly Ala Ala Ala Ala Thr Asn Ile Val Asp Ser Gln Tyr Asp
                405                 410                 415 gcc gca gcc caa ggc cgc ctc ata gcc tca tgg aca cct gtg tcg cca     1296
Ala Ala Ala Gln Gly Arg Leu Ile Ala Ser Trp Thr Pro Val Ser Pro
            420                 425                 430
```

```
cct tcc atg                                                            1305
Pro Ser Met
        435

<210> SEQ ID NO 18
<211> LENGTH: 435
<212> TYPE: PRT
<213> ORGANISM: Artificial
<220> FEATURE:
<223> OTHER INFORMATION: Synthetic Construct

<400> SEQUENCE: 18

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Asp Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Val Cys Pro
                245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335

Asn Ala Ser Pro Pro Thr Ser Ser Ser Gln Tyr Pro Ser Leu Trp Ser
```

```
            340                 345                 350
Val Ser Asn Gly Ala Val Thr Pro Gly Ser Gln Ala Ala Val Thr
                355                 360                 365

Asn Gly Leu Gly Ala Gln Phe Phe Arg Gly Ser Pro Ala His Tyr Thr
    370                 375                 380

Pro Leu Thr His Pro Val Ser Ala Pro Ser Ser Gly Ser Pro Leu
385                 390                 395                 400

Tyr Glu Gly Ala Ala Ala Thr Asn Ile Val Asp Ser Gln Tyr Asp
                405                 410                 415

Ala Ala Ala Gln Gly Arg Leu Ile Ala Ser Trp Thr Pro Val Ser Pro
                420                 425                 430

Pro Ser Met
        435

<210> SEQ ID NO 19
<211> LENGTH: 1370
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (10)..(1350)

<400> SEQUENCE: 19
```

| | | | | | | | | | | | | | | | |
|---|---|---|---|---|---|---|---|---|---|---|---|---|---|---|---|
| gaattccgc | atg | gcc | gat | gaa | gct | ccg | agc | tcc | cct | ggc | acc | gag | agc | gcg | 51 |
| | Met | Ala | Asp | Glu | Ala | Pro | Ser | Ser | Pro | Gly | Thr | Glu | Ser | Ala | |
| | 1 | | | | 5 | | | | | 10 | | | | | |

```
gga aag agc ctg cag tac cga gtg gac cac ctg ctg agc gcc gtg gag    99
Gly Lys Ser Leu Gln Tyr Arg Val Asp His Leu Leu Ser Ala Val Glu
 15                  20                  25                  30 aat gag ctg cag gcg ggc agc gag aag ggc gac ccc aca gag cgc gaa   147
Asn Glu Leu Gln Ala Gly Ser Glu Lys Gly Asp Pro Thr Glu Arg Glu
                 35                  40                  45 ctg cgc gtg ggc ctg gag gag agc gag ctg tgg ctg cgc ttc aag gag   195
Leu Arg Val Gly Leu Glu Glu Ser Glu Leu Trp Leu Arg Phe Lys Glu
     50                  55                  60 ctc acc aat gag atg atc gtg acc aag aac ggc agg agg atg ttt ccg   243
Leu Thr Asn Glu Met Ile Val Thr Lys Asn Gly Arg Arg Met Phe Pro
             65                  70                  75 gtg ctg aag gtg aac gtg tct ggc ctg gac ccc aac gcc atg tac tcc   291
Val Leu Lys Val Asn Val Ser Gly Leu Asp Pro Asn Ala Met Tyr Ser
 80                  85                  90 ttc ctg ctg gac ttc gtg gcg gcg gac aac cac cgc tgg aag tac gtg   339
Phe Leu Leu Asp Phe Val Ala Ala Asp Asn His Arg Trp Lys Tyr Val
 95                 100                 105                 110 aac ggg gaa tgg gtg ccg ggg ggc aag ccg gag ccg cag gcg ccc agc   387
Asn Gly Glu Trp Val Pro Gly Gly Lys Pro Glu Pro Gln Ala Pro Ser
                115                 120                 125 tgc gtc tac atc cac ccc gac tcg ccc aac ttc ggg gcc cac tgg atg   435
Cys Val Tyr Ile His Pro Asp Ser Pro Asn Phe Gly Ala His Trp Met
             130                 135                 140 aag gct ccc gtc tcc ttc agc aaa gtc aag ctc acc aac aag ctc aac   483
Lys Ala Pro Val Ser Phe Ser Lys Val Lys Leu Thr Asn Lys Leu Asn
145                 150                 155 gga ggg ggc cag atc atg ctg aac tcc ttg cat aag tat gag cct cga   531
Gly Gly Gly Gln Ile Met Leu Asn Ser Leu His Lys Tyr Glu Pro Arg
        160                 165                 170 atc cac ata gtg aga gtt ggg gat cca cag cgc atg atc acc agc cac   579
Ile His Ile Val Arg Val Gly Asp Pro Gln Arg Met Ile Thr Ser His
    175                 180                 185
```

```
         175                 180                 185                 190
tgc ttc cct gag acc cag ttc ata gcg gtg act gct tat cag aac gag        627
Cys Phe Pro Glu Thr Gln Phe Ile Ala Val Thr Ala Tyr Gln Asn Glu
                    195                 200                 205 gag atc aca gct ctt aaa att aag tac aat cca ttt gca aaa gct ttc        675
Glu Ile Thr Ala Leu Lys Ile Lys Tyr Asn Pro Phe Ala Lys Ala Phe
            210                 215                 220 ctt gat gca aag gaa aga agt gat cac aaa gag atg atg gag gaa ccc        723
Leu Asp Ala Lys Glu Arg Ser Asp His Lys Glu Met Met Glu Glu Pro
        225                 230                 235 gga gac agc cag caa cct ggg tac tcc caa tgg ggg tgg ctt ctt cct        771
Gly Asp Ser Gln Gln Pro Gly Tyr Ser Gln Trp Gly Trp Leu Leu Pro
240                 245                 250 gga acc agc acc gtg tgt cca cct gca aat cct cat cct cag ttt gga        819
Gly Thr Ser Thr Val Cys Pro Pro Ala Asn Pro His Pro Gln Phe Gly
255                 260                 265                 270 ggt gcc ctc tcc ctc ccc tcc acg cac agc tgt gac agg tac cca acc        867
Gly Ala Leu Ser Leu Pro Ser Thr His Ser Cys Asp Arg Tyr Pro Thr
                275                 280                 285 ctg agg agc cac cgg tcc tca ccc tac ccc agc ccc tat gct cat cgg        915
Leu Arg Ser His Arg Ser Ser Pro Tyr Pro Ser Pro Tyr Ala His Arg
            290                 295                 300 aac aat tct cca acc tat tct gac aac tca cct gca tgt tta tcc atg        963
Asn Asn Ser Pro Thr Tyr Ser Asp Asn Ser Pro Ala Cys Leu Ser Met
        305                 310                 315 ctg caa tcc cat gac aat tgg tcc agc ctt gga atg cct gcc cat ccc       1011
Leu Gln Ser His Asp Asn Trp Ser Ser Leu Gly Met Pro Ala His Pro
    320                 325                 330 agc atg ctc ccc gtg agc cac aat gcc agc cca cct acc agc tcc agt       1059
Ser Met Leu Pro Val Ser His Asn Ala Ser Pro Pro Thr Ser Ser Ser
335                 340                 345                 350 cag tac ccc agc ctg tgg tct gtg agc aac ggc gcc gtc acc ccg ggc       1107
Gln Tyr Pro Ser Leu Trp Ser Val Ser Asn Gly Ala Val Thr Pro Gly
                355                 360                 365 tcc cag gca gca gcc gtg acc aac ggg ctg ggg gcc cag ttc ttc cgg       1155
Ser Gln Ala Ala Ala Val Thr Asn Gly Leu Gly Ala Gln Phe Phe Arg
            370                 375                 380 ggc tcc ccc gcg cac tac aca ccc ctc acc cat ccg gtc tcg gca ccc       1203
Gly Ser Pro Ala His Tyr Thr Pro Leu Thr His Pro Val Ser Ala Pro
        385                 390                 395 tct tcc tcg gga tcc cca ctg tac gaa ggg gcg gcc gcg gcc aca aac       1251
Ser Ser Ser Gly Ser Pro Leu Tyr Glu Gly Ala Ala Ala Ala Thr Asn
    400                 405                 410 atc gtg gac agc cag tac gac gcc gca gcc caa ggc cgc ctc ata gcc       1299
Ile Val Asp Ser Gln Tyr Asp Ala Ala Ala Gln Gly Arg Leu Ile Ala
415                 420                 425                 430 tca tgg aca cct gtg tcg cca cct tcc atg cat cac cat cac cat cac       1347
Ser Trp Thr Pro Val Ser Pro Pro Ser Met His His His His His His
                435                 440                 445 tga gactagtccc gggcggccgc                                             1370

<210> SEQ ID NO 20
<211> LENGTH: 446
<212> TYPE: PRT
<213> ORGANISM: Artificial
<220> FEATURE:
<223> OTHER INFORMATION: Synthetic Construct

<400> SEQUENCE: 20

Met Ala Asp Glu Ala Pro Ser Ser Pro Gly Thr Glu Ser Ala Gly Lys
```

```
1               5                    10                    15
Ser Leu Gln Tyr Arg Val Asp His Leu Ser Ala Val Glu Asn Glu
                20                  25                  30

Leu Gln Ala Gly Ser Glu Lys Gly Asp Pro Thr Glu Arg Leu Arg
                35                  40                  45

Val Gly Leu Glu Glu Ser Glu Leu Trp Leu Arg Phe Lys Glu Leu Thr
    50                  55                  60

Asn Glu Met Ile Val Thr Lys Asn Gly Arg Arg Met Phe Pro Val Leu
65                      70                  75                  80

Lys Val Asn Val Ser Gly Leu Asp Pro Asn Ala Met Tyr Ser Phe Leu
                85                  90                  95

Leu Asp Phe Val Ala Ala Asp Asn His Arg Trp Lys Tyr Val Asn Gly
                100                 105                 110

Glu Trp Val Pro Gly Gly Lys Pro Glu Pro Gln Ala Pro Ser Cys Val
            115                 120                 125

Tyr Ile His Pro Asp Ser Pro Asn Phe Gly Ala His Trp Met Lys Ala
            130                 135                 140

Pro Val Ser Phe Ser Lys Val Lys Leu Thr Asn Lys Leu Asn Gly Gly
145                 150                 155                 160

Gly Gln Ile Met Leu Asn Ser Leu His Lys Tyr Glu Pro Arg Ile His
                165                 170                 175

Ile Val Arg Val Gly Asp Pro Gln Arg Met Ile Thr Ser His Cys Phe
            180                 185                 190

Pro Glu Thr Gln Phe Ile Ala Val Thr Ala Tyr Gln Asn Glu Glu Ile
            195                 200                 205

Thr Ala Leu Lys Ile Lys Tyr Asn Pro Phe Ala Lys Ala Phe Leu Asp
210                 215                 220

Ala Lys Glu Arg Ser Asp His Lys Glu Met Met Glu Glu Pro Gly Asp
225                 230                 235                 240

Ser Gln Gln Pro Gly Tyr Ser Gln Trp Gly Trp Leu Leu Pro Gly Thr
                245                 250                 255

Ser Thr Val Cys Pro Pro Ala Asn Pro His Pro Gln Phe Gly Gly Ala
            260                 265                 270

Leu Ser Leu Pro Ser Thr His Ser Cys Asp Arg Tyr Pro Thr Leu Arg
            275                 280                 285

Ser His Arg Ser Ser Pro Tyr Pro Ser Pro Tyr Ala His Arg Asn Asn
            290                 295                 300

Ser Pro Thr Tyr Ser Asp Asn Ser Pro Ala Cys Leu Ser Met Leu Gln
305                 310                 315                 320

Ser His Asp Asn Trp Ser Ser Leu Gly Met Pro Ala His Pro Ser Met
                325                 330                 335

Leu Pro Val Ser His Asn Ala Ser Pro Pro Thr Ser Ser Ser Gln Tyr
            340                 345                 350

Pro Ser Leu Trp Ser Val Ser Asn Gly Ala Val Thr Pro Gly Ser Gln
            355                 360                 365

Ala Ala Ala Val Thr Asn Gly Leu Gly Ala Gln Phe Phe Arg Gly Ser
            370                 375                 380

Pro Ala His Tyr Thr Pro Leu Thr His Pro Val Ser Ala Pro Ser Ser
385                 390                 395                 400
```

```
                                -continued

Ser Gly Ser Pro Leu Tyr Glu Gly Ala Ala Ala Thr Asn Ile Val
            405                 410                 415

Asp Ser Gln Tyr Asp Ala Ala Ala Gln Gly Arg Leu Ile Ala Ser Trp
            420                 425                 430

Thr Pro Val Ser Pro Pro Ser Met His His His His His His
            435                 440                 445
```

YEAST-BASED IMMUNOTHERAPY FOR CHORDOMA

CROSS-REFERENCE TO RELATED APPLICATIONS

This application is a national stage application under 35 U.S.C. 371 of PCT Application No. PCT/US2014/031183 having an international filing date of Mar. 19, 2014, which designated the United States, which PCT application claimed the benefit of priority under 35 U.S.C. 119(e) to U.S. Provisional Application Ser. No. 61/803,332, filed Mar. 19, 2013. The entire disclosure of U.S. Provisional Application Ser. No. 61/803,332, filed Mar. 19, 2013, and PCT Application No. PCT/US2014/031183 having an international filing date of Mar. 19, 2014 are each incorporated herein by reference.

GOVERNMENT RIGHTS

This invention was created in the performance of a Cooperative Research and Development Agreement with the National Institutes of Health, an Agency of the Department of Health and Human Services. The government has certain rights in this invention.

STATEMENT REGARDING JOINT RESEARCH AGREEMENT

This invention was made by or on behalf of parties to a Cooperative Research and Development Agreement, executed May 8, 2008. The parties to the Cooperative Research and Development Agreement are: GlobeImmune, Inc. and the U.S. Department of Health and Human Services, as represented by National Cancer Institute, an Institute, Center or Division of the National Institutes of Health.

REFERENCE TO A SEQUENCE LISTING

This application contains a Sequence Listing submitted electronically as a text file by EFS-Web. The text file, named "7797-2-PCT_ST25", has a size in bytes of 76 KB, and was recorded on 14 Mar. 2014. The information contained in the text file is incorporated herein by reference in its entirety pursuant to 37 CFR § 1.52(e)(5).

FIELD OF THE INVENTION

The present invention generally relates to yeast-based immunotherapeutic compositions and methods for the prevention and/or treatment of chordoma.

BACKGROUND OF THE INVENTION

Chordoma is a rare bone cancer primarily of the spine arising from embryonic remnants of the notochord that is aggressive, locally invasive, and has a poor prognosis (Chugh et al., 2007, *The Oncologist* 12:1344-1350). It occurs more frequently in men than women (60% vs. 40%), with a median age at diagnosis of 59 years with a generally progressive increase in incidence with age (McMaster et al., 2001, *Cancer Causes Control* 12: 1-11). Despite being frequently misquoted in the literature as having a proclivity for the sacrococcygeal region, the most comprehensive population analysis of 400 cases from the SEER data base indicate chordomas are almost equally distributed between the sacrum (29.2%), skull base (32%), and mobile spine (32.8%) (McMaster et al., ibid.; Walcott et al. (2012) *Lancet Oncol* 13:e69-76). In this study, median overall survival was 6.29 years with 5-year, 10-year and 20-year survival dropping precipitously to 68%, 40% and 13% respectively, across all races and sex (McMaster et al., supra). However, it is important to note that the authors identified that patients diagnosed and treated later in the 22-year survey had significantly improved survival, and hypothesized that this was a result of improved surgical and radiation techniques. Four later (smaller) studies support this hypothesis with a total of 230 subjects having 5-year and 10-year overall survival of 82% and 57% (Ferraresi et al. (2010), *BMC Cancer* 10:22. (Table 4); Stacchiotti et al. (2010), *Ann Surg Oncol* 17(1): 211-9).

The United States incidence of chordoma is 0.08 per 100,000 resulting in approximately 250 new U.S. cases annually (McMaster et al., supra; U.S. Census Bureau estimate of U.S. population (315,091,138) as of Jan. 1, 2013). The incidence in Europe-27 (EU) is similar to the U.S., resulting in approximately 400 new EU cases annually (Chordoma Foundation website, 2013; European Commission EuroStat database EU-27 population as of Jan. 1, 2012 (503,700,000)). With an average overall survival of approximately 10 years, the prevalence of chordoma is approximately 8 per million, or about 2500 in the U.S. and 4000 in EU. The incidence and prevalence of chordoma in other regions is unknown.

Chordomas are indolent and slow growing, therefore they are often clinically silent until later stages of disease. Chordomas are not typically metastatic on presentation, with only 5% showing metastasis to the lungs, bone, skin and brain at the time of initial presentation. Patient survival appears to be less affected by distant metastasis than by local progression of the disease. Local progression has emerged as the most important predictor of mortality, and the extent of initial resection has become the most important factor in affording an opportunity for cure (Walcott et al., supra).

Aggressive surgical resection with an emphasis on neurological preservation, followed by adjuvant radiation therapy is the standard of care for this disease. Aggressive en-bloc surgical resection with wide surgical margins has substantially improved local control of disease recurrence (Hsieh et al. (2009), *Spine* 34:2233-39; Stacchiotti et al., supra; Tzortzidis et al. (2006), *Neurosurgery* 59(2):230-7). However, complex removal of the tumor itself is not a satisfactory treatment goal; preservation of a patient's neurological function and quality of life must also take priority when assessing surgical outcomes. Any tumor that remains after surgery, particularly when small in volume, is managed with radiotherapy. Currently, complete resection is attainable in ~50% of sacral chordomas, with much lower rates for spinal and skull base chordomas (Walcott et al., supra). While stand-alone radiotherapy has proven to be ineffective, there appears to be a consensus that Hadron-based (not photon) adjuvant radiotherapy offers an added advantage over surgery alone, with 5-year local control rates of 50-60% (Walcott et al., supra).

Chordomas are generally insensitive to conventional chemotherapies, as expected given their slow growing nature (Azzarelli et al. (1988), *J Surg Oncol* 37(3):185-91). However, limited case reports have suggested dedifferentiated chordoma may be sensitive to aggressive chemotherapy (Fleming et al. (1993), *Cancer* 72:714-18). Molecular profiling of chordomas has revealed these tumors over express PDGF receptors A and B, as well as KIT receptors. As a result, several tyrosine kinase inhibitors such as imatinib and sunitinib have been tried in chordoma patients. The best results obtained to date were with sunitinib where 44% of patients with chordoma (4/9) had stable disease for 16 weeks (Merriam et al. (2009), *J Clin Oncol* 27: 3154-60).

Accurate diagnosis of spinal and skull based tumors is important. Brachyury has become a discriminating biomarker for chordoma. When combined with cytokeratin staining, sensitivity and specificity for detection of chordomas is 98% and 100% respectively (Oakley et al. (2008), *Mod Path* 21, 1461-1469). Brachyury, also known as "T", is a mesodermal transcription factor and member of the T-box complex of genes, playing a role in early development, as well as the formation and differentiation of posterior mesoderm and axial development in vertebrates (see, e.g., Wilkinson et al., 1990, *Nature* 343(6259):657-659); Beddington et al., 1992, *Development* (Suppl.):157-165; Schulte-Merker et al., 1994, *Development* 120: 1009-1015; Kispert and Herrmann, 1994, *Dev. Biol.* 161:179-193; Showell et al., 2004, *Dev Dyn* 229:201-218). More recently, Palena and colleagues have demonstrated that Brachyury is expressed in a variety of human tumor tissues and cancer cell lines (Palena et al., 2007, *Clin. Cancer Res.* 13(8):2471-2478). Studies by Fernando et al. have shown that Brachyury promotes the epithelial-mesenchymal transition (EMT) in human tumor cells, conferring on tumor cells a mesenchymal phenotype, as well as migratory and invasive abilities, while attenuating tumor cell cycle progression (Fernando et al., 2010, *J. Clin. Invest.* 120(2):533-544). Accordingly, Brachyury is involved in metastatic progression of cancer. However, in chordoma, Brachyury appears to be more broadly involved at all stages of the disease. In patients with familial and sporadic chordoma, studies have identified a common gene duplication of brachyury (Yang et al., *Nat Genet* 2009; 41: 1176-78).

Despite best efforts at initial treatment, most chordomas will recur or progress. While many patients elect to undergo complex reoperations, despite a high rate of morbidity for all lesion locations, there are very few reports of treatment protocols and outcomes for recurrent lesions. Previous radiation treatment often limits the ability to safely re-irradiate, as well as causing increased morbidity for subsequent surgeries. Accordingly, there is a need in the art for improved therapeutic approaches for the treatment of chordoma. In addition, given the occurrence of familial chordoma, there is a need in the art for options for the prevention of chordoma, or options that delay the onset of, or improve the outcomes in, familial chordoma.

SUMMARY OF THE INVENTION

One embodiment of the invention relates to a method to treat chordoma in an individual who has chordoma. The method includes the step of administering to an individual who has chordoma, an immunotherapeutic composition comprising: (a) a yeast vehicle; and (b) a cancer antigen comprising at least one Brachyury antigen. Another embodiment of the invention relates to the use of an immunotherapeutic composition comprising a yeast vehicle and a cancer antigen comprising at least one Brachyury antigen to chordoma in an individual who has chordoma. Yet another embodiment of the invention relates to the use an immunotherapeutic composition comprising a yeast vehicle and a cancer antigen comprising at least one Brachyury antigen to prevent or delay the onset of chordoma.

In one aspect of these embodiments of the invention, the individual is an individual having a non-resectable, locally recurring lesion. In one aspect, the local recurrence of the lesion occurs between 3 and 9 months prior to administration of the immunotherapeutic composition. In one aspect, the individual is an individual having oligometastatic disease. In still another aspect, the individual is an individual having first recurrence of a non-resectable lesion or a resectable lesion. In yet another aspect, the individual is an indivulat having metastatic disease.

In any of the foregoing aspects, the individual is being treated or has been treated with another therapy for cancer. In any of the foregoing aspects, the therapy is radiation therapy. The radiation therapy may be administered prior to the administration for the immunotherapeutic composition, concurrently with the administration of the immunotherapeutic composition and/or sequentially with the administration of the immunotherapeutic composition. In still any of the foregoing aspects, the therapy can also include tumor resection. In still any of the foregoing aspects, the therapy can also include chemotherapy. In still any of the foregoing aspects, the therapy can include drug targeted therapy. In one aspect, the drug targeted therapy is selected from of tyrosine kinase inhibitors, EGFR inhibitors, and STAT3 inhibitors. In still any of the foregoing aspects, the therapy can include administration of one or more additional immunotherapeutic compositions. In one aspect, the additional immunotherapeutic composition is a yeast vehicle and an antigen other than a Brachyury antigen. In still another aspect, the additional immunotherapeutic composition is a yeast vehicle and an antigen selected from epidermal growth factor receptor (EGFR), platelet-derived growth factor (PDGF) receptor, kit receptor, CD24, type II & X collagen, fibronectin, matrillin 3 (MATN3), high molecular weight-melanoma associated antigen (HMW-MAA), matrix metalloproteinase MMP-9, and MMP-19.

Another embodiment of the invention relates to a method to prevent chordoma, delay the onset of chordoma, or improve the outcome of chordoma in an individual who has a history of familial chordoma. The method includes the step of administering to an individual who has a history of familial chordoma, an immunotherapeutic composition comprising: (a) a yeast vehicle; and (b) a cancer antigen comprising at least one Brachyury antigen; wherein at the time of administering, the individual has not been diagnosed with chrodoma.

In one aspect of any of the embodiments or aspects of the invention described above or elsewhere herein, the Brachyury antigen is full-length human Brachyury. In one aspect, the Brachyury antigen is not full-length Brachyury. In one aspect, the Brachyury antigen has an amino acid sequence represented by SEQ ID NO:6, SEQ ID NO:18, SEQ ID NO:2, or an amino acid sequence that is at least 95% identical to SEQ ID NO:6, SEQ ID NO:18, or SEQ ID NO:2. In one aspect, the Brachyury antigen comprises from at least position 1 or 2 to between position 255 and the C-terminus of SEQ ID NO:6, SEQ ID NO:18, or SEQ ID NO:2. In one aspect, the Brachyury antigen comprises from at least position 1 or 2 to between position 430 and the C-terminus of SEQ ID NO:6, SEQ ID NO:18, or SEQ ID NO:2. In one aspect, the Brachyury antigen comprises positions 246 to 254 of SEQ ID NO:6, SEQ ID NO:18, or SEQ ID NO:2. In one aspect, the Brachyury antigen comprises SEQ ID NO:6, positions 2-435 of SEQ ID NO:6, or an amino acid sequence that is at least 95% identical to SEQ ID NO:6. In one aspect, the Brachyury antigen comprises SEQ ID NO:18, positions 2-435 of SEQ ID NO:18, or an amino acid sequence that is at least 95% identical to SEQ ID NO:18. In one aspect, the Brachyury antigen comprises SEQ ID NO:2, positions 2-435 of SEQ ID NO:2, or an amino acid sequence that is at least 95% identical to SEQ ID NO:2. In one aspect, the Brachyury antigen comprises SEQ ID NO:6, positions 2-435 of SEQ ID NO:6, or an amino acid sequence that is at least 99% identical to SEQ ID NO:6. In one aspect, the Brachyury antigen comprises SEQ ID NO:18, positions 2-435 of SEQ ID NO:18, or an amino acid sequence that is at least 99% identical to SEQ ID NO:18. In one aspect, the Brachyury antigen comprises SEQ ID NO:2, positions 2-435 of SEQ ID NO:2, or an amino acid sequence that is at least 99% identical to SEQ ID NO:2.

In one aspect of any of the embodiments or aspects of the invention described above or elsewhere herein, the cancer antigen is a fusion protein. In one aspect, the fusion protein has an amino acid sequence represented by SEQ ID NO:8, or an amino acid sequence that is at least 95% identical to SEQ ID NO:8. In one aspect, the fusion protein has an amino acid sequence represented by SEQ ID NO:20, or an amino acid sequence that is at least 95% identical to SEQ ID NO:20.

In any of the foregoing aspects of any of the embodiments or aspects of the invention described above or elsewhere herein, the yeast vehicle is a whole yeast. In any of the forgoing aspects, the whole yeast is killed. In any one of the foregoing aspects, the whole yeast is heat-inactivated. In any one of the foregoing aspects, the yeast expresses the antigen. In any one of the foregoing aspects, the yeast is from a genus selected from the group consisting of: *Saccharomyces, Candida, Cryptococcus, Hansenula, Kluyveromyces, Pichia, Rhodotorula, Schizosaccharomyces* and *Yarrowia*. In one aspect, the yeast is from *Saccharomyces*. In one aspect, the yeast is from *Saccharomyces cerevisiae*.

In any of the foregoing aspects of any of the embodiments of the invention described above or elsewhere herein, the composition is formulated in a pharmaceutically acceptable excipient suitable for administration by injection of a subject. In any of the foregoing aspects, the subject is administered the immunotherapeutic composition in a dose from about 0.1 Y.U. to about 100. Y.U. In any of the foregoing aspects, the subject is administered the immunotherapeutic composition in a dose from about 10 Y.U. to about 80 Y.U. In any of the foregoing aspects, the subject is administered the immunotherapeutic composition in a dose of 2 Y.U., 40 Y.U. or 80 Y.U.

In any of the foregoing aspects of any of the embodiments of the invention described above or elsewhere herein, the immunotherapeutic composition is administered weekly. In any of the foregoing aspects, the immunotherapeutic composition is administered every other week. In any of the foregoing aspects, the immunotherapeutic composition is administered monthly. In yet in any of the foregoing aspects, the immunotherapeutic composition is administered weekly for 5 weeks followed by monthly. In still any of the foregoing aspects, the immunotherapeutic composition is administered at two week intervals for 7 rounds of treatment, followed by monthly. In any of the foregoing aspects, the immunotherapeutic composition is administered at more than one site on the individual to form a single dose.

In any of the foregoing aspects of any of the embodiments of the invention described above or elsewhere herein, the immunotherapeutic composition is administered concurrently with another therapy for cancer as described above or elsewhere.

BRIEF DESCRIPTION OF THE DRAWING

FIG. 1 shows tumor measurement changes in individual subjects in a phase I expansion study where 7 patients were administered 40 Y.U. of an immunotherapeutic composition disclosed herein, specifically GI-6301. The x-axis scale on the left side of day zero is different than the scale on the right side of day zero.

DETAILED DESCRIPTION OF THE INVENTION

This invention generally relates to yeast-based immunotherapeutic compositions and the use of yeast-based immunotherapeutic compositions for the prevention and/or treatment of chordoma. The invention includes the use of a yeast-based immunotherapeutic composition (also referred to as yeast-based immunotherapy), including, but not limited to, yeast-based immunotherapy compositions comprising a yeast vehicle and Brachyury antigens or immunogenic domains thereof (also referred to herein as "yeast-Brachyury immunotherapy" or "yeast-Brachyury immunotherapeutic compositions"). Yeast-based immunotherapy compositions targeting Brachyury have been described in detail in PCT Publication No. WO 2012/125998, published Sep. 30, 2012, and incorporated herein by reference in its entirety. The inventors describe herein the specific use of yeast-based immunotherapy, and in one aspect of the invention, yeast-based Brachyury immunotherapy, for the treatment of chordoma (e.g., classical (or conventional), chondroid or dedifferentiated chordoma), and/or for the prevention, or delay of onset of, chordoma (e.g., familial chordoma).

Conventional chordomas are the most common type of chordomas. They are characterized by the absence of cartilaginous or additional mesenchymal components. Chondroid chordomas contain both chordomatous and chondromatous features, and have a tendency to form at the spheno-occipital region of the skull base. As of 2007, this variant accounted for 5%-15% of all chordomas and up to 35% of cranial chordomas. Dedifferentiation or sarcomatous transformation occurs in 2%-8% of chordomas (Chugh et al., 2007, *The Oncologist* 12:1344-1350). Chondroid chordomas tend to be less aggressive than conventional chordomas, while dedifferentiated chordomas are more aggressive, faster growing and more likely to metastasize (www.chordomafoundation.org).

The method of the invention is also readily adaptable to the use of additional tumor antigens within the same yeast composition, or to use in combination with other yeast-based immunotherapeutics that target other antigens present in chordoma tumors (also referred to herein as lesions) (sequentially or concurrently), or to use in combination with other treatments/therapies for chordoma. Additional tumor antigens and additional treatments/therapies that are useful for the treatment or prevention of chordoma are described in detail below.

Yeast-based immunotherapy compositions described for use in the methods of the invention induce innate immune responses, as well as adaptive immune responses against the target antigen (e.g., Brachyury), including CD4-dependent TH17 and TH1 T cell responses and antigen-specific CD8$^+$ T cell responses, which include cytotoxic T lymphocyte (CTL) responses, all without the use of exogenous adjuvants, cytokines, or other immunostimulatory molecules, many of which have toxicity issues. In addition, yeast-based immunotherapeutic compositions inhibit regulatory T cell (Treg) numbers and/or functionality, thereby enhancing effector T cell responses that might normally be suppressed by the presence of the tumor, for example. Moreover, as compared to immunotherapeutic compositions that immunize by generating antibody responses, the antigen-specific, broad-based, and potent cellular immune responses elicited by yeast-based immunotherapy are believed to be particularly effective in targeting tumor cells. Indeed, numerous studies have shown that immunotherapeutic approaches are enhanced when tumor cells are targeted via CD8+ CTLs which recognize tumor peptides in the context of MHC Class I molecules.

Yeast-based immunotherapy is highly adept at activating antigen presenting cells, and has a unique ability to cross-prime the immune response, generating CD8+ CTL responses that are typically effective against tumors, even in the face of what may otherwise be a suppressive environment. Since this type of immunotherapy utilizes the natural ability of the antigen presenting cell to present relevant immunogens, it is not necessary to know the precise identity of CTL epitopes or MHC Class II epitopes of the target antigen (e.g., Brachyury) to produce an effective immunotherapeutic according to the present invention, although agonist epitopes may be included in a yeast-based immunotherapeutic composition to further enhance immune responses, as described in detail below. In fact, multiple CD4+ and CD8+ T cell epitopes can be targeted in a single yeast-based immunotherapeutic composition, and so the yeast-based immunotherapeutics of the invention are not limited to the use of short peptides and in fact, the use of longer polypeptides and fusion proteins in these compositions is efficacious. Accordingly, by using yeast-based immunotherapy, the use of algorithms and complex formulas to identify putative T cell epitopes is eliminated.

Furthermore, yeast-based immunotherapy can be effectively utilized in an immunization protocol (prophylactic or therapeutic) without the use of exogenous adjuvants, immunostimulatory agents or molecules, costimulatory molecules, or cytokines, although such agents may be included, if desired. Moreover, yeast-based immunotherapy can be administered repeatedly without losing efficacy, as may be problematic with other types of immunotherapy.

Methods for the Treatment or Prevention of Chordoma

One embodiment of the invention relates to a method to treat chordoma by administering a yeast-based immunotherapy composition of the invention to an individual (subject) with chordoma. Yeast-based immunotherapy compositions for chordoma are described in detail below. As used herein, to "treat" chordoma, or any permutation thereof (e.g., "treated for chordoma", etc.) generally refers to administering a composition of the invention once the chordoma has occurred (e.g., once the chordoma has been diagnosed or detected in an individual), or once the chordoma has recurred, with at least one therapeutic goal of the treatment (as compared to in the absence of this treatment) including: ameliorating at least one symptom of chordoma, such as by reducing tumor burden in the individual; inhibiting, reducing, decreasing, or diminishing tumor growth or the rate of tumor growth (tumor growth kinetics) in the individual; increasing or extending survival of the individual, which can include overall survival and/or progression free survival; improving tumor response rate, (i.e., as measured by RECIST and/or Choi, defined below); delaying, inhibiting, arresting or preventing the recurrence of the tumor; preventing, inhibiting, reversing or delaying development of tumor migration and/or tumor invasion of other tissues (metastatic cancer); arresting, preventing, inhibiting, reversing or delaying progression of the cancer in the individual; improving long term memory immune responses against the tumor antigen(s) expressed by the chordoma; increasing the sensitivity of the lesions to radiation therapy, chemotherapy and/or targeted drug therapy; and/or improving the general health of the individual. As used herein, the term "tumor" with respect to a chordoma, can be used interchangeably with the term "lesion".

Another embodiment of the invention relates to a method to prevent chordoma, inhibit or delay the onset of chordoma, or improve outcomes for chordoma (e.g., by increasing survival, by inhibiting cancer progression, by reducing or controlling tumor burden over time and/or increasing sensitivity of the tumor to chemotherapy or radiation therapy). This method includes the step of administering a yeast-based immunotherapy composition to an individual who does not presently have chordoma, but who is or may be predisposed to develop chordoma. For example, an individual who is predisposed to develop chordoma can include an individual who has a family history of chordoma (referred to herein as familial chordoma) and therefore is at a higher risk of developing chordoma as compared to the population as a whole. An individual who may be predisposed to develop chordoma may also be identified through genetic screening or the presence of benign notochord tumors. Familial chordoma is typically identified as chordoma occurring in a family wherein two or more blood relatives have a history of chordoma (Yang, X., et al. Int. J. Cancer. 116:487-491; 2005). In some cases of familial chordoma, unique Brachyury gene duplications have been found (Yang, X., et al. Nat Gen. 2009, 41(11):1176-1178).

To "prevent" or "protect" from chordoma, or any permutation thereof (e.g., "prevention of chordoma", etc.), generally refers to administering a composition of the invention before chordoma has occurred or developed, with at least one goal of the treatment (as compared to in the absence of this treatment) including: preventing or delaying the onset or development of chordoma, or, should chordoma nonetheless occur after the treatment, at least improving the outcomes in the individual as compared to in the absence of the treatment, including, but not limited to, reducing tumor burden in the individual; inhibiting (reducing, decreasing, diminishing) tumor growth or the rate of tumor growth in the individual; increasing (extending) survival of the individual, which can include overall survival and/or progression free survival; improving tumor response rate, (i.e., as measured by RECIST and/or Choi, defined below); delaying, inhibiting, arresting or preventing the recurrence of the tumor; preventing, inhibiting, reversing or delaying development of tumor migration and/or tumor invasion of other tissues (metastatic cancer); arresting, preventing, inhibiting, reversing or delaying progression of the cancer in the individual; improving long term memory immune responses against the tumor antigens expressed by the chordoma; increasing the sensitivity of the tumor to radiation therapy, chemotherapy and/or targeted drug therapy; and/or improving the general health of the individual.

As discussed above, in one embodiment of the invention, treatment with a yeast-based immunotherapy composition of the invention improves progression free survival (PFS) and/or overall survival (OS) in the treated subject. Progression free survival in cancer is generally defined as the length of time during and after a treatment for cancer that a patient lives with the cancer, but the cancer does not worsen, as determined by the treating clinician and the appropriate evaluation criteria for the cancer. Overall survival in cancer is generally defined as the length of time from either the date of diagnosis or the start of treatment that the patient is still alive, regardless of whether or not the cancer has progressed (worsened).

In one embodiment of the invention, treatment with a yeast-based immunotherapy composition of the invention reduces tumor growth rate (tumor growth rate kinetics). Various models may be used to calculate tumor growth rate, including models based on exponential growth (Yorke et al., 1993, *Cancer Research* 53, 2987-2993), the Universal Law model (West et al., 2001, *Nature* 413, 628-631), and/or "doubling time" (the time it takes for the population of cells to reach twice its size; Spratt et al., 1964, *Annals of surgery* 159, 161-171; Steele et al., 1973, *The Journal of thoracic and cardiovascular surgery* 65, 140-151; Collins et al., 1956, *The American journal of roentgenology, radium therapy, and nuclear medicine* 76, 988-1000.

In one embodiment of the invention, treatment with a yeast-based immunotherapy composition of the invention improves response rates in the subject, i.e., as measured by RECIST or Choi criteria. "RECIST" refers to Response Evaluation Criteria in Solid Tumors and is a set of published guidelines that define when tumors in cancer patients improve, stabilize or progress. A RECIST-defined response depends on changes in the size of target lesions, as determined by non-invasive imaging assessment. RECIST criteria were originally published in February 2000 by an international collaboration including the European Organization for Research and Treatment of Cancer (EORTC), National Cancer Institute (NCI) of the United States and the National Cancer Institute of Canada Clinical Trials Group. (Therasse et al., *J. Natl. Cancer Inst.* 2000, 92:205-216)) and were revised in 2009 as described in Eisenhauer et al., *Eur. J. Cancer*, 2009, 45:228-247. As described in Eisenhauer et al., supra, a "Complete Response" or CR is currently defined as a disappearance of all target lesions, with any pathological lymph nodes (target or non-target) having a reduction in short axis to <10 mm. A "Partial Response" or "PR" is currently defined as at least a 30% decrease in the sum of diameters of target lesions, taking as reference the baseline sum diameters. "Stable Disease" or "SD" is defined as neither sufficient shrinkage to qualify for PR nor sufficient increase to qualify for PD, taking as reference the smallest sum diameters while on study. A "Progressive Disease" or "PD" is defined as at least a 20% increase in the sum of diameters of target lesions, taking as reference the smallest sum on study. In addition, the sum must also demonstrate an absolute increase of at least 5 mm. The appearance of one or more new lesions is also considered to be progression. Additional criteria apply to non-target lesions as described in Eisenhauer et al. supra.

"Choi" criteria refers to a set of computed tomography response criteria originally described by Choi et al. (*J. Clin. Oncol.* 2007, 25(13):1753-1759) and evaluates a change in the size or in the density of target lesions as measured by CT. The Choi criteria also categorize patients using the CR, PR, SD and PD groupings. CR is defined as a disappearance of all lesions with no new lesions. PR is defined as a decrease in size >10% or a decrease in tumor attenuation >15% on CT, with no new lesions and no obvious progression of non-measurable disease. SD is defined as not meeting criteria for CR, PR or PD and no symptomatic deterioration attributed to tumor progression. PD is defined as an increase in tumor size >10% and does not meet criteria of PR by tumor attenuation on CT, and/or has new lesions.

In one embodiment of the invention, treatment with a yeast-based immunotherapy composition of the invention improves long term memory immune responses against the tumor antigens expressed by the chordoma. Immune responses against chordoma and chordoma tumor antigens can be evaluated by detecting $CD4^+$ and/or $CD8^+$ T cells emerging or expanding on treatment, and measurement of parameters of general immune activation, including frequency of immune cell subsets in peripheral blood ($CD8^+$ memory/effector T cells, $CD4^+$ memory/effector T cells, Tregs, NK cells, DCs) and changes in serum levels of cytokines (e.g., IFN-γ, IL-10, IL-12, IL-2, IL-4, TGF-β, etc.). Immune responses can be detected and evaluated using various immunological assays known in the art including, but not limited to, ELISpot responses, flow cytometric methods, and lymphocyte proliferation assays (LPA).

As discussed above, chordoma is characterized by the expression of Brachyury and indeed, Brachyury is a distinguishing biomarker for this cancer, i.e., Brachyury expression is common to and a specific biomarker for all chordomas. Therefore, in one embodiment, the yeast immunotherapy composition administered in any method of the invention as described above or elsewhere herein is a yeast-Brachyury immunotherapy composition (described in detail below). The method of the invention therefore includes the step of administering to the individual who has chordoma, or the individual who is at risk of developing chordoma but in whom Brachyury-expressing cancer cells are not currently detected, a yeast-Brachyury immunotherapeutic composition as described herein, including, but not limited to: (a) a yeast vehicle; and (b) a cancer antigen comprising at least one Brachyury antigen. The present invention includes the delivery (administration, immunization) of a yeast-based immunotherapeutic composition of the invention, including, but not limited to, a yeast-Brachyury immunotherapeutic composition, to a subject or individual. The administration process can be performed ex vivo or in vivo, but is typically performed in vivo. Ex vivo administration refers to performing part of the regulatory step outside of the patient, such as administering a composition of the present invention to a population of cells (dendritic cells) removed from a patient under conditions such that a yeast vehicle, antigen(s) and any other agents or compositions are loaded into the cell, and returning the cells to the patient. The therapeutic composition of the present invention can be returned to a patient, or administered to a patient, by any suitable mode of administration.

Administration of a composition can be systemic, mucosal and/or proximal to the location of the target site (e.g., near a site of a tumor). Suitable routes of administration will be apparent to those of skill in the art. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intrathecal, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992). In one aspect, a yeast-based immunotherapeutic composition of the invention is administered subcutaneously. In one aspect, the yeast-based immunotherapeutic composition is administered directly into a tumor milieu. In one aspect, a yeast-based immunotherapeutic composition of the invention is administered intrathecally.

In general, a suitable single dose of a yeast-based immunotherapeutic composition, including a yeast-Brachyury immunotherapeutic composition, is a dose that is capable of effectively providing a yeast vehicle and the antigen to a given cell type, tissue, or region of the patient body in an amount effective to elicit an antigen-specific immune response against one or more tumor antigens or epitopes (e.g., Brachyury), when administered one or more times over a suitable time period. For example, in one embodiment, a single dose of a yeast-based composition of the present invention is from about $1 \times 10^5$ to about $5 \times 10^7$ yeast cell equivalents per kilogram body weight of the organism being administered the composition. In one aspect, a single dose of a yeast vehicle of the present invention is from about 0.1 Yeast Units (Y.U., which is $1 \times 10^6$ yeast cells or yeast cell equivalents) to about 100 Y.U. ($1 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$ . . . ). In one embodiment, doses include doses between 1 Y.U. and 40 Y.U., doses between 1 Y.U. and 50 Y.U., doses between 1 Y.U. and 60 Y.U., doses between 1 Y.U. and 70 Y.U., or doses between 1 Y.U. and 80 Y.U., and in one aspect, between 10 Y.U. and 40 Y.U., 50 Y.U., 60 Y.U., 70 Y.U., or 80 Y.U. In one embodiment, the doses are administered at different sites on the individual but during the same dosing period. For example, a 40 Y.U. dose may be administered by injecting 10 Y.U. doses to four different sites on the individual during one dosing period, or a 20 Y.U. dose may be administered by injecting 5 Y.U. doses to four different sites on the individual, or by injecting 10 Y.U. doses to two different sites on the individual, during the same dosing period. The invention includes administration of an amount of the yeast-based immunotherapy composition (e.g., 1, 2, 3, 4, 5, 6, 7, 8, 9 10, 11, 12, 13, 14, 15, 16, 17, 18, 19, 20 Y.U. or more) at 1, 2, 3, 4, 5, 6, 7, 8, 9, 10, or more different sites on an individual to form a single dose. One Yeast Unit (Y.U.) is $1 \times 10^7$ yeast cells or yeast cell equivalents.

"Boosters" or "boosts" of an immunotherapeutic composition of the invention are administered, for example, when the immune response against the antigen has waned or as needed to provide an immune response or induce a memory response against a particular antigen or antigen(s). Boosters can be administered about 1, 2, 3, 4, 5, 6, 7, or 8 weeks apart, or monthly, bimonthly, quarterly, annually, and/or in a few or several year increments after the original administration, depending on the status of the individual being treated and the goal of the therapy at the time of administration (e.g., prophylactic, active treatment, maintenance). In one embodiment, an administration schedule is one in which doses of yeast-based immunotherapeutic composition is administered at least 1, 2, 3, 4, 5, 6, 7, 8, 9, 10, or more times over a time period of from weeks, to months, to years. In one embodiment, the doses are administered weekly or biweekly for 1, 2, 3, 4, 5, 6, 7, 8, 9, 10 or more doses, followed by biweekly or monthly doses as needed to achieve the desired preventative or therapeutic treatment for chordoma. In one embodiment, doses are administered biweekly for 1, 2, 3, 4, 5, 6, 7, 8, 9, 10 or more doses, followed by additional monthly doses until the desired preventative or therapeutic result is achieved. In one embodiment, doses are administered monthly for 1, 2, 3, 4, 5, 6, 7, 8, 9, 10 or more doses, followed by additional monthly doses or followed by doses delivered at different frequencies as needed to achieve the desired preventative or therapeutic treatment for chordoma. In all of the dosing protocols described herein, additional boosters can then be given at similar or longer intervals (e.g., months or years) as a maintenance or remission therapy, if desired. In one aspect, boosters are administered for long term maintenance therapy (i.e., after the main course of therapy is completed, with an intention of preventing or delaying recurrence of disease, or with the intention of maintaining disease stabilization). In one aspect, boosters are administered for prophylactic treatment for individuals having familial chordoma.

In one aspect of the method to treat chordoma, the individual is additionally treated with at least one other therapeutic compound or therapeutic protocol useful for the treatment of chordoma. Such therapy can include any of the therapeutic protocols or use of any therapeutic compound or agent that is useful for treating chordoma or that may be useful for treating chordoma, including, but not limited to, surgical resection, radiation therapy (including, but not limited to, stand alone radiation therapy and adjuvant radiation therapy, especially hadron-based radiation therapy), chemotherapy or targeted cancer or drug therapy (e.g., tyrosine kinase inhibitors, including, but not limited to, imatinib, sunitinib cetuximab, gefitinib, erlotinib, nilotinib, dasatinib, lapatinib and everolimus; STAT3 inhibitors, anthracyclines; cisplatins; alkylating agents; camptothecin analogues), stem cell transfer, cytokine therapy, adoptive T cell transfer, and/or administration of a second immunotherapeutic composition. In the case of administration of a second immunotherapeutic composition, such compositions may include, but are not limited to, additional yeast-based immunotherapy, recombinant virus-based immunotherapy (viral vectors), immunostimulant therapy (including chemotherapy with immunostimulating properties), DNA vaccines, and other immunotherapy compositions.

In one aspect, radiation therapy can be administered prior to, concurrently and/or sequentially with the administration of the immunotherapeutic composition of the present invention. In addition, radiation therapy can be administered in combination with surgical resection. Advances in radiation technology and treatment have led to more strategic targeting of lesions with higher doses of radiation. In addition, advances such as the introduction of hadrons (i.e., high-dose protons or charged particles, including carbon ions, helium, or neon) have led to higher doses (doses that would permanently damage normal tissue) of radiation being delivered to the target with minimum injury to the surrounding tissue and improved radiobiological effect (Walcott, B. The Lacent Oncology, Vol 13 Feb. 2012, p. e69-e79). For example, a retrospective analysis of the use of carbon ion radiotherapy for sacral chordoma reported doses from 52.8 to 73.6 GyE (Imai et al., 2011, *J. Radiol.*, 84:S048-S054). Another type of radiation called proton beam therapy, which utilizes protons (charged particles which are obtained from hydrogen atoms), is most often recommended for chordoma patients because it allows delivery of very high doses of radiation to the tumor while minimizing doses to tissues just millimeters away (see, e.g., Wilson, *Radiology,* 1946, 47:487-491; and Hug et al., 1999, *J. Neurosurgery* 91, 432-439 (1999)). Proton beam delivery is customized to the individual tumor so that the radiation energy is deposited at the point of greatest penetration of protons in the tissue, with little radiation to normal tissue beyond the target. Photon radiation, e.g., electromagnetic radiation typically delivered by external beam radiation, is also used to treat chordomas. High doses of photon radiation used in chordoma treatment can be about 45-80 Gy, whereas treatment with conventional radiation therapy is typically at dose amounts of about 40-60 Gy (Walcott, B. The Lacent Onccology, Vol 13 Feb. 2012, p. e69-e79). Certain other types of conformal radiation, such as radiosurgery (including Gamma Knife and CyberKnife) and intensity modulated radiotherapy (IMRT) are also used to treat chordomas, and their use typically depends on the size and location of the tumor (Di Maio et al., 2011, *J Neurosurg. December;* 115(6):1094-105). If a lesion returns after initial irradiation, it may or may not be possible to have radiation therapy again. This is because every tissue in the body has a certain life-time maximum tolerance for radiation, beyond which serious injury will occur. However, in the method of the present invention, additional radiation of a lesion may be included in a protocol if the treating clinician and current best practices deem it possible and likely to be beneficial to the chordoma patient.

In one aspect, radiation therapy is administered to one or more lesions within about 18 months, about 17 months, about 16 months, about 15 months, about 14 months, about 13 months, about 12 months, about 11 months, about 10 months, about 9 months, about 8 months, about 7 months, about 6 months, about 5 months, about 4 months, about 3 months, about 2 months, or about 1 month prior to the subject receiving administration of the immunotherapeutic composition of the present invention. During the radiation therapy, the subject can receive at least 1 dose, at least 2 doses, at least 3 doses, at least 4 doses, at least 5 doses, at least 6 doses, at least 7 doses, at least 8 doses, at least 9 doses or at least 10 doses of radiation therapy. In addition, following the first administration of the immunotherapeutic composition, the subject can receive one or more doses of radiation therapy.

In another aspect, the subject can receive targeted drug therapy alone or administered prior to, concurrently or sequentially with the administration of the radiation therapy. Such targeted drug therapy can include administration of one or more tyrosine kinase (TKI) inhibitor drugs, epidermal growth factor receptor (EGFR) inhibitor drugs and/or signal transducer and activator of transcription 3 (STAT3) inhibitor drugs (Walcott, B. The Lacent Onccology, Vol 13 Feb. 2012, p. e69-e79). For example, 400 mg/day to 800 mg/day of imatinib mesylate (Gleevec®), a small molecule TKI inhibitor drug with specificity for the kinase domains of platelet-derived growth factor receptors (PDGFR) can be administered to the subject, typically as an oral dose. Overall tumor response rate, as defined by RECIST can be monitored to determine if the subject is responding to the therapy. Imatinib meslylate can be administered to the subjects from days to years (Stacchiotti, S., et al. Curr Oncol Rep, May 2011 online; Casali, P. G., J Clinical Oncology, 2005 ASCO Annual Meeting Proceedings, Vol. 23. No. 16S). Another example of a targeted drug therapy includes administration of a 150 mg/day dose of erlotinib (Tarceva®), an EGFR inhibitor drug, to the subject, typically as an oral dose (Lauay et al. BMC Cancer, 2011, 11:423). Erlotinib can be administered from days to years with overall tumor rate being monitored. The targeted drug therapy can be administered alone or in combination with another targeted drug therapy or can be administered prior to, concurrently or sequentially with the administration of another drug therapy.

In one aspect, the second immunotherapeutic composition includes a second cancer antigen that does not include Brachyury antigen. For example, a second immunotherapeutic composition useful in combination with a yeast-Brachyury immunotherapeutic composition is a yeast-immunotherapeutic composition comprising another cancer antigen. Cancer antigens that have been associated with or observed in chordoma tumors are of particular interest as antigen targets in the present invention. Such cancer antigens may include, but are not limited to, epidermal growth factor receptor (EGFR) (see, e.g., Harris et al., *Breast Cancer Res. Treat,* 29:1-2 (1994); platelet-derived growth factor (PDGF) receptor (see, e.g., GenBank® Accession No. GI:129890 and Gronwald et al., 1988, Proc. Natl. Acad. Sci. U.S.A. 85 (10), 3435-3439; and GenBank® Accession No. GI:129892 and Claesson-Welsh et al., 1989, Proc. Natl. Acad. Sci. U.S.A. 86 (13), 4917-4921); kit receptor (see, e.g., Accession No. GI:125472 and Yarden et al., 1987, EMBO J. 6 (11), 3341-3351); CD24 (see, e.g., GI:143811372 and Kay et al., 1991, J. Immunol. 147 (4), 1412-1416); aggrecan (see, e.g., Accession No. GI:22209083 and Strausberg et al., 2002, Proc. Natl. Acad. Sci. U.S.A. 99 (26), 16899-16903); type II & X collagen (see, e.g., Accession No. GI:124056489 and Su et al., 1989, Nucleic Acids Res. 17 (22), 9473; and Accession No. GI:1405723 and Beier et al., 1996, Matrix Biol. 15 (6), 415-422); fibronectin (see, e.g., Accession No. GI:384872704 and Labeit and Kolmerer, 1995, Science 270 (5234), 293-296 (1995)); matrillin 3 (MATN3) (see, e.g., Accession No. GI:14548113 and Belluoccio et al., 1998, Genomics 53 (3), 391-394); high molecular weight-melanoma associated antigen (HMW-MAA) (see, e.g., Accession No. GI:47419930 and Campoli et al., 2004, Crit Rev Immunol. 24(4):267-96); matrix metalloproteinase MMP-9 (see, e.g., Accession No. GI:269849668 and Huhtala et al., 1991, J. Biol. Chem. 266 (25), 16485-16490); and MMP-19 (see, e.g., Accession No. GI:442535505 and Sedlacek et al., 1998, Immunobiology 198 (4): 408-23); as well as modifications of such antigens, splice variants of such antigens, and epitope agonists of such antigens, as well as combinations of such antigens, and/or immunogenic domains thereof, modifications thereof, and variants thereof. Other cancer antigens are known in the art and may also be suitable target antigens for immunotherapy for chordoma. The invention is not limited to the antigens described specifically above or elsewhere herein.

In one aspect of the invention, one or more additional therapeutic agents or therapeutic protocols are administered or performed sequentially and/or concurrently with the administration of the yeast-based immunotherapy composition (e.g., surgical resection of the tumor, administration of radiation therapy, administration of chemotherapy or targeted cancer therapy, administration of another immunotherapy composition or protocol, cytokine therapy, adoptive T cell transfer, agents useful in combination with a yeast-based immunotherapy or stem cell transplantation). Agents useful in combination with a yeast-based immunotherapy composition in accordance with the invention include, but are not limited to: anti-CD40, CD40L, lymphocyte-activation gene 3 (LAG3) protein and/or IMP321 (T-cell immunostimulatory factor derived from the soluble form of LAG3), anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®); anti-CD4; anti-CD25; anti-PD-1, anti-PD-L1, anti-PD-L2; agents that block FOXP3 (e.g., to abrogate the activity/kill CD4+/CD25+T regulatory cells); Flt3 ligand, imiquimod (Aldara™), Toll-like receptor (TLR) agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogues thereof including IMiDs® (which are structural and functional analogues of thalidomide (e.g., REVLIMID® (lenalidomide), POMALYST® (pomalidomide)) and any agents that modulate the number of, modulate the activation state of, and/or modulate the survival of antigen-presenting cells or of TH17, TH1, and/or Treg cells. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein. In addition, one or more therapies can be administered or performed prior to the first dose of yeast-based immunotherapy composition or after the first dose is administered. As one example, for individuals who have a chordoma that can be resected, surgical resection, optionally followed by radiation therapy, and then by yeast-based immunotherapy, may be representative of the course of therapy. In one embodiment, one or more therapies can be administered or performed in an alternating manner with the dosing of yeast-based immunotherapy composition, such as in a protocol in which the yeast-based composition is administered at prescribed intervals in between one or more consecutive doses of chemotherapy or other targeted therapy. As another example, for individuals who have chordoma that is locally recurrening or who have metastatic disease, where the tumor progression has occurred within the previous 12 months, or within the last 3-9 months prior to commencement of treatment, yeast-based immunotherapy may be representative of the primary course of therapy. Prior to commencement of treatment with yeast-based immunotherapy, the individual may also receive surgery, radiation therapy, or another chordoma therapy. Approximately 6 months after the initiation of the yeast-based immunotherapy (or at the appropriate time point as determined by the treating physician), optionally, radiation therapy may be given if it is determined that the subject has a lesion that can be irradiated, followed by monitoring until determination of tumor progression, or partial or complete response to therapy. If additional radiation therapy is not given, the subject can be monitored until determination of tumor progression, or partial or complete response to therapy.

In one embodiment, the yeast-based immunotherapy composition is administered in one or more doses over a period of time prior to commencing additional therapies. In other words, the yeast-based immunotherapeutic composition is administered as a monotherapy for a period of time, and then an additional therapy is added (e.g., chemotherapy), either concurrently with new doses of yeast-based immunotherapy, or in an alternating fashion with yeast-based immunotherapy. Alternatively or in addition, another therapy may be administered for a period of time prior to beginning administration of the yeast-based immunotherapy composition, and the concepts may be combined (e.g., surgical resection of a tumor, followed by monotherapy with yeast-based immunotherapy for several weeks, followed by alternating doses of chemotherapy or targeted therapy and yeast-based immunotherapy for weeks or months, optionally followed by monotherapy using yeast-based immunotherapy or another therapy, or by a new protocol of combinations of therapy provided sequentially, concurrently, or in alternating fashion). Various protocols for the treatment of chordoma using yeast-based immunotherapy are contemplated by the invention, and these examples should be considered to be non-limiting examples of various possible protocols.

In the method of the present invention, the subject to be treated with the immunotherapeutic composition of the present invention, can be a chordoma subject having a first occurrence of a non-resectable lesion (i.e., not able to be completely surgically removed) or a resectable lesion; a subject having a non-resectable, locally recurring lesion (i.e., locally recurring is a lesion that reappears in the vicinity of (at or near) the same place as an original or primary lesion that has been removed), whether first recurrence or not; a subject having oligometastatic disease as described below; or a subject having metastatic disease as described below. In one aspect, the subject may or may not have had previous radiation therapy, surgery and/or targeted drug therapy. In another aspect, the lesion may or may not have been previously irradiated.

In the method of the present invention, one example of a chordoma subject to be treated with the immunotherapeutic composition of the present invention, is a subject having a non-resectable (i.e., not able to be completely surgically removed), locally recurring lesion (i.e., a locally recurring is a lesion that reappears in the vicinity of (at or near) the same place as an original or primary lesion that has been removed). In one aspect, the non-resectable lesion has not been previously irradiated, however, the subject may or may not have been exposed to radiation therapy at other lesions prior to treatment with the immunotherapeutic composition of the present invention. In yet another aspect, the non-resectable lesion has been previously irradiated prior to treatment with the immunotherapeutic composition of the present invention. In another embodiment, the subject has a lesion that is non-resectable due to the location of the lesion, but may have received one or more additional therapeutic treatments for chordoma.

In the method of the present invention, another example of a chordoma subject to be treated with the immunotherapeutic composition of the present invention, is a subject having oligometastatic disease and a non-resectable lesion. As used herein "oligometastatic disease" is defined as a restricted tumor metastatic capacity, or more particularly, metastatic cancer (cancer that has spread from the primary site of origination to other sites), wherein the metastases (metastatic lesions or metastatic tumors) are limited in number and location (see, e.g., Hellman and Weichselbaum, 1995, *J. Clin. Oncol.* 13(1):8-10; Weichselbaum and Hellman, 2011, *S. Nat. Rev. Clin. Oncol.* 8, 378-382). With respect to a chordoma, oligometastatic disease is generally considered to constitute 5 or fewer, 4 or fewer, 3 or fewer, 2 or fewer, or 1 lesions occurring near the site of a primary lesion. In one aspect, the non-resectable lesion has not been previously irradiated, however, the subject may or may not have been exposed to radiation therapy at other locations prior to treatment with the immunotherapeutic composition of the present invention. In yet another aspect, the non-resectable lesion has been previously irradiated prior to treatment with the immunotherapeutic composition of the present invention.

In the method of the present invention, another example of a chordoma subject to be treated with the immunotherapeutic composition of the present invention, is a subject having oligometastatic disease and a post-resection lesion (i.e., surgical removal of the lesion being monitored). In one aspect, the subject has not previously received radiation therapy. In another aspect, the subject has received previous radiation therapy.

In the method of the present invention, yet another example of a chordoma subject to be treated with the immunotherapeutic composition of the present invention, is a subject having a first occurrence of a non-resectable lesion. In one aspect, the non-resectable lesion has not been previously irradiated, however, the subject may or may not have been exposed to radiation therapy at other locations prior to treatment with the immunotherapeutic composition of the present invention. In yet another aspect, the non-resectable lesion has been previously irradiated prior to treatment with the immunotherapeutic composition of the present invention.

In the method of the present invention, another example of a chordoma subject to be treated with the immunotherapeutic composition of the present invention, is a subject having metastatic disease (i.e., cancer has spread from the place where it first started, or primary site, to another place in the body, characterized in that the cancer contains cells that are derived from the original or primary tumor) and a lesion that has not been previously irradiated. In another aspect, the lesion has been previously irradiated.

In the method of the present invention, another example of a chordoma subject to be treated with the immunotherapeutic composition of the present invention, is a subject having locally recurrent or metastatic disease with tumor progression occurring between 3 and 9 months prior to commencement of treatment with the immunotherapeutic composition of the invention. In one aspect, the subject may have received any acceptable line of therapy for chordoma, including without limitation, surgery, radiation, chemotherapy or treatment with a targeted drug therapy. The subject receives the yeast-based immunotherapeutic composition as described herein. At 6 months after initiation of the immunotherapeutic composition, the subject is evaluated by a care provider to determine if they have a lesion that can be irradiated. If a lesion can be irradiated, the lesion will be treated with radiation therapy and the subject will be monitored and evaluated until the subject is considered to respond to the immunotherapeutic composition as discussed below. If no lesion can be irradiated, the subject will not receive radiation therapy and will be monitored and evaluated until the subject is considered to respond to the immunotherapeutic composition. The subject is considered to respond to the immunotherapeutic composition by a determination of progression free survival (PFS) as defined by RECIST, as well as by tumor response rate (defined by RECIST and Choi, and evaluated in irradiated and non-irradiated lesions for comparison) and/or tumor growth rate kinetics (evaluated at 6 months prior to immunotherapeutic treatment vs. 6 months after immunotherapeutic treatment). For PFS, the median is expected to be 9 months as compared to non-treated control subjects (expected 5 months). The subject's response to the immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

Subjects that can be treated with the immunotherapeutic composition of the present invention can include subjects having the one or more of the following: presence of a solid tumor, measurable disease (disease must be evaluable) or non-measurable disease, positivity of the disease by a highly sensitive method (such as a PCR based assay for circulating tumor cells or other similar methods), Eastern Cooperative Oncology Group (ECOG) status grade of 0-1 (wherein grade 0 indicates fully active, able to carry on all pre-disease performance without restriction and grade 1 indicates restricted in physically strenuous activity but ambulatory and able to carry on work of a light or sedentary nature), creatinine levels of $</-1.5 \times$ULN (upper limit of normal), ALT levels (alanine-aminotransferase) of $</-2.5 \times$ULN, AST levels (aspartate aminotransferase) of $</-2.5 \times$ULN, Bilirubin (Bili) levels of $</-1.5 \times$ULN, absolute neutrophil count (ANC) of >1500, platelet count of >100,000, minimum of 2 weeks from prior chemotherapy treatment, prior immune therapy or combinations thereof.

In the method of the present invention, compositions and therapeutic compositions can be administered to any animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to treat or protect utilizing the invention include humans, non-human primates, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

Compositions for Use in the Methods of the Invention

The methods of the present invention utilize a yeast-based immunotherapy composition, and in one embodiment, a yeast-Brachyury immunotherapy composition. According to the present invention, a yeast-based immunotherapy composition useful in the present invention is a composition comprising: (a) a yeast vehicle (described in detail below); and (b) at least one cancer antigen. The cancer antigen is an antigen expressed by a chordoma, including, but not limited to, Brachyury, epidermal growth factor receptor (EGFR), platelet-derived growth factor (PDGF) receptor (A or B), kit receptor, CD24, aggrecan, type II & X collagen, fibronectin, matrillin 3, high molecular weight-melanoma associated antigen (HMW-MAA), matrix metalloproteinase MMP-9, and MMP-19. In the case of a yeast-Brachyury immunotherapy composition, the composition comprises: (a) a yeast vehicle; and (b) a cancer antigen comprising one or more Brachyury antigen(s) and/or immunogenic domain(s) thereof. The cancer antigen, which may include a Brachyury antigen and/or other chordoma-expressed antigen, is most typically expressed as a recombinant protein by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or more cancer antigens are loaded into a yeast vehicle or otherwise complexed with, attached to, mixed with or administered with a yeast vehicle as described herein to form a composition of the present invention.

A "yeast-Brachyury immunotherapeutic composition" is a specific type of "yeast-based immunotherapeutic composition" that contains at least one Brachyury antigen or immunogenic domain thereof. The phrase, "yeast-based immunotherapeutic composition" may be used interchangeably with "yeast-based immunotherapy product", "yeast-based immunotherapy composition", "yeast-based composition", "yeast-based immunotherapeutic", "yeast-based vaccine", or derivatives of these phrases. An "immunotherapeutic composition" is a composition that elicits an immune response sufficient to achieve at least one therapeutic benefit in a subject. As used herein, yeast-based immunotherapeutic composition refers to a composition that includes a yeast vehicle component and that elicits an immune response sufficient to achieve at least one therapeutic benefit in a subject. More particularly, a yeast-based immunotherapeutic composition is a composition that includes a yeast vehicle component and typically, an antigen component, and can elicit or induce an immune response, such as a cellular immune response, including without limitation a T cell-mediated cellular immune response. In one aspect, a yeast-based immunotherapeutic composition useful in the invention is capable of inducing a CD8$^+$ and/or a CD4$^+$ T cell-mediated immune response and in one aspect, a CD8$^+$ and a CD4$^+$ T cell-mediated immune response, particularly against a target antigen (e.g., a cancer antigen). A CD4$^+$ immune response can include TH1 immune responses, TH2 immune responses, TH17 immune responses, or any combination of the above. Yeast-based immunotherapeutics are particularly capable of generating TH1 and TH17 responses. A CD8$^+$ immune response can include a cytotoxic T lymphocyte (CTL) response, and yeast-based immunotherapeutics are capable of generating such responses. In one aspect, a yeast-based immunotherapeutic composition modulates the number and/or functionality of regulatory T cells (Tregs) in a subject. Yeast-based immunotherapy can also be modified to promote one type of response over another, e.g., by the addition of cytokines, antibodies, and/or modulating the manufacturing process for the yeast. Optionally, a yeast-based immunotherapeutic composition is capable of eliciting a humoral immune response. The yeast-based immunotherapeutic composition may elicit a humoral immune response when the antigen is presented external to the yeast such as either attached on the surface of the yeast or as admixture.

Yeast-based immunotherapeutic compositions of the invention may be either "prophylactic" or "therapeutic". When provided prophylactically, the compositions of the present invention are provided in advance of the development of, or the detection of the development of, a chordoma, with the goal of preventing, inhibiting or delaying the development or onset of chordoma; and/or preventing, inhibiting or delaying tumor migration and/or tumor invasion of other tissues (metastases) and/or generally preventing or inhibiting progression of chordoma in an individual. As discussed herein, Brachyury is expressed in all chordomas and is a hallmark of chordoma, and therefore yeast-Brachyury immunotherapeutic compositions are particularly useful as prophylactic therapy in individuals who may develop chordoma. Prophylactic compositions can be administered to individuals that appear to be cancer-free (healthy, or normal, individuals), but who are, or may be, at risk for developing chordoma, such as individuals with a history of familial chordoma or who otherwise have at least one immediate family member with chordoma. When provided therapeutically, the immunotherapy compositions are provided to an individual with chordoma, with the goal of ameliorating the cancer, such as by reducing tumor burden in the individual; inhibiting tumor growth in the individual; increasing survival of the individual; preventing, inhibiting, reversing or delaying development of tumor migration and/or tumor invasion of other tissues (metastatic cancer) and/or preventing, inhibiting, reversing or delaying progression of the cancer in the individual.

Typically, a yeast-based immunotherapy composition includes a yeast vehicle and at least one cancer antigen comprising a chordoma antigen (cancer antigen associated with or expressed by chordoma), where the chordoma antigen is expressed by, attached to, loaded into, or mixed with the yeast vehicle. In some embodiments, the chordoma antigen is provided as a fusion protein. As discussed herein, chordoma antigens can include, but are not limited to, Brachyury, EGFR, PDGF receptor, kit receptor, CD24, aggrecan, type II & X collagen, fibronectin, matrillin 3, high molecular weight-melanoma associated antigen (HMW-MAA), matrix metalloproteinase MMP-9, and MMP-19. Several Brachyury proteins and fusion proteins suitable for use in the compositions and methods of the invention are described below. In one aspect of the invention, a fusion protein useful as a cancer antigen for chordoma can include two or more antigens, e.g., a Brachyury antigen and another cancer antigen that is not a Brachyury antigen, which in one embodiment may be provided within a single fusion protein, or two different Brachyury antigens.

According to the present invention, a yeast vehicle used in a yeast-based immunotherapy composition for the treatment or prevention of chordoma is any yeast cell (e.g., a whole or intact cell) or a derivative thereof (see below) that can be used in conjunction with one or more antigens, immunogenic domains thereof or epitopes thereof in a composition of the invention (e.g., a therapeutic or prophylactic composition). The yeast vehicle can therefore include, but is not limited to, a live intact (whole) yeast microorganism (i.e., a yeast cell having all its components including a cell wall), a killed (dead) or inactivated intact yeast microorganism, or derivatives of intact yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, *Meth. Enzymol.* 194, 662-674, incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is a preparation of isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle for use in the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains). In accordance with one aspect of the present invention, non-pathogenic yeast strains are used.

Genera of yeast strains that may be used in the invention include but are not limited to *Saccharomyces, Candida* (which can be pathogenic), *Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe,* and *Yarrowia lipolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe. S. cerevisiae* is useful as it is relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) and/or other proteins to be expressed at high levels. Another yeast strain is useful in the invention is *Saccharomyces cerevisiae* W303α. In addition, any mutant yeast strains can be used in the present invention, including those that exhibit reduced post-translational modifications of expressed target antigens or other proteins, such as mutations in the enzymes that extend N-linked glycosylation.

The yeast-based immunotherapy composition of the invention includes at least one antigen expressed by or associated with chordoma. According to the present invention, the general use herein of the term "antigen" refers: to any portion of a protein (e.g., peptide, partial protein, full-length protein), wherein the protein is naturally occurring or synthetically derived or designed, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered by an element of the immune system (e.g., T cells, antibodies).

An antigen can be as small as a single epitope, a single immunogenic domain or larger, and can include multiple epitopes or immunogenic domains. As such, the size of an antigen can be as small as about 8-11 amino acids (i.e., a peptide) and as large as: a full length protein, a multimer, a fusion protein, a chimeric protein, a whole cell, a whole microorganism, or any portions thereof (e.g., protein fragments (polypeptides) lysates of whole cells or extracts of microorganisms). Antigens useful in the yeast-based immunotherapeutic of the present invention are peptides, polypeptides, full-length proteins, multimers, fusion proteins and chimeric proteins. In addition, antigens can include carbohydrates, which can be loaded into a yeast vehicle or into a composition of the invention. It will be appreciated that in some embodiments (e.g., when the antigen is expressed by the yeast vehicle from a recombinant nucleic acid molecule), the antigen is a protein, fusion protein, chimeric protein, or fragment thereof, rather than an entire cell or microorganism. For expression in yeast, an antigen is of a minimum size capable of being expressed recombinantly in yeast if the antigen is the entire protein to be expressed by the yeast, and is typically at least or greater than 25 amino acids in length, or at least or greater than 26, at least or greater than 27, at least or greater than 28, at least or greater than 29, at least or greater than 30, at least or greater than 31, at least or greater than 32, at least or greater than 33, at least or greater than 34, at least or greater than 35, at least or greater than 36, at least or greater than 37, at least or greater than 38, at least or greater than 39, at least or greater than 40, at least or greater than 41, at least or greater than 42, at least or greater than 43, at least or greater than 44, at least or greater than 45, at least or greater than 46, at least or greater than 47, at least or greater than 48, at least or greater than 49, or at least or greater than 50 amino acids in length, or at least or greater than 25-50 amino acids in length, or at least or greater than 30-50 amino acids in length, or at least or greater than 35-50 amino acids in length, or at least or greater than 40-50 amino acids in length, or at least or greater than 45-50 amino acids in length, although smaller proteins may be expressed, and considerably larger proteins (e.g., hundreds of amino acids in length or even a few thousand amino acids in length) may be expressed. In one aspect, a full-length protein or a protein that is lacking between 1 and 20 amino acids from the N- and/or the C-terminus may be expressed. Fusion proteins and chimeric proteins are also antigens that may be expressed in the invention. A "target antigen" is an antigen that is specifically targeted by an immunotherapeutic composition of the invention (i.e., an antigen against which elicitation of an immune response is desired). A "cancer antigen" is an antigen that comprises at least one antigen that is associated with or expressed by a cancer (e.g., chordoma) such as an antigen expressed by a tumor cell, such that targeting the antigen also targets the cancer. A cancer antigen can include one or more antigens from one or more proteins, including one or more tumor-associated proteins. A "Brachyury antigen" is an antigen derived, designed, or produced from a Brachyury protein.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, the immunogen elicits a cell-mediated immune response, including a CD4+ T cell response (e.g., TH1, TH2 and/or TH17) and/or a CD8+ T cell response (e.g., a CTL response).

An "immunogenic domain" of a given antigen can be any portion, fragment or epitope of an antigen (e.g., a peptide fragment or subunit or an antibody epitope or other conformational epitope) that contains at least one epitope that can act as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains need not be linear sequences within a protein, such as in the case of a humoral immune response, where conformational domains are contemplated.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be up to 25 amino acids or longer. In addition, T cell epitopes have predicted structural characteristics depending on the specific MHC molecules bound by the epitope. Epitopes can be linear sequence epitopes or conformational epitopes (conserved binding regions). Most antibodies recognize conformational epitopes.

In one embodiment of the invention, the yeast-based immunotherapy composition used in the invention is a yeast-Brachyury immunotherapy composition. Brachyury (which may also be referred to as "T") is a highly conserved protein among multiple different animal species and is a transcription factor that contains a "T-box" domain or "T-domain", a DNA-binding domain motif shared among several different proteins, collectively called the T-box family of proteins. Human Brachyury was first cloned in 1996 (Edwards et al., supra). One nucleotide sequence encoding human Brachyury is represented herein by SEQ ID NO:1, which is an mRNA sequence that was obtained from GENBANK® Accession No. NM_003181 (GI:19743811). SEQ ID NO:1 encodes a 435 amino acid human Brachyury protein, the amino acid sequence of which is represented here as SEQ ID NO:2 (also found in GENBANK® Accession No. NP_003172; GI:4507339).

Another human Brachyury protein disclosed herein is a variant of the human Brachyury protein represented by SEQ ID NO:2, and has the amino acid sequence of SEQ ID NO:6. SEQ ID NO:6, also a 435 amino acid protein, is encoded by a nucleotide sequence represented herein by SEQ ID NO:5. SEQ ID NO:6 is approximately 99% identical to SEQ ID NO:2 over the full-length of the protein. SEQ ID NO:6 differs from SEQ ID NO:2 at position 177 (Asp vs. Gly, respectively), position 368 (Thr vs. Ser, respectively) and position 409 (Asn vs. Asp, respectively).

Another human Brachyury protein disclosed herein is an agonist of the human Brachyury protein represented, e.g., by SEQ ID NO:2 or SEQ ID NO:6. As generally used herein, an "agonist" is any compound or agent, including without limitation small molecules, proteins, peptides, antibodies, nucleic acid binding agents, etc., that binds to a receptor or ligand and produces or triggers a response, which may include agents that mimic or enhance the action of a naturally occurring substance that binds to the receptor or ligand. When used in the context of a Brachyury antigen of the invention, an "agonist" antigen or protein refers to an antigen or protein that comprises at least one T cell agonist epitope, which may also be referred to as a "mimotope". A mimotope peptide is a peptide that mimics the structure of a wild-type epitope and as an agonist, the mimotope mimics or enhances the action (biological function) of the natural epitope. For example, the amino acid sequence of SEQ ID NO:12 (WLLPGTSTL) is a T cell epitope of a wild-type Brachyury protein. The amino acid sequence of SEQ ID NO:13 (WLLPGTSTV) is a mimotope or agonist of the T cell epitope of SEQ ID NO:12, where the leucine at position 9 of SEQ ID NO:12 has been substituted with a valine in SEQ ID NO:13.

One human Brachyury agonist antigen is represented here by SEQ ID NO:18. SEQ ID NO:18 is a 435 amino acid protein is encoded by a nucleotide sequence represented herein by SEQ ID NO:17. SEQ ID NO:18 is identical to SEQ ID NO:6, except for a substitution of a leucine at position 254 (with respect to SEQ ID NO:6) with a valine in SEQ ID NO:18. This substitution creates a T cell agonist epitope in SEQ ID NO:18 at positions 246 to 254 that, without being bound by theory, is believed to induce enhanced T cell responses against Brachyury as compared to the wild-type epitope (positions 246 to 254 of SEQ ID NO:6).

Positions 41 to 223 of any of SEQ ID NO:2, SEQ ID NO:6 or SEQ ID NO:18 represent the T-box DNA binding domain of human Brachyury, and the T-box domain in other Brachyury sequences, including Brachyury sequences from other species, can be readily identified by comparison to these sequences. As used herein, reference to a T-box domain of any Brachyury protein described herein or known in the art and utilized in the invention may include an additional 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 consecutive amino acids of the Brachyury sequence on the N-terminal and/or the C-terminal end of the defined T-box domain (e.g., on either side of positions 41-223 of SEQ ID NOs:2, 6 or 18). Human Brachyury, including the two human Brachyury proteins described herein, also contains various CD4+ and CD8+ T cell epitopes. Such epitopes have been described, for example, in WO 2008/106551, and include a CD8+ CTL epitope, WLLPGTSTL (also referred to herein as Tp2, SEQ ID NO:12), at positions 246 to 254 of SEQ ID NO:2 or SEQ ID NO:6. As discussed above, SEQ ID NO:18 comprises an agonist epitope of SEQ ID NO:12, represented herein by SEQ ID NO:13.

Human Brachyury has very high homology with Brachyury from other animal species and therefore, one is able to utilize the sequences of Brachyury from other organisms in the preparation of a yeast-Brachyury immunotherapeutic composition of the invention, particularly where these sequences are identical, substantially homologous, and elicit an effective immune response against the target antigen (e.g., native Brachyury expressed by a tumor cell). For example, murine Brachyury, which was first cloned by Hermann and colleagues in 1990 (Hermann et al., supra) is approximately 85% identical to human Brachyury at the nucleotide level, and approximately 91% identical at the amino acid level. With respect to Brachyury from other animals, at the amino acid level, human Brachyury is 99.5% identical to Brachyury from Pan troglodytes, 90.1% identical to Brachyury from *Canis lupus familiaris*, 88.5% identical to Brachyury from *Bos Taurus*, 92.2% identical to Brachyury from *Rattus norvegicus*, and 80.9% identical to Brachyury from *Gallus gallus*. Within amino acids 1-223 of Brachyury, which contains the T-box domain, mouse and human Brachyury differ by only two amino acids (at positions 26 and 96). A nucleotide sequence encoding murine Brachyury is represented herein by SEQ ID NO:3, which is an mRNA sequence that was obtained from GENBANK® Accession No. NM_009309 (GI:118130357). SEQ ID NO:3 encodes a 436 amino acid murine Brachyury protein, the amino acid sequence of which is represented here as SEQ ID NO:4. Positions 41 to 223 of SEQ ID NO:4 represent the T-box DNA binding domain of murine Brachyury.

In one embodiment of the invention, a Brachyury antigen comprises or consists of the amino acid sequence represented by SEQ ID NO:2, SEQ ID NO:4, SEQ ID NO:6, SEQ ID NO:18, or at least one immunogenic domain thereof. In one embodiment, a Brachyury antigen comprises or consists of two, three, four, five, or more immunogenic domains of Brachyury. In one embodiment of the invention, a Brachyury antigen comprises or consists of the amino acid sequence represented by amino acid positions 1 or 2 through one of the last 25 amino acids at the C-terminus of SEQ ID NO:2, SEQ ID NO:4, SEQ ID NO:6 or SEQ ID NO:18 (i.e., through any one of positions 441 to 435 of SEQ ID NO:2 or SEQ ID NO:6 or SEQ ID NO:18, or through any one of positions 442 to 436 of SEQ ID NO:4). Another Brachyury antigen useful in the invention also includes at least amino acid positions 1-223 of Brachyury (e.g., positions 1-223 of SEQ ID NO:2, SEQ ID NO:4, SEQ ID NO:6 or SEQ ID NO:18) or positions 41-223 of Brachyury (e.g., positions 41-223 of SEQ ID NO:2, SEQ ID NO:4, SEQ ID NO:6 or SEQ ID NO:18). Another Brachyury antigen useful in the invention includes from at least amino acid positions 1 to 85 to between position 255 and the C-terminus of SEQ ID NO:2, SEQ ID NO:4, SEQ ID NO:6 or SEQ ID NO:18. Another Brachyury antigen useful in the invention includes from at least amino acid positions 1 to 85 to between position 430 and the C-terminus of SEQ ID NO:2, SEQ ID NO:4, SEQ ID NO:6 or SEQ ID NO:18. Another Brachyury antigen useful in the invention includes from at least amino acid positions 1, 2, 3, 4, 5, 6, 7, 8, 9 or 10 to between position 255 and the C-terminus of SEQ ID NO:2, SEQ ID NO:4, SEQ ID NO:6 or SEQ ID NO:18.

According to any embodiment of the present invention, reference to a "full-length" protein (or a full-length functional domain or full-length immunological domain) includes the full-length amino acid sequence of the protein or functional or immunological domain, as described herein or as otherwise known or described in a publicly available sequence. A protein or domain that is "near full-length", which is also a type of homologue of a protein, differs from a full-length protein or domain, by the addition or deletion or omission of 1, 2, 3, 4, 5, 6, 7, 8, 9, or 10 amino acids from the N- and/or C-terminus of such a full-length protein or full-length domain. By way of example, several of the fusion proteins described herein comprise a "near full-length" Brachyury antigen since the antigen omits the methionine at position 1 and substitutes an N-terminal peptide. General reference to a protein or domain or antigen can include both full-length and near full-length proteins, as well as other homologues thereof.

In one aspect of any embodiments related to an antigen for use in the method to treat or prevent chordoma, a cancer antigen (chordoma antigen) is of a minimum size sufficient to allow the antigen to be expressed by yeast. For expression in yeast, a protein is typically at least about 25 amino acids in length, although smaller proteins may be expressed, and considerably larger proteins may be expressed by yeast. For example, a Brachyury antigen useful in the invention is a fragment of a Brachyury protein that can be expressed recombinantly by yeast and that contains at least one immunogenic domain of Brachyury, which could include at least one immunogenic domain of any of SEQ ID NO:2, SEQ ID NO:4, SEQ ID NO:6 or SEQ ID NO:18. In one aspect, such an antigen is at least 25 amino acids in length, and contains at least one immunogenic domain of a chordoma antigen, such as Brachyury. In one aspect, such an antigen is greater than 30 amino acids in length, and contains at least one immunogenic domain of the cancer antigen. In one aspect, such an antigen is at least 25-50 amino acids in length, and contains at least one immunogenic domain of the cancer antigen. In one aspect, such an antigen is at least 30-50 amino acids in length, and contains at least one immunogenic domain of the cancer antigen. In one aspect, such an antigen is at least 35-50 amino acids in length, and contains at least one immunogenic domain of the cancer antigen. In one aspect, such an antigen is at least 40-50 amino acids in length, and contains at least one immunogenic domain of the cancer antigen. In one aspect, such an antigen is at least 45-50 amino acids in length, and contains at least one immunogenic domain of the cancer antigen. In one embodiment, the cancer antigen useful in the present invention is at least 25 amino acids in length, or at least: 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, or 430 amino acids in length, which, with respect to Brachyury antigens, can include any fragment of at least any of these lengths of SEQ ID NO:2, SEQ ID NO:4, SEQ ID NO:6 or SEQ ID NO:18.

In one aspect, an antigen useful in the methods of the invention comprises one or more CTL epitopes, which may include two or more copies of any one, two, three, or more of the CTL epitopes described herein. In one aspect, the antigen comprises one or more CD4$^+$ T cell epitopes. The T cell. In one aspect, the antigen comprises one or more CTL epitopes and one or more CD4$^+$ T cell epitopes. In one aspect, the T cell epitope is an agonist epitope.

In one aspect, a Brachyury antigen comprises an amino acid sequence of WLLPGTSTL (SEQ ID NO:12, also represented by positions 245 to 254 of SEQ ID NO:2 or SEQ ID NO:6). In one aspect, the Brachyury antigen comprises an amino acid sequence of WLLPGTSTV (SEQ ID NO:13, also represented by positions 245 to 254 of SEQ ID NO:18).

In one aspect, the amino acid at position 4 of either SEQ ID NO:12 or SEQ ID NO:13 (a proline or P in these sequences) is substituted with a serine (S), a threonine (T), an isoleucine (I), or a valine (V).

In one aspect, the Brachyury antigen comprises an amino acid sequence of SQYPSLWSV (SEQ ID NO:14). In one aspect, the amino acid at position 2 of SEQ ID NO:14 (a glutamine or Q in this sequence) is substituted with a leucine (L). In one aspect, the amino acid at position 4 of SEQ ID NO:14 (a proline or P in this sequence) is substituted with a serine (S), threonine (T), leucine (L), or valine (V). In one aspect, the amino acid at position 7 of SEQ ID NO:14 (a tryptophan or W in this sequence) is substituted with a valine (V), leucine (L), isoleucine (I), serine (S), or threonine (T). In one aspect, the amino acid at position 9 of SEQ ID NO:14 (a valine or V in this sequence) is substituted with a leucine (L). An antigen comprising a sequence having any combination of one or more of these substitutions in SEQ ID NO:14 is contemplated by the invention.

In one aspect, the Brachyury antigen comprises an amino acid sequence of RLIASWTPV (SEQ ID NO:15). In one aspect, the amino acid at position 1 of SEQ ID NO:15 (an arginine or R in this sequence) is substituted with a tyrosine (Y) or a tryptophan (W). In one aspect, the amino acid at position 6 of SEQ ID NO:15 (a tryptophan or W in this sequence) is substituted with a valine (V), a lysine (L), an isoleucine (I), a serine (S), or a threonine (T). An antigen comprising a sequence having any combination of one or both of these substitutions in SEQ ID NO:15 is contemplated by the invention.

In one aspect, the Brachyury antigen comprises an amino acid sequence of AMYSFLLDFV (SEQ ID NO:16). In one aspect, the amino acid at position 2 of SEQ ID NO:16 (a methionine or M in this sequence) is substituted with a leucine (L).

In one embodiment of the invention, a Brachyury antigen comprises, consists essentially of, or consists of a fusion protein having the amino acid sequence of SEQ ID NO:8. The fusion protein of SEQ ID NO:8 is a single polypeptide with the following sequence elements fused in frame from N- to C-terminus: (1) an N-terminal peptide to impart resistance to proteasomal degradation and stabilize expression in yeast (positions 1-6 of SEQ ID NO:8); (2) a human Brachyury antigen consisting of positions 2-435 of SEQ ID NO:6 (positions 7-440 of SEQ ID NO:8); and (3) a hexahistidine tag (positions 441-446 of SEQ ID NO:8). The amino acid sequence of SEQ ID NO:8 is encoded by the polynucleotide sequence of SEQ ID NO:7. The amino acid sequenced used in this fusion protein can be modified by the use of additional or alternate amino acids flanking either end of the Brachyury antigen, if desired, and shorter portions of the Brachyury may also be used.

In another embodiment of the invention, a Brachyury antigen comprises, consists essentially of, or consists of a fusion protein having the amino acid sequence of SEQ ID NO:10. The fusion protein of SEQ ID NO:10 is a single polypeptide with the following sequence elements fused in frame from N- to C-terminus: (1) an N-terminal peptide to impart resistance to proteasomal degradation and stabilize expression in yeast (positions 1-6 of SEQ ID NO:10); (2) a murine Brachyury antigen consisting of positions 2-436 of SEQ ID NO:4 (positions 7-441 of SEQ ID NO:10); and (3) a hexahistidine tag (positions 442-447 of SEQ ID NO:10). The amino acid sequence of SEQ ID NO:10 is encoded by the polynucleotide sequence of SEQ ID NO:9.

In another embodiment of the invention, a Brachyury antigen comprises, consists essentially of, or consists of a fusion protein having the amino acid sequence of SEQ ID NO:20. The fusion protein of SEQ ID NO:20 is a single polypeptide with the following sequence elements fused in frame from N- to C-terminus: (1) an N-terminal peptide to impart resistance to proteasomal degradation and stabilize expression (positions 1 to 6 of SEQ ID NO:20, the peptide sequence also represented herein by SEQ ID NO:11); 2) amino acids 2-435 of SEQ ID NO:18 (positions 7-440 of SEQ ID NO:20), SEQ ID NO:18 representing a full-length human Brachyury agonist protein; and (3) a hexahistidine tag (positions 441-446 of SEQ ID NO:20). The agonist epitope (SEQ ID NO:13) is located at positions 251 to 259 of SEQ ID NO:20 (positions 246 to 254 of SEQ ID NO:18). The amino acid sequence of SEQ ID NO:20 is encoded by the polynucleotide sequence of SEQ ID NO:19.

An antigen useful in a composition for use in a method according to the present invention also includes proteins having an amino acid sequence that is at least 85%, 86%, 87%, 88%, 89%, 90%, 91%, 92%, 93%, 94%, 95%, 96%, 97%, 98%, or 99% identical to the amino acid sequence of any of the cancer proteins or cancer antigens described herein over the full length of the protein, or with respect to a defined fragment or domain thereof (e.g., an immunological domain or functional domain (domain with at least one biological activity)) that forms part of the protein. For example, a domain of the Brachyury protein described herein includes the T-box domain. An immunological domain has been described in detail above.

In some aspects of the invention, amino acid insertions, deletions, and/or substitutions can be made for one, two, three, four, five, six, seven, eight, nine, ten, or more amino acids of a wild-type or reference protein, provided that the resulting protein, when used as an antigen in a yeast-based immunotherapeutic composition of the invention, elicits an immune response against a native protein as the wild-type or reference protein, which may include an enhanced immune response, a diminished immune response, or a substantially similar immune response. For example, the invention includes the use of agonist antigens, including Brachyury agonist antigens, which may include one or more T cell epitopes that have been mutated to enhance the T cell response against the agonist, such as by improving the avidity or affinity of the epitope for an MHC molecule or for the T cell receptor that recognizes the epitope in the context of MHC presentation. Antigen agonists may therefore improve the potency or efficiency of a T cell response against native antigen expressed by a tumor cell. The Brachyury antigen having the amino acid sequence of SEQ ID NO:18 is a non-limiting example of a Brachyury agonist (or a Brachyury antigen comprising an agonist epitope).

In addition, N-terminal expression sequences and the C-terminal tags, such as those described above with respect to the fusion proteins of SEQ ID NO:8, SEQ ID NO:10, or SEQ ID NO:20 are optional, but may be selected from several different sequences described elsewhere herein to improve or assist with expression, stability, and/or allow for identification and/or purification of the protein. Also, many different promoters suitable for use in yeast are known in the art. Furthermore, short intervening linker sequences (e.g., 1, 2, 3, 4, or 5 amino acid peptides) may be introduced between portions of a fusion protein comprising a cancer antigen for a variety of reasons, including the introduction of restriction enzyme sites to facilitate cloning, as cleavage sites for host phagosomal proteases, to accelerate protein or antigen processing, and for future manipulation of the constructs.

Optionally, proteins, including fusion proteins, which are used as a component of the yeast-based immunotherapeutic composition of the invention are produced using antigen constructs that are particularly useful for improving or stabilizing the expression of heterologous antigens in yeast. In one embodiment, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, including but not limited to yeast alpha factor leader sequence, wherein either fusion partner provides improved stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). In addition, the present invention optionally includes the use of peptides that are fused to the C-terminus of the antigen-encoding construct, particularly for use in the selection and identification of the protein. Such peptides include, but are not limited to, any synthetic or natural peptide, such as a peptide tag (e.g., 6× His or hexapeptide) or any other short epitope tag. Peptides attached to the C-terminus of an antigen according to the invention can be used with or without the addition of the N-terminal peptides discussed above, and vice versa.

In one embodiment, a fusion protein comprises an amino acid sequence of M-X2-X3-X4-X5-X6, wherein M is methionine; wherein X2 is any amino acid except glycine, proline, lysine or arginine; wherein X3 is any amino acid except methionine, lysine or arginine; wherein X4 is any amino acid except methionine, lysine or arginine; wherein X5 is any amino acid except methionine, lysine or arginine; and wherein X6 is any amino acid except methionine, lysine or arginine. In one embodiment, the X6 residue is a proline. An exemplary synthetic sequence that enhances the stability of expression of an antigen in a yeast cell and/or prevents post-translational modification of the protein in the yeast includes the sequence M-A-D-E-A-P (represented herein by SEQ ID NO:11). In addition to the enhanced stability of the expression product, this fusion partner does not appear to negatively impact the immune response against the immunizing antigen in the construct. In addition, the synthetic fusion peptides can be designed to provide an epitope that can be recognized by a selection agent, such as an antibody.

Methods of producing yeast vehicles and expressing, combining and/or associating yeast vehicles with antigens and/or other proteins and/or agents of interest to produce yeast-based immunotherapy compositions are contemplated by the invention.

According to the present invention, the term "yeast vehicle-antigen complex" or "yeast-antigen complex" is used generically to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transfected with a heterologous nucleic acid molecule encoding a protein (e.g., the antigen) such that the protein is expressed by the yeast cell. Such a yeast is also referred to herein as a recombinant yeast or a recombinant yeast vehicle. The yeast cell can then be formulated with a pharmaceutically acceptable excipient and administered directly to a patient, stored for later administration, or loaded into a dendritic cell as an intact cell. The yeast cell can also be killed, or it can be derivatized such as by formation of yeast spheroplasts, cytoplasts, ghosts, or subcellular particles, any of which may be followed by storing, administering, or loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses the antigen. Yeast cells or yeast spheroplasts that recombinantly express the antigen(s) may be used to produce a yeast vehicle comprising a yeast cytoplast, a yeast ghost, or a yeast membrane particle or yeast cell wall particle, or fraction thereof.

In general, the yeast vehicle and antigen(s) and/or other agents can be associated by any technique described herein. In one aspect, the yeast vehicle was loaded intracellularly with the antigen(s) and/or agent(s). In another aspect, the antigen(s) and/or agent(s) was covalently or non-covalently attached to the yeast vehicle. In yet another aspect, the yeast vehicle and the antigen(s) and/or agent(s) were associated by mixing. In another aspect, and in one embodiment, the antigen(s) and/or agent(s) are expressed recombinantly by the yeast vehicle or by the yeast cell or yeast spheroplast from which the yeast vehicle was derived.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 antigens and or other proteins.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SECT) and acid phosphatase (PHO5), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule can be introduced into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego). For example, under one protocol, liquid cultures containing a suitable medium can be inoculated using cultures obtained from starter plates and/or starter cultures of yeast-Brachyury immunotherapy compositions, and are grown for approximately 20 h at 30° C., with agitation at 250 rpm. Primary cultures can then be expanded into larger cultures as desired. Protein expression from vectors with which the yeast were transformed (e.g., Brachyury expression) may be constitutive if the promoter utilized is a constitutive promoter, or may be induced by addition of the appropriate induction conditions for the promoter if the promoter utilized is an inducible promoter (e.g., copper sulfate in the case of the CUP1 promoter). In the case of an inducible promoter, induction of protein expression may be initiated after the culture has grown to a suitable cell density, which may be at about 0.2 Y.U./ml or higher densities.

In one aspect of the invention, a yeast-Brachyury immunotherapy composition useful in the present invention is the yeast-Brachyury immunotherapy composition comprising a *Saccharomyces cerevisiae* yeast expressing a polynucleotide encoding the human Brachyury fusion protein represented by SEQ ID NO:8 under the control of the CUP1 promoter is also referred to herein as GI-6301. In another aspect, a yeast-Brachyury immunotherapy composition useful in the present invention is the yeast-Brachyury immunotherapy composition comprising a *Saccharomyces cerevisiae* yeast expressing a polynucleotide encoding the human Brachyury fusion protein represented by SEQ ID NO:8 under the control of the TEF2 promoter (in vector plu011) is also referred to herein as GI-6302. In another aspect, a yeast-Brachyury immunotherapy composition useful in the present invention is the yeast-Brachyury immunotherapy composition comprising a *Saccharomyces cerevisiae* yeast expressing a polynucleotide encoding the human Brachyury fusion protein represented by SEQ ID NO:8 under the control of the TEF2 promoter (in vector pGI-172) is also referred herein as GI-6303. In yet another aspect, a yeast-Brachyury immunotherapy composition useful in the present invention is the yeast-Brachyury immunotherapy composition comprising a *Saccharomyces cerevisiae* yeast expressing a polynucleotide encoding the human Brachyury agonist fusion protein represented by SEQ ID NO:20 under the control of the CUP1 promoter is also referred to herein as GI-6305.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to an individual or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

When the antigen or other protein is expressed on or physically attached to the surface of the yeast, spacer arms may, in one aspect, be carefully selected to optimize antigen or other protein expression or content on the surface. The size of the spacer arm(s) can affect how much of the antigen or other protein is exposed for binding on the surface of the yeast. Thus, depending on which antigen(s) or other protein(s) are being used, one of skill in the art will select a spacer arm that effectuates appropriate spacing for the antigen or other protein on the yeast surface. In one embodiment, the spacer arm is a yeast protein of at least 450 amino acids. Spacer arms have been discussed in detail above.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens, viral vector vaccines) to enhance immune responses. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include additional agents, which may also be referred to as biological response modifier compounds, or the ability to produce such agents/modifiers. For example, a yeast vehicle can be transfected with or loaded with at least one antigen and at least one agent/biological response modifier compound, or a composition of the invention can be administered in conjunction with at least one agent/biological response modifier. Biological response modifiers include adjuvants and other compounds that can modulate immune responses, which may be referred to as immunomodulatory compounds, as well as compounds that modify the biological activity of another compound or agent, such as a yeast-based immunotherapeutic, such biological activity not being limited to immune system effects. Certain immunomodulatory compounds can stimulate a protective immune response whereas others can suppress a harmful immune response, and whether an immunomodulatory is useful in combination with a given yeast-based immunotherapeutic may depend, at least in part, on the disease state or condition to be treated or prevented, and/or on the individual who is to be treated. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa.). Certain biological response modifiers have one or more properties in common with the biological properties of yeast-based immunotherapeutics or enhance or complement the biological properties of yeast-based immunotherapeutics. There are a number of techniques known to those skilled in the art to measure stimulation or suppression of immune responses, as well as to differentiate cell-mediated immune responses from humoral immune responses, and to differentiate one type of cell-mediated response from another (e.g., a TH17 response versus a TH1 response).

Agents/biological response modifiers useful in the invention may include, but are not limited to, cytokines, chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein.

Agents can include agonists and antagonists of a given protein or peptide or domain thereof. As used herein, an "agonist" is any compound or agent, including without limitation small molecules, proteins, peptides, antibodies, nucleic acid binding agents, etc., that binds to a receptor or ligand and produces or triggers a response, which may include agents that mimic or enhance the action of a naturally occurring substance that binds to the receptor or ligand. An "antagonist" is any compound or agent, including without limitation small molecules, proteins, peptides, antibodies, nucleic acid binding agents, etc., that blocks or inhibits or reduces the action of an agonist.

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); Methods in yeast genetics: a laboratory course manual, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988), *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000); Casarett and Doull's *Toxicology The Basic Science of Poisons*, C. Klaassen, ed., 6th edition (2001), and *Vaccines*, S. Plotkin, W. Orenstein, and P. Offit, eds., Fifth Edition (2008).

GENERAL DEFINITIONS

A "TARMOGEN®" (GlobeImmune, Inc., Louisville, Colo.) generally refers to a yeast vehicle expressing one or more heterologous antigens extracellularly (on its surface), intracellularly (internally or cytosolically) or both extracellularly and intracellularly. TARMOGEN®s have been generally described (see, e.g., U.S. Pat. No. 5,830,463). Certain yeast-based immunotherapy compositions, and methods of making and generally using the same, are also described in detail, for example, in U.S. Pat. Nos. 5,830,463, 7,083,787, 7,736,642, Stubbs et al., *Nat. Med.* 7:625-629 (2001), Lu et al., *Cancer Research* 64:5084-5088 (2004), and in Bernstein et al., Vaccine 2008 Jan. 24; 26(4):509-21, each of which is incorporated herein by reference in its entirety.

In general, the term "biologically active" indicates that a compound (including a protein or peptide) has at least one detectable activity that has an effect on the metabolic, physiological, chemical, or other processes of a cell, a tissue, or an organism, as measured or observed in vivo (i.e., in a natural physiological environment) or in vitro (i.e., under laboratory conditions).

According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA, immunoblot assays, etc.).

General reference to a protein or polypeptide used in the present invention includes full-length proteins, near full-length proteins (defined above), or any fragment, domain (structural, functional, or immunogenic), conformational epitope, or a homologue or variant of a given protein. A fusion protein may also be generally referred to as a protein or polypeptide. An isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" or "variant" is used to refer to a protein or peptide which differs from a reference protein or peptide (i.e., the "prototype" or "wild-type" protein) by minor modifications to the reference protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue or variant can have enhanced, decreased, or substantially similar properties as compared to the reference protein or peptide. A homologue or variant can include an agonist of a protein or an antagonist of a protein. Homologues or variants can be produced using techniques known in the art for the production of proteins including, but not limited to, direct modifications to the isolated reference protein, direct protein synthesis, or modifications to the nucleic acid sequence encoding the protein using, for example, classic or recombinant DNA techniques to effect random or targeted mutagenesis, resulting in the encoding of a protein variant. In addition, naturally occurring variants of a reference protein may exist (e.g., isoforms, allelic variants, or other natural variants that may occur from individual to individual) and may be isolated, produced and/or utilized in the invention.

A homologue or variant of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 86% identical, or at least about 87% identical, or at least about 88% identical, or at least about 89% identical, or at least about 90%, or at least about 91% identical, or at least about 92% identical, or at least about 93% identical, or at least about 94% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein (e.g., an amino acid sequence specified herein, or the amino acid sequence of a specified protein). In one embodiment, the homologue or variant comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the amino acid sequence of the reference protein.

As used herein, unless otherwise specified, reference to a percent (%) identity refers to an evaluation of homology which is performed using: (1) a Basic Local Alignment Search Tool (BLAST) basic homology search using blastp for amino acid searches and blastn for nucleic acid searches with standard default parameters, wherein the query sequence is filtered for low complexity regions by default (such as described in Altschul, S. F., Madden, T. L., Schäaffer, A. A., Zhang, J., Zhang, Z., Miller, W. & Lipman, D. J. (1997) "Gapped BLAST and PSI-BLAST: a new generation of protein database search programs." *Nucleic Acids Res.* 25:3389-3402, incorporated herein by reference in its entirety); (2) a BLAST alignment of two sequences (e.g., using the parameters described below); (3) and/or PSI-BLAST with the standard default parameters (Position-Specific Iterated BLAST. It is noted that due to some differences in the standard parameters between Basic BLAST and BLAST for two sequences, two specific sequences might be recognized as having significant homology using the BLAST program, whereas a search performed in Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST as described in Tatusova and Madden, (1999), "Blast 2 sequences—a new tool for comparing protein and nucleotide sequences", FEMS Microbiol Lett. 174:247-250, incorporated herein by reference in its entirety. Such a sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST sequence alignment for two sequences is performed using the standard default parameters as follows.

For blastn, using 0 BLOSUM62 matrix:
Reward for match=1
Penalty for mismatch=−2
Open gap (5) and extension gap (2) penalties gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome or a segment of the genome containing more than one gene, in which the nucleic acid molecule is found in nature. An isolated nucleic acid molecule can include a complete gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule may also include portions of a gene. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a plasmid useful for transfecting yeast. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell, such as a yeast.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following example describes a phase 1 or phase 2 clinical trial in subjects with chordoma.

A randomized phase 1 or phase 2 clinical trial in patients with chordoma is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 or SEQ ID NO:20). At least 20 or more subjects with chordoma are enrolled.

The trial is run as a double-blind or open-label, placebo-controlled, multi-center trial. All patients receive standard of care therapy, which includes tumor resection and radiation therapy, with treatment arm patients receiving several serial injections of yeast-Brachyury immunotherapeutic composition during treatment. The primary endpoint is reduction in Brachyury-positive tumor cells, improved symptomatic and radiological responses, non-progression of tumor growth, recurrence free survival or overall survival. Additional endpoints can include antigen-specific T cell responses (e.g., Brachyury-specific CD8$^+$ T cells emerging or expanding on treatment).

The yeast-based immunotherapeutic composition is expected to be safe and well-tolerated with no significant toxicities. In addition, the yeast-Brachyury immunotherapeutic composition is expected to produce treatment-emergent Brachyury-specific T cell responses and/or an improvement in pre-existing Brachyury-specific baseline T cell responses in at least some or a majority of patients. Some or a majority of patients are also expected to have stabilized disease and/or have extended recurrence free survival (progression free survival) and/or overall survival.

Example 2

The following example describes a phase 2 clinical trial in healthy subjects with a history of familial chordoma.

A randomized phase 2 clinical trial in healthy subjects with a history of familial chordoma (i.e. subjects from a family with two or more blood relatives with a history of chordoma) is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 or SEQ ID NO:20). At least 40 or more subjects are enrolled.

The trial is run as a double-blind or open-label, placebo-controlled, multi-center trial. All patients receive routine monitoring, with treatment arm patients receiving several serial injections of yeast-Brachyury immunotherapeutic composition. Subjects are monitored for the occurrence of chordoma. Endpoints can include antigen-specific T cell responses (e.g., Brachyury-specific CD8$^+$ T cells emerging or expanding on treatment), maintenance of chordoma negativity, and delayed progression chordoma.

The yeast-based immunotherapeutic composition is expected to be safe and well-tolerated with no significant toxicities. In addition, the yeast-Brachyury immunotherapeutic composition is expected to produce treatment-emergent Brachyury-specific T cell responses in at least some or a majority of patients. The treatment group of subjects is expected to have a lower incidence of chordoma, or a delayed onset of chordoma, as compared to subjects receiving placebo or as compared to the population of subjects with a history of chordoma (i.e., familial chordoma) who have not received yeast-based immunotherapy. For purposes of comparison for determination of the effectiveness of treatment, the control can include a valid/referenced historical control rate for the occurrence of familial chordoma, such as may be determined by following family members from families with familial chordoma over time to provide a baseline reference for disease occurrence.

Example 3

The following example describes a phase 1 clinical trial conducted in subjects with cancers known to express Brachyury.

An open-label, sequential dose-escalation, phase 1 clinical trial was initiated using the yeast-Brachyury immunotherapy composition referred to as GI-6301. Under this clinical trial protocol, the key inclusion criteria included presence of a solid tumor, measurable disease (disease must be evaluable) or non-measurable disease, Eastern Cooperative Oncology Group (ECOG) status grade of 0-1 (wherein grade 0 indicates fully active, able to carry on all pre-disease performance without restriction and grade 1 indicates restricted in physically strenuous activity but ambulatory and able to carry work of a light or sedentary nature), creatinine levels of $\leq$/–1.5×ULN (upper limit of normal), ALT levels (alanine-aminotransferase) of $\leq$/–2.5×ULN, AST levels (aspartate aminotransferase) of $\leq$/–2.5×ULN, Bilirubin (Bili) levels of $\leq$/–1.5×ULN, absolute neutrophil count (ANC) of >1500, platelet count of >100,000, minimum of 2 weeks from prior chemotherapy treatment. In addition, patients that had prior immune therapy were allowed.

The key exclusion criteria included patients having HIV or hepatitis; pregnant women, breast feeding women, patients with an active autoimmune disease, some systemic steroid use, allergy to yeast based products, disease of the CNS, pericardial mass of >2 cm, EBV virmia (defined by PCR, log 10 value >3.0), thyroid disease (mass or autoimmune) and patients using tricyclic antidepressants.

27 patients (3-16 patients per dose cohort) with advanced cancers were enrolled and were administered the yeast-Brachyury immunotherapy composition known as GI-6301 in a sequential dose cohort escalation protocol. The protocol utilized dose ranges of 4 Y.U. (1 Y.U.×4 sites, meaning that 1 Y.U. of GI-6301 is administered at 4 different sites on the body of the patient each visit), 16 Y.U. (4 Y.U.×4 sites) and 40 Y.U. (10 Y.U.×4 sites), administered subcutaneously. GI-6301 was administered at 2 week intervals for a total of 7 visits (~3 months), and then monthly thereafter with restaging scans every 2 months while on study. The primary endpoint was safety. Secondary endpoints included analysis of tumor-associated antigen immune responses, i.e., whether a significant change in T cell precursors was detectable as measured by an increase in Brachyury-specific T cells in ELISpot assay and proliferation in response to Brachyury protein (e.g., Brachyury-specific CD8$^+$ or CD4$^+$ T cells emerging or expanding on treatment). Additional secondary endpoints included clinical benefits, such as progression-free survival, changes in tumor markers or rate of change, as well as parameters of general immune activation, including frequency of immune cell subsets in peripheral blood (CD8$^+$ memory/effector T cells, CD4$^+$ memory/effector T cells, Tregs, NK cells, DCs) and changes in serum levels of cytokines (e.g., IFN-$\gamma$, IL-10, IL-12, IL-2, IL-4, TGF-$\beta$, etc.). For example, immune response was measured by flow-cytometry intracellular staining (ICS) of CD4 and CD8 T lymphocytes for the cytokines interferon gamma (IFN-$\gamma$), tumor necrosis factor (TNF), and interleukin 2 (IL-2).

The treatment was well tolerated with 191 vaccine cycles given to the 27 patients. Two patients experienced grade 3 injection site reactions (transient). There were no other grade 3 and no grade 4 toxicities related to vaccine. Only nine cycles were associated with grade 2 toxicity (generally flu-like symptoms).

21 samples were available for immune response analysis with 7 samples demonstrating a Brachyury-specific response as measured by ICS. The median time on study was 74 days (range). A patient with metastatic colon cancer had stable disease for 15 months.

Overall, the immunotherapeutic composition, GI-6301 was found to be safe and well-tolerated with no significant toxicities. This phase 1 study with GI-6301 immunotherapy composition demonstrated safety and enhanced immune response in some patients. These results demonstrate, for the first time in a human, that a transcription factor can be targeted immunologically via vaccination.

Example 4

The following example describes an expansion of the Phase 1 study described in Example 3 showing results from immunization of subjects with chordoma using a yeast-Brachyury composition of the invention.

An expansion phase of the Phase 1 study described in Example 3 was initiated. The goal of the expansion phase was to administer GI-6301 at the highest tolerated dose to an additional cohort of patients, and to include advanced chordoma patients in the study. To enroll the expansion phase, the following eligibility criteria were removed as compared to the initial study described in Example 3: exclusion of CNS disease (specifically to allow for chordoma patients to enroll), thyroid disease (and monitoring) and Epstein-Barr virus (EBV) PCR requirements.

Seven patients with recurrent (advanced) chordoma were enrolled onto the 40 Y.U. dose level expansion phase and the clinical and immunological outcomes of these patients have been initially evaluated. All seven patients had undergone previous radiation (median 470 days since radiation: range 111-1883). Median age was 59 (41-66). All received 40 Y.U. of vaccine every 2 weeks×7 with first restaging at day 8. If stable, patients went on to monthly dosing with restaging scans every 2 months. The primary endpoint was safety, but clinical outcomes were followed as well. Brachyury-specific T cell responses were also analyzed by flow-cytometry intracellular staining (ICS) of CD4 and CD8 T lymphocytes for the cytokines IFN-γ, TNF, and IL-2.

As discussed above, all 7 patients had undergone extensive previous treatment. Two patients had relatively stable disease for 6 and 12 months, respectively, coming on the study, and both remained stable at day 141 and 197 restaging, respectively. The remaining 5 patients had progressive disease at enrollment. Of those 5, 1 had a decrease in index lesions >30% at day 141 and had a confirmed partial response (PR) on repeat scan 4 weeks later. 1 patient has stable disease through day 141 restaging. The other 3 progressed at day 141 restaging. Adverse events were minimal with injection site reaction being the most common (13 events in 63 doses (21%), 6 of 7 pts (86%)). Two of 7 pts had a Brachyury-specific T cell response by ICS.

In the 40 Y.U. expansion group, tumor measurement changes were recorded as seen in FIG. 4. The x-axis scale on the left side of day zero is different than the scale on the right side of day zero.

To date, this cohort of patients with advanced Chordoma in the phase I study with GI-6301 vaccine demonstrated safety and enhanced immune response with a confirmed partial response (PR).

4-5 patients with recurrent chordoma have been scheduled to enter an 80 Y.U. dose level expansion phase.

Example 5

The following example describes a phase 2 clinical trial in chordoma subjects with locally recurrent or metastatic disease with tumor progression occurring between 3 and 9 months prior to enrollment in the trial.

This clinical study evaluates a yeast-Brachyury immunotherapeutic composition in chordoma subjects with locally recurrent or metastatic disease. Subjects who have received any prior line of therapy are accepted into the study. In addition, to be included in the study, the subject must have tumor progression that occurred between 3 and 9 months prior to enrollment in the study. The subjects receive the yeast-based immunotherapeutic composition, e.g., GI-6301, as described herein. For example, the protocol can utilize dose ranges of 4 Y.U. (1 Y.U.×4 sites, meaning that 1 Y.U. of GI-6301 is administered at 4 different sites on the body of the patient each visit), 16 Y.U. (4 Y.U.×4 sites), 40 Y.U. (10 Y.U.×4 sites), as well as 80 Y.U. (administered subcutaneously).

At approximately 6 months after initiation of the immunotherapeutic composition immunizations, the subjects will be evaluated by a care provider to determine if they have a lesion that can be irradiated. If a lesion can be irradiated, the lesion will be treated with radiation therapy and the subject will be monitored and evaluated until the primary and secondary endpoints of the trial are reached. If no lesion can be irradiated, the subject will not receive radiation therapy and will be monitored and evaluated until the primary and secondary endpoints of the trial are reached. Administration of the yeast-based immunotherapeutic composition continues during this time until the primary and secondary endpoints of the trial are reached.

The primary endpoint will be the determination of progression free survival (PFS) as defined by RECIST. The secondary endpoints include tumor response rate (defined by RECIST and Choi, and evaluated in irradiated and non-irradiated lesions for comparison) and tumor growth rate kinetics (evaluated at 6 months prior to immunotherapeutic treatment vs. 6 months after immunotherapeutic treatment). For PFS, the median is expected to be 9 months as compared to non-treated control subjects (expected 5 months). The subject's response to the immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

Administration of the yeast-Brachyury composition is expected to be safe and well-tolerated in this study with no significant toxicities. In addition, administration of the yeast-Brachyury composition is expected to improve progression free survival as compared to the standard median PFS for this category of subjects receiving standard of care, and the improvement in PFS is expected to be enhanced by additional radiation treatment post-vaccine. In addition, administration of the yeast-Brachyury composition is expected to improve response rates and favorably change tumor growth rate kinetics. Finally, administration of the yeast-Brachyury composition is expected to produce treatment-emergent Brachyury-specific T cell responses in at least some or a majority of patients.

Example 6

The following example describes a phase 2 clinical trial in chordoma subjects having a non-resectable, locally recurring lesion, wherein the lesion has not been previously irradiated.

A randomized phase 2 clinical trial in these chordoma subjects is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 (GI-6301) or SEQ ID NO:20 (GI-6305). The trial will be statistically powered to enroll the appropriate number of patients to evaluate clinical efficacy using the criteria described below.

The trial is run as a double-blind or open-label, multi-center trial. All patients receive routine monitoring and/or standard of care treatments of radiation therapy, systemic drug therapy or a combination thereof with treatment arm patients receiving several serial injections of yeast-Brachyury immunotherapeutic composition (i.e. GI-6301 or other yeast-Brachyury immunotherapeutics). For example, the protocol can utilize dose ranges of 4 Y.U. (1 Y.U.×4 sites, meaning that 1 Y.U. of GI-6301 is administered at 4 different sites on the body of the patient each visit), 16 Y.U. (4 Y.U.×4 sites), 40 Y.U. (10 Y.U.×4 sites), as well as 80 Y.U. (administered subcutaneously). The dose can be administered for example, as described in Example 3 or monthly. Inclusion criteria can include presence of a solid tumor and measurable disease. Primary and/or secondary endpoints can include progression free survival (may be defined by RECIST, or may be defined by immune related response criteria modified for RECIST, or by Choi criteria), delayed time to progression, tumor response rate (i.e. radiographic response defined by 6 to 12 months prior to enrollment by imaging of an untreated tumor during the time period, stability or progression as measured by RECIST and/or Choi criteria and/or compared to non-irradiated lesions in the subject), change in tumor growth rate kinetics (such as 6 months pre-treatment versus 6 months post-treatment), antigen-specific T cell responses (e.g., Brachyury-specific $CD8^+$ and/or $CD4^+$ T cells emerging or expanding on treatment), overall survival or combinations thereof.

The subject's response to the yeast-based immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

The yeast-based immunotherapeutic composition is expected to be safe and well-tolerated with no significant toxicities. In addition, the yeast-Brachyury immunotherapeutic composition is expected to improve progression free survival, produce treatment-emergent Brachyury-specific T cell responses in at least some or a majority of patients and/or reduce tumor growth rate. The treatment group of subjects is expected to have a delayed time to progression, as compared to the control subjects who have not received yeast-based immunotherapy. A goal of the study is to achieve a trending toward, and preferably a statistical significant increase in the median PFS from the expected median PFS of the chordoma population disclosed in this example. By way of illustration, a statistical goal of a median PFS of 9 months may be achieved, wherein for the relevant chordoma population under study, the expected median PFS may be typically about 5 months.

Example 7

The following example describes a phase 2 clinical trial in chordoma subjects having a non-resectable, locally recurring lesion, wherein the lesion has been previously irradiated.

A randomized phase 2 clinical trial in these chordoma subjects is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 (GI-6301) or SEQ ID NO:20 (GI-6305). The trial will be statistically powered to enroll the appropriate number of patients to evaluate clinical efficacy using the criteria described below.

The trial is run as a double-blind or open-label, multi-center trial. All patients receive routine monitoring and/or standard of care treatments of radiation therapy, systemic drug therapy or a combination thereof with treatment arm patients receiving several serial injections of yeast-Brachyury immunotherapeutic composition (i.e. GI-6301 or other yeast-Brachyury immunotherapeutics). For example, the protocol can utilize dose ranges of 4 Y.U. (1 Y.U.×4 sites, meaning that 1 Y.U. of GI-6301 is administered at 4 different sites on the body of the patient each visit), 16 Y.U. (4 Y.U.×4 sites), 40 Y.U. (10 Y.U.×4 sites), as well as 80 Y.U. (administered subcutaneously). The dose can be administered for example, as described in Example 3 or monthly. Inclusion criteria can include presence of a solid tumor and measurable disease. Primary and/or secondary endpoints can include progression free survival (may be defined by RECIST, or may be defined by immune related response criteria modified for RECIST, or by Choi criteria), delayed time to progression, tumor response rate (i.e. radiographic response defined by 6 to 12 months prior to enrollment by imaging of an untreated tumor during the time period, stability or progression as measured by RECIST and/or Choi criteria and/or compared to non-irradiated lesions in the subject), change in tumor growth rate kinetics (such as 6 months pre-treatment versus 6 months post-treatment), antigen-specific T cell responses (e.g., Brachyury-specific $CD8^+$ and/or $CD4^+$ T cells emerging or expanding on treatment), overall survival or combinations thereof.

The subject's response to the yeast-based immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

The yeast-based immunotherapeutic composition is expected to be safe and well-tolerated with no significant toxicities. In addition, the yeast-Brachyury immunotherapeutic composition is expected to improve progression free survival, produce treatment-emergent Brachyury-specific T cell responses in at least some or a majority of patients and/or reduce tumor growth rate. The treatment group of subjects is expected to have a delayed time to progression, as compared to the control subjects who have not received yeast-based immunotherapy. A goal of the study is to achieve a trending toward, and preferably a statistical significant increase in the median PFS from the expected median PFS of the chordoma population disclosed in this example. By way of illustration, a statistical goal of a median PFS of 9 months may be achieved, wherein for the relevant chordoma population under study, the expected median PFS may be typically about 5 months.

Example 8

The following example describes a phase 2 clinical trial in chordoma subjects having oligometastatic disease and a non-resectable lesion, wherein the lesion has not been previously irradiated.

A randomized phase 2 clinical trial in these chordoma subjects is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 (GI-6301) or SEQ ID NO:20 (GI-6305). The trial will be statistically powered to enroll the appropriate number of patients to evaluate clinical efficacy using the criteria described below.

The trial is run as a double-blind or open-label, multi-center trial. All patients receive routine monitoring and/or standard of care treatments of radiation therapy, systemic drug therapy or a combination thereof with treatment arm patients receiving several serial injections of yeast-Brachyury immunotherapeutic composition (i.e. GI-6301 or other yeast-Brachyury immunotherapeutics). For example, the protocol can utilize dose ranges of 4 Y.U. (1 Y.U.×4 sites, meaning that 1 Y.U. of GI-6301 is administered at 4 different sites on the body of the patient each visit), 16 Y.U. (4 Y.U.×4 sites), 40 Y.U. (10 Y.U.×4 sites), as well as 80 Y.U. (administered subcutaneously). The dose can be administered for example, as described in Example 3 or monthly. Inclusion criteria can include presence of a solid tumor and measurable disease. Primary and/or secondary endpoints can include progression free survival (may be defined by RECIST, or may be defined by immune related response criteria modified for RECIST, or by Choi criteria), delayed time to progression, tumor response rate (i.e. radiographic response defined by 6 to 12 months prior to enrollment by imaging of an untreated tumor during the time period, stability or progression as measured by RECIST and/or Choi criteria and/or compared to non-irradiated lesions in the subject), change in tumor growth rate kinetics (such as 6 months pre-treatment versus 6 months post-treatment), antigen-specific T cell responses (e.g., Brachyury-specific $CD8^+$ and/or $CD4^+$ T cells emerging or expanding on treatment), overall survival or combinations thereof.

The subject's response to the yeast-based immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

The yeast-based immunotherapeutic composition is expected to be safe and well-tolerated with no significant toxicities. In addition, the yeast-Brachyury immunotherapeutic composition is expected to improve progression free survival, produce treatment-emergent Brachyury-specific T cell responses in at least some or a majority of patients and/or reduce tumor growth rate. The treatment group of subjects is expected to have a delayed time to progression, as compared to the control subjects who have not received yeast-based immunotherapy. A goal of the study is to achieve a trending toward, and preferably a statistical significant increase in the median PFS from the expected median PFS of the chordoma population disclosed in this example. By way of illustration, a statistical goal of a median PFS of 9 months may be achieved, wherein for the relevant chordoma population under study, the expected median PFS may be typically about 5 months.

Example 9

The following example describes a phase 2 clinical trial in chordoma subjects having oligometastatic disease and a non-resectable lesion, wherein the lesion has been previously irradiated.

A randomized phase 2 clinical trial in these chordoma subjects is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 (GI-6301) or SEQ ID NO:20 (GI-6305). The trial will be statistically powered to enroll the appropriate number of patients to evaluate clinical efficacy using the criteria described below.

The trial is run as a double-blind or open-label, multi-center trial. All patients receive routine monitoring and/or standard of care treatments of radiation therapy, systemic drug therapy or a combination thereof with treatment arm patients receiving several serial injections of yeast-Brachyury immunotherapeutic composition (i.e. GI-6301 or other yeast-Brachyury immunotherapeutics). For example, the protocol can utilize dose ranges of 4 Y.U. (1 Y.U.×4 sites, meaning that 1 Y.U. of GI-6301 is administered at 4 different sites on the body of the patient each visit), 16 Y.U. (4 Y.U.×4 sites), 40 Y.U. (10 Y.U.×4 sites), as well as 80 Y.U. (administered subcutaneously). The dose can be administered for example, as described in Example 3 or monthly. Inclusion criteria can include presence of a solid tumor and measurable disease. Primary and/or secondary endpoints can include progression free survival (may be defined by RECIST, or may be defined by immune related response criteria modified for RECIST, or by Choi criteria), delayed time to progression, tumor response rate (i.e. radiographic response defined by 6 to 12 months prior to enrollment by imaging of an untreated tumor during the time period, stability or progression as measured by RECIST and/or Choi criteria and/or compared to non-irradiated lesions in the subject), change in tumor growth rate kinetics (such as 6 months pre-treatment versus 6 months post-treatment), antigen-specific T cell responses (e.g., Brachyury-specific $CD8^+$ and/or $CD4^+$ T cells emerging or expanding on treatment), overall survival or combinations thereof.

The subject's response to the yeast-based immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

The yeast-based immunotherapeutic composition is expected to be safe and well-tolerated with no significant toxicities. In addition, the yeast-Brachyury immunotherapeutic composition is expected to improve progression free survival, produce treatment-emergent Brachyury-specific T cell responses in at least some or a majority of patients and/or reduce tumor growth rate. The treatment group of subjects is expected to have a delayed time to progression, as compared to the control subjects who have not received yeast-based immunotherapy. A goal of the study is to achieve a trending toward, and preferably a statistical significant increase in the median PFS from the expected median PFS of the chordoma population disclosed in this example. By way of illustration, a statistical goal of a median PFS of 9 months may be achieved, wherein for the relevant chordoma population under study, the expected median PFS may be typically about 5 months.

Example 10

The following example describes a phase 2 clinical trial in chordoma subjects having oligometastatic disease and a post-resectable lesion, wherein the subject has not previously received radiation therapy for chordoma.

A randomized phase 2 clinical trial in these chordoma subjects is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 (GI-6301) or SEQ ID NO:20 (GI-6305). The trial will be statistically powered to enroll the appropriate number of patients to evaluate clinical efficacy using the criteria described below.

The trial is run as a double-blind or open-label, multi-center trial. All patients receive routine monitoring and/or standard of care treatments of radiation therapy, systemic drug therapy or a combination thereof with treatment arm patients receiving several serial injections of yeast-Brachyury immunotherapeutic composition (i.e. GI-6301 or other yeast-Brachyury immunotherapeutics). For example, the protocol can utilize dose ranges of 4 Y.U. (1 Y.U.×4 sites, meaning that 1 Y.U. of GI-6301 is administered at 4 different sites on the body of the patient each visit), 16 Y.U. (4 Y.U.×4 sites), 40 Y.U. (10 Y.U.×4 sites), as well as 80 Y.U. (administered subcutaneously). The dose can be administered for example, as described in Example 3 or monthly. Inclusion criteria can include presence of a solid tumor and measurable disease. Primary and/or secondary endpoints can include progression free survival (may be defined by RECIST, or may be defined by immune related response criteria modified for RECIST, or by Choi criteria), delayed time to progression, tumor response rate (i.e. radiographic response defined by 6 to 12 months prior to enrollment by imaging of an untreated tumor during the time period, stability or progression as measured by RECIST and/or Choi criteria and/or compared to non-irradiated lesions in the subject), change in tumor growth rate kinetics (such as 6 months pre-treatment versus 6 months post-treatment), antigen-specific T cell responses (e.g., Brachyury-specific $CD8^+$ and/or $CD4^+$ T cells emerging or expanding on treatment), overall survival or combinations thereof.

The subject's response to the yeast-based immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

The yeast-based immunotherapeutic composition is expected to be safe and well-tolerated with no significant toxicities. In addition, the yeast-Brachyury immunotherapeutic composition is expected to improve progression free survival, produce treatment-emergent Brachyury-specific T cell responses in at least some or a majority of patients and/or reduce tumor growth rate. The treatment group of subjects is expected to have a delayed time to progression, as compared to the control subjects who have not received yeast-based immunotherapy. A goal of the study is to achieve a trending toward, and preferably a statistical significant increase in the median PFS from the expected median PFS of the chordoma population disclosed in this example. By way of illustration, a statistical goal of a median PFS of 9 months may be achieved, wherein for the relevant chordoma population under study, the expected median PFS may be typically about 5 months.

Example 11

The following example describes a phase 2 clinical trial in chordoma subjects having oligometastatic disease and a post-resectable lesion, wherein the subject has previously received radiation therapy.

A randomized phase 2 clinical trial in these chordoma subjects is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 (GI-6301) or SEQ ID NO:20 (GI-6305). The trial will be statistically powered to enroll the appropriate number of patients to evaluate clinical efficacy using the criteria described below.

The trial is run as a double-blind or open-label, multi-center trial. All patients receive routine monitoring and/or standard of care treatments of radiation therapy, systemic drug therapy or a combination thereof with treatment arm patients receiving several serial injections of yeast-Brachyury immunotherapeutic composition (i.e. GI-6301 or other yeast-Brachyury immunotherapeutics). For example, the protocol can utilize dose ranges of 4 Y.U. (1 Y.U.×4 sites, meaning that 1 Y.U. of GI-6301 is administered at 4 different sites on the body of the patient each visit), 16 Y.U. (4 Y.U.×4 sites), 40 Y.U. (10 Y.U.×4 sites), as well as 80 Y.U. (administered subcutaneously). The dose can be administered for example, as described in Example 3 or monthly. Inclusion criteria can include presence of a solid tumor and measurable disease. Primary and/or secondary endpoints can include progression free survival (may be defined by RECIST, or may be defined by immune related response criteria modified for RECIST, or by Choi criteria), delayed time to progression, tumor response rate (i.e. radiographic response defined by 6 to 12 months prior to enrollment by imaging of an untreated tumor during the time period, stability or progression as measured by RECIST and/or Choi criteria and/or compared to non-irradiated lesions in the subject), change in tumor growth rate kinetics (such as 6 months pre-treatment versus 6 months post-treatment), antigen-specific T cell responses (e.g., Brachyury-specific $CD8^+$ and/or $CD4^+$ T cells emerging or expanding on treatment), overall survival or combinations thereof.

The subject's response to the yeast-based immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

The yeast-based immunotherapeutic composition is expected to be safe and well-tolerated with no significant toxicities. In addition, the yeast-Brachyury immunotherapeutic composition is expected to improve progression free survival, produce treatment-emergent Brachyury-specific T cell responses in at least some or a majority of patients and/or reduce tumor growth rate. The treatment group of subjects is expected to have a delayed time to progression, as compared to the control subjects who have not received yeast-based immunotherapy. A goal of the study is to achieve a trending toward, and preferably a statistical significant increase in the median PFS from the expected median PFS of the chordoma population disclosed in this example. By way of illustration, a statistical goal of a median PFS of 9 months may be achieved, wherein for the relevant chordoma population under study, the expected median PFS may be typically about 5 months.

Example 12

The following example describes a phase 2 clinical trial in chordoma subjects having a first recurrence of a non-resectable lesion, wherein the lesion has not been previously irradiated.

A randomized phase 2 clinical trial in these chordoma subjects is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 (GI-6301) or SEQ ID NO:20 (GI-6305). The trial will be statistically powered to enroll the appropriate number of patients to evaluate clinical efficacy using the criteria described below.

The trial is run as a double-blind or open-label, multi-center trial. All patients receive routine monitoring and/or standard of care treatments of radiation therapy, systemic drug therapy or a combination thereof with treatment arm patients receiving several serial injections of yeast-Brachyury immunotherapeutic composition (i.e. GI-6301 or other yeast-Brachyury immunotherapeutics). For example, the protocol can utilize dose ranges of 4 Y.U. (1 Y.U.×4 sites, meaning that 1 Y.U. of GI-6301 is administered at 4 different sites on the body of the patient each visit), 16 Y.U. (4 Y.U.×4 sites), 40 Y.U. (10 Y.U.×4 sites), as well as 80 Y.U. (administered subcutaneously). The dose can be administered for example, as described in Example 3 or monthly. Inclusion criteria can include presence of a solid tumor and measurable disease. Primary and/or secondary endpoints can include progression free survival (may be defined by RECIST, or may be defined by immune related response criteria modified for RECIST, or by Choi criteria), delayed time to progression, tumor response rate (i.e. radiographic response defined by 6 to 12 months prior to enrollment by imaging of an untreated tumor during the time period, stability or progression as measured by RECIST and/or Choi criteria and/or compared to non-irradiated lesions in the subject), change in tumor growth rate kinetics (such as 6 months pre-treatment versus 6 months post-treatment), antigen-specific T cell responses (e.g., Brachyury-specific $CD8^+$ and/or $CD4^+$ T cells emerging or expanding on treatment), overall survival or combinations thereof.

The subject's response to the yeast-based immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

The yeast-based immunotherapeutic composition is expected to be safe and well-tolerated with no significant toxicities. In addition, the yeast-Brachyury immunotherapeutic composition is expected to improve progression free survival, produce treatment-emergent Brachyury-specific T cell responses in at least some or a majority of patients and/or reduce tumor growth rate. The treatment group of subjects is expected to have a delayed time to progression, as compared to the control subjects who have not received yeast-based immunotherapy. A goal of the study is to achieve a trending toward, and preferably a statistical significant increase in the median PFS from the expected median PFS of the chordoma population disclosed in this example. By way of illustration, a statistical goal of a median PFS of 9 months may be achieved, wherein for the relevant chordoma population under study, the expected median PFS may be typically about 5 months.

Example 13

The following example describes a phase 2 clinical trial in chordoma subjects having a first recurrence of a non-resectable lesion, wherein the lesion has been previously irradiated.

A randomized phase 2 clinical trial in these chordoma subjects is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 (GI-6301) or SEQ ID NO:20 (GI-6305). The trial will be statistically powered to enroll the appropriate number of patients to evaluate clinical efficacy using the criteria described below.

The trial is run as a double-blind or open-label, multicenter trial. All patients receive routine monitoring and/or standard of care treatments of radiation therapy, systemic drug therapy or a combination thereof with treatment arm patients receiving several serial injections of yeast-Brachyury immunotherapeutic composition (i.e. GI-6301 or other yeast-Brachyury immunotherapeutics). For example, the protocol can utilize dose ranges of 4 Y.U. (1 Y.U.×4 sites, meaning that 1 Y.U. of GI-6301 is administered at 4 different sites on the body of the patient each visit), 16 Y.U. (4 Y.U.×4 sites), 40 Y.U. (10 Y.U.×4 sites), as well as 80 Y.U. (administered subcutaneously). The dose can be administered for example, as described in Example 3 or monthly. Inclusion criteria can include presence of a solid tumor and measurable disease. Primary and/or secondary endpoints can include progression free survival (may be defined by RECIST, or may be defined by immune related response criteria modified for RECIST, or by Choi criteria), delayed time to progression, tumor response rate (i.e. radiographic response defined by 6 to 12 months prior to enrollment by imaging of an untreated tumor during the time period, stability or progression as measured by RECIST and/or Choi criteria and/or compared to non-irradiated lesions in the subject), change in tumor growth rate kinetics (such as 6 months pre-treatment versus 6 months post-treatment), antigen-specific T cell responses (e.g., Brachyury-specific $CD8^+$ and/or $CD4^+$ T cells emerging or expanding on treatment), overall survival or combinations thereof.

The subject's response to the yeast-based immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

The yeast-based immunotherapeutic composition is expected to be safe and well-tolerated with no significant toxicities. In addition, the yeast-Brachyury immunotherapeutic composition is expected to improve progression free survival, produce treatment-emergent Brachyury-specific T cell responses in at least some or a majority of patients and/or reduce tumor growth rate. The treatment group of subjects is expected to have a delayed time to progression, as compared to the control subjects who have not received yeast-based immunotherapy. A goal of the study is to achieve a trending toward, and preferably a statistical significant increase in the median PFS from the expected median PFS of the chordoma population disclosed in this example. By way of illustration, a statistical goal of a median PFS of 9 months may be achieved, wherein for the relevant chordoma population under study, the expected median PFS may be typically about 5 months.

Example 14

The following example describes a phase 2 clinical trial in chordoma subjects having metastatic disease and a lesion that has not previously been irradiated.

A randomized phase 2 clinical trial in these chordoma subjects is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 (GI-6301) or SEQ ID NO:20 (GI-6305). The trial will be statistically powered to enroll the appropriate number of patients to evaluate clinical efficacy using the criteria described below.

The trial is run as a double-blind or open-label, multi-center trial. All patients receive routine monitoring and/or standard of care treatments of radiation therapy, systemic drug therapy or a combination thereof with treatment arm patients receiving several serial injections of yeast-Brachyury immunotherapeutic composition (i.e. GI-6301 or other yeast-Brachyury immunotherapeutics). For example, the protocol can utilize dose ranges of 4 Y.U. (1 Y.U.×4 sites, meaning that 1 Y.U. of GI-6301 is administered at 4 different sites on the body of the patient each visit), 16 Y.U. (4 Y.U.×4 sites), 40 Y.U. (10 Y.U.×4 sites), as well as 80 Y.U. (administered subcutaneously). The dose can be administered for example, as described in Example 3 or monthly. Inclusion criteria can include presence of a solid tumor and measurable disease. Primary and/or secondary endpoints can include progression free survival (may be defined by RECIST, or may be defined by immune related response criteria modified for RECIST, or by Choi criteria), delayed time to progression, tumor response rate (i.e. radiographic response defined by 6 to 12 months prior to enrollment by imaging of an untreated tumor during the time period, stability or progression as measured by RECIST and/or Choi criteria and/or compared to non-irradiated lesions in the subject), change in tumor growth rate kinetics (such as 6 months pre-treatment versus 6 months post-treatment), antigen-specific T cell responses (e.g., Brachyury-specific $CD8^+$ and/or $CD4^+$ T cells emerging or expanding on treatment), overall survival or combinations thereof.

The subject's response to the yeast-based immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

The yeast-based immunotherapeutic composition is expected to be safe and well-tolerated with no significant toxicities. In addition, the yeast-Brachyury immunotherapeutic composition is expected to improve progression free survival, produce treatment-emergent Brachyury-specific T cell responses in at least some or a majority of patients and/or reduce tumor growth rate. The treatment group of subjects is expected to have a delayed time to progression, as compared to the control subjects who have not received yeast-based immunotherapy. A goal of the study is to achieve a trending toward, and preferably a statistical significant increase in the median PFS from the expected median PFS of the chordoma population disclosed in this example. By way of illustration, a statistical goal of a median PFS of 9 months may be achieved, wherein for the relevant chordoma population under study, the expected median PFS may be typically about 5 months.

Example 15

The following example describes a phase 2 clinical trial in chordoma subjects having metastatic disease and a lesion that has previously been irradiated.

A randomized phase 2 clinical trial in these chordoma subjects is run using a yeast-Brachyury immunotherapeutic composition as described herein (e.g., a yeast-Brachyury immunotherapeutic composition comprising a whole, heat-killed *Saccharomyces* yeast that has expressed SEQ ID NO:8 (GI-6301) or SEQ ID NO:20 (GI-6305). The trial will be statistically powered to enroll the appropriate number of patients to evaluate clinical efficacy using the criteria described below.

The trial is run as a double-blind or open-label, multi-center trial. All patients receive routine monitoring and/or standard of care treatments of radiation therapy, systemic drug therapy or a combination thereof with treatment arm patients receiving several serial injections of yeast-Brachyury immunotherapeutic composition (i.e. GI-6301 or other yeast-Brachyury immunotherapeutics). For example, the protocol can utilize dose ranges of 4 Y.U. (1 Y.U.×4 sites, meaning that 1 Y.U. of GI-6301 is administered at 4 different sites on the body of the patient each visit), 16 Y.U. (4 Y.U.×4 sites), 40 Y.U. (10 Y.U.×4 sites), as well as 80 Y.U. (administered subcutaneously). The dose can be administered for example, as described in Example 3 or monthly. Inclusion criteria can include presence of a solid tumor and measurable disease. Primary and/or secondary endpoints can include progression free survival (may be defined by RECIST, or may be defined by immune related response criteria modified for RECIST, or by Choi criteria), delayed time to progression, tumor response rate (i.e. radiographic response defined by 6 to 12 months prior to enrollment by imaging of an untreated tumor during the time period, stability or progression as measured by RECIST and/or Choi criteria and/or compared to non-irradiated lesions in the subject), change in tumor growth rate kinetics (such as 6 months pre-treatment versus 6 months post-treatment), antigen-specific T cell responses (e.g., Brachyury-specific $CD8^+$ and/or $CD4^+$ T cells emerging or expanding on treatment), overall survival or combinations thereof.

The subject's response to the yeast-based immunotherapeutic composition can be compared to subjects being treated in the same manner, but without addition of the immunotherapeutic composition or the immunotherapeutic composition in combination with a second line therapy such as radiation therapy, surgical resection, targeted drug therapy or a combination thereof.

The yeast-based immunotherapeutic composition is expected to be safe and well-tolerated with no significant toxicities. In addition, the yeast-Brachyury immunotherapeutic composition is expected to improve progression free survival, produce treatment-emergent Brachyury-specific T cell responses in at least some or a majority of patients and/or reduce tumor growth rate. The treatment group of subjects is expected to have a delayed time to progression, as compared to the control subjects who have not received yeast-based immunotherapy. A goal of the study is to achieve a trending toward, and preferably a statistical significant increase in the median PFS from the expected median PFS of the chordoma population disclosed in this example. By way of illustration, a statistical goal of a median PFS of 9 months may be achieved, wherein for the relevant chordoma population under study, the expected median PFS may be typically about 5 months.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed is:

1. A method to treat chordoma, comprising administering to an individual who has chordoma, an immunotherapeutic composition comprising:
  a) a yeast vehicle; and
  b) a cancer antigen comprising at least one Brachyury antigen wherein the Brachyury antigen has an amino acid sequence represented by positions 2-435 of SEQ ID NO:6.

2. The method of claim 1, wherein the individual is an individual having a non-resectable, locally recurring lesion.

3. The method of claim 2, wherein local recurrence of the lesion occurs between 3 and 9 months prior to administration of the immunotherapeutic composition.

4. The method of claim 1, wherein the individual is an individual having oligometastatic disease.

5. The method of claim 1, wherein the individual is an individual having first recurrence of a non-resectable lesion or a resectable lesion.

6. The method of claim 1, wherein the individual is an individual having metastatic disease.

7. The method of claim 1, wherein the individual is being treated or has been treated with another therapy for cancer.

8. The method of claim 1, wherein the individual is being treated or has been treated with radiation therapy.

9. The method of claim 8, wherein the radiation therapy is administered concurrently with the administration of the immunotherapeutic composition.

10. The method of claim 8, wherein the radiation therapy is administered sequentially with the administration of the immunotherapeutic composition.

11. The method of claim 1, wherein the individual is being treated or has been treated with tumor resection.

12. The method of claim 1, wherein the individual is being treated or has been treated with chemotherapy.

13. The method of claim 1, wherein the wherein the individual is being treated or has been treated with a drug targeted therapy selected from the group consisting of tyrosine kinase inhibitors, EGFR inhibitors, and STAT3 inhibitors.

14. The method of claim 1, wherein the wherein the individual is being treated or has been treated with administration of one or more additional immunotherapeutic compositions.

15. The method of claim 1, wherein the Brachyury antigen comprises SEQ ID NO:18, positions 2-435 of SEQ ID NO:18, or an amino acid sequence that is at least 95% identical to SEQ ID NO:18.

16. The method of claim 1, wherein the Brachyury antigen comprises SEQ ID NO:2, positions 2-435 of SEQ ID NO:2, or an amino acid sequence that is at least 95% identical to SEQ ID NO:2.

17. The method of claim 1, wherein the Brachyury antigen has an amino acid sequence represented by SEQ ID NO:8, or an amino acid sequence that is at least 95% identical to SEQ ID NO:8.

18. The method of claim 1, wherein the Brachyury antigen has an amino acid sequence represented by SEQ ID NO:20, or an amino acid sequence that is at least 95% identical to SEQ ID NO:20.

19. The method of claim 1, wherein the yeast vehicle is a whole inactivated yeast.

20. The method of claim 19, wherein the whole yeast is heat-inactivated.

21. The method of claim 1, wherein the yeast vehicle expresses the antigen.

22. The method of claim 1, wherein the yeast is from *Saccharomyces cerevisiae*.

23. The method of claim 1, wherein the composition is formulated in a pharmaceutically acceptable excipient suitable for administration by injection of a subject.

24. The method of claim 1, wherein the subject is administered the immunotherapeutic composition in a dose from about 0.1 Y.U. to about 100 Y.U.

25. The method of claim 1, wherein the immunotherapeutic composition is administered weekly.

26. The method of claim 1, wherein the immunotherapeutic composition is administered every other week.

27. The method of claim 1, wherein the immunotherapeutic composition is administered monthly.

28. The method of claim 1, wherein the immunotherapeutic composition is administered weekly for 5 weeks followed by monthly.

29. The method of claim 1, wherein the immunotherapeutic composition is administered at two week intervals for 7 rounds of treatment, followed by monthly.

30. The method of claim 1, wherein the immunotherapeutic composition is administered at more than one site on the individual to form a single dose.

31. The method of claim 1, wherein the immunotherapeutic composition is administered concurrently with another therapy for cancer.

32. The method of claim 8, wherein the radiation therapy is administered concurrently with the administration of the immunotherapeutic composition.

33. The method of claim 1, wherein the subject is administered the immunotherapeutic composition in a dose from about 10 Y.U. to about 80 Y.U.

34. The method of claim 1, wherein the subject is administered the immunotherapeutic composition in a dose of 2 Y.U., 40 Y.U. or 80 Y.U.

* * * * *